US008288127B2

(12) United States Patent
Schneider et al.

(10) Patent No.: US 8,288,127 B2
(45) Date of Patent: Oct. 16, 2012

(54) PROTEIN EXPRESSION SYSTEMS

(75) Inventors: Jane C. Schneider, San Diego, CA (US); Lawrence C. Chew, San Diego, CA (US); Anne Kathryn Badgley, Poway, CA (US); Thomas Martin Ramseier, Newton, MA (US)

(73) Assignee: Pfenex, Inc, San Diego, CA (US)

( * ) Notice: Subject to any disclaimer, the term of this patent is extended or adjusted under 35 U.S.C. 154(b) by 447 days.

(21) Appl. No.: 12/512,930

(22) Filed: Jul. 30, 2009

(65) Prior Publication Data

US 2009/0325230 A1 Dec. 31, 2009

Related U.S. Application Data

(62) Division of application No. 10/994,138, filed on Nov. 19, 2004, now abandoned.

(60) Provisional application No. 60/523,420, filed on Nov. 19, 2003, provisional application No. 60/537,147, filed on Jan. 16, 2004.

(51) Int. Cl.
*C12N 15/78* (2006.01)
*C12N 15/00* (2006.01)
*C12N 15/09* (2006.01)
*C12N 15/11* (2006.01)

(52) U.S. Cl. ....... 435/71.1; 435/471; 435/477; 435/481; 536/23.7; 536/24.1

(58) Field of Classification Search ........................ None
See application file for complete search history.

(56) References Cited

U.S. PATENT DOCUMENTS

| | | | |
|---|---|---|---|
| 4,511,503 A | 4/1985 | Olson | |
| 4,695,455 A | 9/1987 | Barnes | |
| 4,755,465 A | 7/1988 | Gray | |
| 4,861,595 A | 8/1989 | Barnes | |
| 4,920,048 A | 4/1990 | Diderichsen | |
| 5,055,294 A | 10/1991 | Gilroy | |
| 5,128,130 A | 7/1992 | Gilroy | |
| 5,169,760 A | 12/1992 | Wilcox | |
| 5,232,840 A | 8/1993 | Olins | |
| 5,281,532 A | 1/1994 | Rammler | |
| 5,527,883 A | 6/1996 | Thompson | |
| 5,691,185 A | 11/1997 | Dickely et al. | |
| 5,840,554 A | 11/1998 | Thompson | |
| 6,291,245 B1 | 9/2001 | Kopetzki et al. | |
| 6,413,768 B1 | 7/2002 | Galen | |
| 6,752,994 B2 | 6/2004 | Jacobs, Jr. et al. | |
| 6,927,026 B1 | 8/2005 | Pompejus et al. | |
| 2002/0193568 A1 | 12/2002 | Matthews et al. | |
| 2004/0005676 A1 | 1/2004 | Greenberg et al. | |
| 2004/0171824 A1 | 9/2004 | Scrable et al. | |
| 2005/0186666 A1 | 8/2005 | Schneider et al. | |

FOREIGN PATENT DOCUMENTS

| | | |
|---|---|---|
| EP | 0207459 | 1/1987 |
| EP | 0 972 838 B1 | 9/2004 |
| JP | 4320689 | 11/1992 |
| WO | WO 97/04110 | 2/1997 |
| WO | WO-99-27108 | 6/1999 |
| WO | WO-03-062399 A2 | 7/2003 |
| WO | WO-03-068926 A2 | 8/2003 |
| WO | WO 03/089455 | 10/2003 |
| WO | WO-2005-052151 | 6/2005 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Drahos et al., "Tracking Recombinant Organisms in the Environment: B-Galactosidase as a Selectable Non-Antibiotic Marker for Fluorescent Pseudomonads," Nature Biotech. 4:439-444 (1986).
Jeenes et al., "Expression of biosynthetic genes from *Pseudomonas aeruginosa* and *Escherichia coli* in the heterologous host," Mol Gen Genet 203(3):421-429 (1986).
King et al., "The *Bradyrhizobium japonicum* Proline Biosynthesis Gene proC Is Essential for Symbiosis," Appl Environ. Microbiol. 66(12):5469-5471 (2000).
Knipfer et al., "Unmarked Gene Integration into the Chromosome of *Mycobacterium smegmatis* via Precise Replacement of the pyrF Gene," Plasmid 37(2):129-140 (1997).
Sadler et al., "A perfectly symmetric lac operator binds the lac repressor very tightly," PNAS USA 80(22):6785-6789 (1983).
Amann et al., "Tightly Regulated tac Promoter Vectors Useful for the Expression of Unfused and Fused Proteins in *Escherichia coli*," Gene, 1988, pp. 301-315, vol. 69, No. 2.
Barker et al., Cross Feeding of Thymine in *E. coli*, Biochem. J., 1976, pp. 221-227, vol. 157, No. 1.
Barth, A.L., et al., "Complementation of Methionine Auxotrophs of *Pseudomonas aeruginosa* from Cystic Fibrosis," Current Microbiology, 1998, pp. 190-195, vol. 36.
Baysee et al., "Impact of Mutations in hemA and hemH Genes on Pyoverdine Production by *Pseudomonas fluorescens* ATCC17400," FEMS Microbiology Letters, 2001, pp. 57-63, vol. 205.
Boeke et al., "A Positive Selection for Mutants Lacking Orotodine-5'-Phosphate Decarboxylase Activity in Yeast, 5-Fluoro-Orotic Acid Resistance," Mol. Gen. Genet., 1984, pp. 345-345, vol. 197.
Botstein et al., "Principles and Practice of Recombinant DNA Research with Yeast," *The Molecular Biology of the Yeast Saccharomyces cerevisiae, Metabolism and Gene Expression*, 1982, pp. 607-636.
Calos, M., DNA Sequence for a Low-level Promoter of the lac Repressor Gene and an "up" Promoter Mutation, Nature, 1978, pp. 762-765, vol. 5673.
Calos, M., et al., "DNA Sequence Alteration Resulting from a Mutation Impairing Promoter Function in the lac Repressor Gene," Mol. & Gen. Genet., 1980, pp. 559-560, vol. 183, No. 3.
Chu et al., "Pyrimidine Biosynthetic Pathway of *Pseudomonas fluorescens*," J. Gen. Microbiology, 1990, pp. 875-880.

(Continued)

*Primary Examiner* — Maria Marvich
(74) *Attorney, Agent, or Firm* — Wilson, Sonsini, Goodrich & Rosati

(57) ABSTRACT

The present invention provides an improved expression system for the production of recombinant polypeptides utilizing auxotrophic selectable markers. In addition, the present invention provides improved recombinant protein production in host cells through the improved regulation of expression.

20 Claims, 6 Drawing Sheets

OTHER PUBLICATIONS

Cost et al., "A Useful Colony Color Phenotype Associates with the Yeast Selectable/Counter Selectable Marker MET15," *Yeast*, 1996, pp. 939-941.

Dickely et al., "Isolation of *Lactococcus lactis* Nonsense Suppressors and Construction of a Good-Grade Cloning Vector," *Mol. Microbiol.*, 1995, pp. 859-847, vol. 15.

Droge et al., "Horizontal Gene Transfer as a Biosafety Issue: A Natural Phenomenon of Public Concern," *J. Biotechnology*, 1998, pp. 75-90, vol. 65, No. 1.

Ellis et al., "Novel *Bacillus thuringiensis* Binary Insecticidal Crystal Proteins Active on Western Corn Rootwork, Biabrotica virgifera vergifera LeConte," *Applied and Environmental Microbiology*, 2002, pp. 1137-1145, vol. 68, No. 3.

El-Sayed et al., Quorum-sending-dependent Regulation of Biosynthesis of the polyketide Antibiotic Mupirocin in *Pseudomonas fluorescens* NCIMB 10586, *Microbiology*, 2001, pp. 217-2139, vol. 147.

Fiedler et al., "ProBA Complementation of an Auxotrophic *E. coli* Strain Improves Plasmid Stability and Expression Yield During Fermenter Production of a Recombinant Antibody Fragment," *Gene*, 2001, pp. 111-118, vol. 274.

Frank et al., "Thermodynamics of the Interactions of lac Repressor with Variants of the Symmetric lac operator: Effects of converting a Consensus Site to a Non-Specific Site," *J. or Molecular Biology*, 1997, pp. 1186-1206, vol. 267, No. 5.

Fukumoto et al., "Transformation of pBR322-Derived Plasmids in Phytopathogenic *Pseudomonas avenae* and Enhanced Transformation in Its Proline-Auxotrophic Mutant," *Current Microbiology*, 1997, pp. 138-143, vol. 34.

Gallagher et al., "Penicillin-Induced Anaphylaxis in a Patient Under Hypotensive Anaesthesia," *Oral Surg. Oral Med. Oral Pathol.*, 1983, pp. 361-364, vol. 56.

Gebhard et al., "Transformation of *Acinetobacter* sp. Strain BD413 by Transgenic Sugar Beet DNA," *Appl. And Environ. Microbiol.*, 1998, pp. 1550-1554, vol. 64, No. 4.

Glascock et al., "Using Chromosomal lacIQI to Control the Expression of Genes on High-copy-number Plasmids in *Escherichia coli*," *Gene*, 1998, pp. 221-231, vol. 223.

Hoffman et al., "Foreign DNA Sequences are Received by a Wild Type Strain of *Aspergillus niger* After Co-culture with Transgenic Higher Plants," *Curr. Genet.*, 1994, pp. 70-76, vol. 27, No. 1.

Jensen, "The *Escherichia coli* K12 "Wild Types" W3110 and MG1655 Have an rph Frameshift Mutation that Leads to Pyrminidine Starvation Due to Low pyre Expression Levels," *J. Bacteriology*, 1993, pp. 3401-3407, vol. 175, No. 11.

Jorro et al., "Anaphylaxis to Erythromycin," *Ann. Allergy Asthma Immunol.*, 1996, pp. 456-458, vol. 77.

Kerr et al., "Cross Feeding of NAD in *E. coli* Auxotrophic for NAD Synthesis," *J. Bact.*, 1973, pp. 982-986, vol. 115, No. 3.

Kisters-Woike, B., et al., "A Model of the *lac* Repressor-operator Complex Based on Physical and Genetic Data," *Eur. J. Biochem.*, 1991, pp. 411-419, vol. 198.

Krishna, R.V., et al., "Biosynthesis of Proline in *Pseudomonas aeruginosa*; Properties of γ-Glutamyl Phosphate Reductase and 1-Pyrroline-5-Carboxylate Reductase," *Biochem. J.*, 1979, pp. 223-230, vol. 181.

Mac Cormick et al., "Construction of a Food-Grade Host/Vector System for *Lactococcus lactis* Based on the Lactose Operon," *FEMS Microbiol. Lett.*, 1995, pp. 105-109, vol. 127.

Meinander et al., "Fed-batch Xylitol Production with Two Recombinant *Saccharomyces cerevisiae* Strains Expressing XYL1 at Different Levels, using Glucose as a Cosubstrate: A Comparison of Production Parameters and Strain Stability," *Biotechnology and Bioengineering*, 1997, pp. 391-399, vol. 54, No. 4.

Mercer et al., "Fate of Free DNA and Transformation of the Oral Bacterium *Streptococcus gordonoii* DLI by Plasmid DNA in Human Saliva," *Appl. and Environ. Microbiol.*, 1999, pp. 6-10, vol. 65, No. 1.

Mergeay, M. and Jozef Gerits, "F'—Plasmid Transfer from *Escherichia coli* to *Pseudomonas fluorescens*," *J. Bacteriology*, Jul. 1978, pp. 18-28, vol. 135, No. 1.

Molina, L., et al., "Construction of an Efficient Biologically contained *Pseudomonas putida* Strain and Its Survival in Outdoor Assays," *Appl. and Environ. Microbiol.*, Jun. 1998, pp. 2072-2078, vol. 64, No. 6.

Muller et al., "Repression of lac Promoter as a Function of Distance, Phase, and Quality of an Auxillary lac Operator," *J. Mol. Biology*, 1996, pp. 21-29, vol. 257, No. 1.

Muller et al., "Dimeric lac Repressors Exhibit Phase-dependent Cooperativity," *J. Mol. Biology*, 1998, pp. 851-857, vol. 284, No. 4.

Oehler et al., "Quality and Position of the Three lac Operators of *E. coli* Define efficiency and Repression," *EMBO Journal*, 1994, pp. 3348-3355, vol. 13, No. 14.

Pronk, "Auxotrophic Yeast Strains in Fundamental and Applied Research," *App. And Environ. Micro.*, 2002, pp. 2095-2100, vol. 68, No. 5.

Salyers, Gene Transfer in the Mammalian Intestinal Tract, *Curr. Opin. In Biotechnol.*, 1993, pp. 294-298, vol. 4, No. 3.

Savioz et al., "Comparison of proC and Other Housekeeping Genes of *Pseudomonas aeruginosa* with Their Counterparts in *Escherichia coli*," *Gene*, 1990, pp. 107-111, vol. 86.

Schubbert et al., "Foreign (M13) DNA Ingested by Mice Reaches Peripheral Leukocytes, Spleen and Liver via the Intestinal Wall Mucosa and Can be Covalently Linked to Mouse DNA," *PNAS USA*, 1997, pp. 961-966, vol. 94.

Skogman et al., "Temperature-dependent Retention of a Tryptophan-operon-bearing Plasmid in *Escherichia coli*," *Gene*, 1984, pp. 117-122, vol. 31.

Sorensen et al., "A Food-Grade Cloning System for Industrial Strains of *Lactococcus lactis*," *Appl. Environ. Microbiol.*, 2000, pp. 1253-1258, vol. 66.

Sprenger et al., "Selection of Auxotrophic and Carbohydrate-Negative Mutants in Penicillin-Resistant *Klebsiella pneumoniae* by Nalidixic Acid Treatment," *FEMS Microbiol. Lett.*, 1986, pp. 299-304, vol. 37, No. 3.

Stark, "Multicopy Expression Vectors Carrying the lac Repressor Gene for Regulated High-level Expression of Genes in *Escherichia coli*," *Gene*, 1987, pp. 255-267, vol. 51.

Struhl et al., "Functional Genetic Expression of Eukaryotic DNA in *Escherichia coli*," *PNAS USA*, 1976, pp. 1471-1475, vol. 73.

Strych, U., et al., "Orotidine-5'-Monophosphate Decarboxylase from *Pseudomonas aeruginosa* PAO1: Cloning, Overexpression, and Enzyme Characterization," *Current Microbiology*, 1994, pp. 353-359, vol. 29.

Troxler et al., "Conjugate Transfer of Chromosomal Genes Between Fluorescent Pseudomonads in the Rizosphere of Wheat," *Appl. And Environ. Microbiol.*, 1997, pp. 213-219, vol. 63, No. 1.

Zhang, J.K., et al., "Directed Mutagenesis and Plasmid-based Complementation in the Methanogenic Archaeon *Methanosarcina acetivorans* C2A Demonstrated by Genetic Analysis of Proline Biosynthesis," *J. Bacteriol.*, Mar. 2002, pp. 1449-1454, vol. 184, No. 5.

Adari et al. "Expression of the Human T-Cell Receptor Vβ5.3 in *Escherichia coli* by Thermal Induction of the *trc* Promoter: Nucleotide Sequence of the lac/ts Gene." DNA *Cell Biol.* 1995, 14:945-950.

Artiguenave et al., "High-efficiency transposon mutagenesis by electroporation of a *Pseudomonas fluorescens* strain." FEMS Microbiol. Lett., 1997, 153(2): 363-9.

Buchanan and Gibbons (eds). *Bergey's Manual of Determinative Bacteriology*, 8th ed., 1974, pp. 217-289, The Williams & Wilkins Co, Baltimore, MD.

Bukrinsky et al. "Multicopy expression vector based on temperature-regulated *lac* repressor: expression of human immunodeficiency virus *env* gene in *Escherichia coli*." *Gene*, 1989, 70:415-417.

Calos and Miller. "The DNA Sequence Change Resulting from the $I^{Q1}$ Mutation, which Greatly Increases Promoter Strength." *Mol. & Gen. Genet.*, 1980, 183(3):559-560.

Davison, "Genetic Tools for Pseudomonads, Rhizobia, and Other Gram-Negative Bacteria," Biotechniques 32(2):386-401, 2002.

De Boer et al. "The tac promoter: A functional hybrid derived from the trp and lac promoters," *Proc. Natl. Acad. Sci.*, vol. 80, pp. 21-25, Jan. 1983.

De Santis et al. "Creation of a Productive, Highly Enantioselective Nitrilas through Gene Site Saturation Mutagenesis (GSSM)." *J. Amer. Chem. Soc.*, 2003, 125:11476-11477.

Dougherty et al. "Cloning Human Pyrroline-5-carboxylate Reductase cDNA by Complementation in *Saccharomyces cerevisiae*\*." *The Journal of Biological Chemistry*, 1992, 267(2):871-875.

Fickert and Mueller-Hill. "How Lac Repressor Finds *lac* Operator in Vitro." *J. Mol. Biol.*, 1992, 226(1):59-68.

Frishman et al. Starts of bacterial genes: estimating the reliability of computer predictions, *Gene*, Jul. 8, 1999, 234(2):257-265.

Goryshin and Reznikoff. "In5 in vitro transposition." *Journal of Biological Chemistry*, 1998, 273(13):7367-7374.

Hasan and Szybalski. "Construction of *lacI*ts and *lacI*$^q$ts expression plasmids and evaluation of the termosensitive lac repressor." *Gene*, 1995, 163(1):35-40.

Higgins and Sharp. "Fast and sensitive multiple sequence alignments on a microcomputer." *Comp. Appl'ns in Biosci.*, 1989,5:151-153.

Higgins and Sharp. "CLUSTAL: a package for performing multiple sequence alignment on a microcomputer." *Gene*, Dec. 15, 1988, 73(1):237-244.

Hochuli, "Purification of Recombinant Proteins with Metal Chelate Absorbent." *Genetic Engineering, Priniciple and Methods*, 1990, Setlow, ed., Plenum Press, NY.

Landry et al. "Safety evaluation of an α-amylase enzyme preparation derived from the archaeal order Thermococcales as expressed in *Pseudomonas fluorescens* biovar I." *Regulatory Toxicology and Pharmacology*, 2003, 37(1):149-168.

Lee et al., "Bacterial Expression and in Vitro Refolding of a Single-Chain Fv Antibody Specific for Human Plasma," *Protein Expr. Purif.*, 2002, 25(1):166-173.

Menz et al. "The identification, cloning and functional expression of the gene encoding orotidine 5'-monophosphate (OMP) decarboxylase from *Plasmodium falciparum*." *Annals of Tropical Medicine & Parasitology*, 2002, 96(4):1-8.

Needleman and Wunsch. "A General Method Applicable to the Search for Similarities in the Amino Acid Sequence of Two Proteins." *J. Molec. Biol.*, Mar. 1970, 48(3):443-453.

Nida and Cleary. "Insertional inactivation of streptolysin S expression in *Streptococcus pyogenes*." *J. Bacteriol.*, 1983, 155(3):1156-1161.

Pearson, W.R. "Searching Protein Sequence Libraries: Comparison of the Sensitivity and Selectivity of the Smith-Waterman and FASTA Algorithms." *Genomics*, Nov. 1991, 11(3):635-650.

Riesenberg et al. "High cell density cultivation of *Escherichia coli* at controlled specific growth rate." *J Biotechnol*, 1991, 20(1):17-27.

Roeder and Collmer. "Marker-exchange mutagenesis of a pectate lyase isozyme gene in *Erwinia chrysanthemi*." *J Bacteriol.*, 1985, 164(1):51-56.

Sambrook, et al. Molecular Cloning a Laboratory Manual, 2$^{nd}$ ed., 1989, pp. 16.7-16.8.

Sanchez-Romero and De Lorenzo. << Genetic Engineering of Nonpathogenic *Pseudomonas* strains as Biocatalysts for Industrial and Environmental Processes. *Manual of Industrial Microbiology and Biotechnology*, 1999, pp. 460-474, Demain and Davies, Eds., ASM Press, Washington , D.C.

Schweizer. H. "Vectors to express foreign genes and techniques to monitor gene expression for Pseudomonads." *Current Opinion in Biotechnology*, 2001, 12(5):439-445.

Slater and Williams. The Expression of Foreign DNA in Bacteria, *Molecular Biology and Biotechnology*, 2000, pp. 125-154, Walker and Rapley, eds., The Royal Society of Chemistry, Cambridge, UK.

Smith and Waterman. "Comparison of Biosequences." *Adv. Appl. Math.*, 1981, 2:482-489.

Smith and Waterman. "Identification of Common Molecular Subsequences." *J. Molec. Biol.*, 1981, 147:195-197.

Stevens, R.C. "Design of high-throughput methods of protein production for structural biology." *Structures*, 2000, R177-R185.

Suzek et al. A probabilistic method for identifying start codons in bacterial genomes, *Bioinformatics*, Dec. 2001, 17(12):1123-1130.

Swint-Kruse et al. "Perturbation from a Distance: Mutations that Alter LacI Function through Long-Range Effects." *Biochemistry*, 2003, 42(47):14004-14016.

Toder, D.S., "Gene replacement in *Pseudomonas aeruginosa*." *Methods in Enzymology*, 1994, 235:466-474.

Tsuda and Nakazawa. *Gene*, Dec. 22, 1993, 136(1-2):257-262.

Verbruggen et al. "Osmoregulation of a Pyrroline-5-Carboxylate Reductase Gene in *Arabidopsis thaliana*." *Plant Physiol.*, 1993, 103:771-781.

Wells et al. "Cassette mutagenesis: an efficient method for generation of multiple mutations at defined sites." *Gene*, 1985, 34(2-3):315-323.

Werle, E. "Direct sequencing of polymerase chain reaction products," *Laboratory Methods for the Detection of Mutations and Polymorphisms in DNA*, 1997, pp. 163-174.

Wood et al. "Versatile Cloning Vector for *Pseudomonas aeroginosa*." *J. Bact.*, Mar. 1981, 145(3):1448-1451.

Degryse (1991) "Stability of a host-vector system based on complementation of an essential gene in *Escherichia coli*" *Journal of Biotechnology* 18(1/2): pp. 29-39.

Lin et al. (2001) "New selectable marker/auxotrophic host strain combinations for molecular genetic manipulation of *Pichia pastoris*" *Gene* 263(1-2): pp. 159-169.

Pelicic et al. (1996) "Generation of unmarked directed mutations in Mycobacteria using sucrose counter-selectable suicide vectors" *Molecular Microbiology* 20(5): pp. 919-925.

Schneider et al. (2004) "Use of pyrF to stack multiple deletions in *Pseudomonas fluorescens* and to stabilize protein production plasmids without antibiotic resistance markers" [abstract] In: Abstracts of the General Meeting of the American Society for Microbiology; May 23-27, 2004; New Orleans, LA. vol. 104, p. 308.

Schneider et al. (2005) "Auxotrophic markers pyrF and proC can replace antibiotic markers on protein production plasmids in high-cell-density *Pseudomonas fluorescens* fermentation" *Biotechnology Progress* 21(2): pp. 343-348.

Bagdasarian et al., "Specific-purpose plasmid cloning vectors," *Gene*, Dec. 1981, 16(1-3):237-247.

Bagdasarian and Timmis, "Host: Vector Systems for Gene Cloning in Pseudomonas," *Curr. Topics Mierobiol Immunol.*, 1982, 96:47-67.

Cho et al., "Production and in vitro refolding of a single-chain antibody specific for human plasma apolipoprotein A-I," *J. Biotechnology*, 2000, 77(2-3)169-178.

Clark-Curtiss and Curtiss, "Analysis of Recombinant DNA Using *Escherichia coil* Minicells," *Methods in Enzymology*, 1983, Wu et al, eds., 101:347-362.

Davis and Mingioli, "Mutants of *Escherichia Coli* Requiring Methionine or Vitamin $B_{12}$," *J. Bact.*, 1950, 60:17-28.

Graupner and Wackernagel, "A broad-host-range expression vector series including a Ptac test plasmid and its application in the expression of the dod gene of *Serratia marcescens* (coding for ribulose-5-phosphate 3-epimerase) in *Pseudomonas saiszeri*," *Biomolec. Eng.*, Oct. 2000, 17(1): 11-16.

Hannig and Makrides, "Strategies for optimizing heterologous protein expression in *Escherichia coli*," *TIBTECH*, 1998, 16:54-60.

Hayase, N., "Secretion of Human Epidermal Growth Factor (EGF) in Autotrophic Culture by a Recombinant Hydrogen-Utilizing Bacterium, *Pseudomonas pseudoflava*, Carrying Broad-Host-Range EGF Secretion Vector pKSEGF2," *Appl. Envir Microbiol.*, Sep. 1994, 60(9):3336-3342.

Herfron et al., "Translocation of a plasmid DNA sequence which mediates ampicillin resistance: Molecular nature and specificity of insertion," *Proc. Nat'l Acad. Sci.*, Sep. 1975, 72(9):3623-3627.

Holtwick et al., "A novel rolling-circle-replicating plasmic! from *Pseudomonas putida* P8: molecular characterization and use as vector," *Microbiology*. Feb. 2001, 147, 337-344.

Ishii et al., "Elastase gene expression in non-elastase-producing *Psuedomonas aeruginosa* strains, using novel shuttle vector systems," *FEMS Microbiol. Lett.*, Mar. 1, 1994, 116(3):307-314.

Jones and Gutterson, "An efficient mobilizable cosmid vector, pRK7813, and its use in a rapid method for marker exchange in *Pseudomonas fluorescens* strain HV37a," *Gene*, 1987, 61(3):299-306.

Lanzer and Bujard, "Promoters largely determine the efficiency of repressor action," *Proc. Natl. Acad. Sci.*, 1988, 85:8973-8977.

Lushnikov et al., "Shuttle Vector for *Escherichia coli, Pseudomonas Putida*, and *Pseudomonas Aeruginosa*," *Basic Life Sci.*, 1985, 30:6S7-662.

Makrides, S.C., "Strategies for Achieving High-Level Expression of Genes in *Escherichia coli*," *Microbiol. Rev.*, 1996, 60:512-538.

Morrison, "Transformation in *Escherichia coli*: Cryogenic Preservation of Competent Cells," *Journ. Bacteriology*, 1977, 132:349-351.

Mukhija et al., "High-level production and one-step purification of biologically active human growth hormone in *Escherichia coli*," *Gene*, 1995, 165(2):303-306.

Mukhopadhyay et al., "Construction of a Stable Shuttle Vector for High-Frequency Transformation in *Psendornona syringae pv. syringae*," *Journ. Bacteriology*, Jan. 1990, 172(1):477-480.

Nagahari and Sakaguchi, "RS171010 Plasmid as a Potentially Useful Vector in *Pseudomonas* Species," *Journ. Bacteriology*, Mar. 1978, 133(3):1527-1529.

Nieto et al., "Cloning vectors, derived from a naturally occurring plasmid of *Pseudomonas savastanoi*, specifically tailored for genetic manipulations in *Pseudomonas*," *Gene*, Mar. 1, 1990, 87(1):145-149.

Olekhnovich and Fomichev, "Controlled-expression shuttle vector for pseudomonads based on the trpIBA genes of *Pseudomonas putida*," *Gene*, Mar. 11, 1994, 140(1):63-65.

Patra et al., "Optimization of Inclusion Body Solubilization and Renaturation of Recombinant Human Growth Hormone from *Escheriehia coli*," *Protein Expr Purif*, 2000, 18(2):182-192.

Pearson, W.R., "Using the FASTA Program to Search Protein and DNA Sequence Databases," Chapter 26, *Methods Molec. Biol.*, 1994, 24:307-331.

Pearson, W,R., "Using the FASTA Program to Search Protein and DNA Sequence Databases," Chapter 29, *Methods Molec. Biol.*, 1994, 25:365-389.

Pearson and Lipman, "Improved tools for biological sequence comparison," *Proc. Nat'l Acad. Sci.*, Apr. 1988, 85:2444-2448.

Schweizer et al., "Vector Design and Development of Host Systems for *Pseudomonas*," *Genet. Eng.*, 2001, 23:69-81, Kluwer Academic/Plenum Pub.

\* cited by examiner

LacI →
(MB214 form)

LacI →

PROTEIN EXPRESSION SYSTEMS

CROSS REFERENCE TO RELATED APPLICATIONS

This application is a divisional of U.S. application Ser. No. 10/994,138, filed Nov. 19, 2004, now abandoned which claims the benefit of U.S. Provisional patent application Ser. No. 60/523,420, filed Nov. 19, 2003, entitled "Improved Pseudomonas Expression Systems with Auxotrophic Selection Markers," and U.S. Provisional patent application 60/537,147 filed Jan. 16, 2004, and entitled "Bacterial Expression Systems with Improved Repression," each of which is hereby incorporated in its entirety by reference herein.

REFERENCE TO A SEQUENCE LISTING SUBMITTED AS A TEXT FILE VIA EFS-WEB

The instant application contains a Sequence Listing which has been submitted as a text file via EFS-Web in compliance with the American Standard Code for Information Interchange (ASCII), and is incorporated herein by reference in its entirety. Said ASCII copy, created on Jan. 17, 2012, is named 38194705.txt and is 41,154 bytes in size.

FIELD OF THE INVENTION

The present invention provides an improved expression system for the production of recombinant polypeptides utilizing auxotrophic selectable markers. In addition, the present invention provides improved recombinant protein production in host cells through the improved regulation of expression.

BACKGROUND OF THE INVENTION

The use of bacterial cells to produce protein based therapeutics is increasing in commercial importance. One of the goals in developing a bacterial expression system is the production of high quality target polypeptides quickly, efficiently, and abundantly. An ideal host cell for such an expression system would be able to efficiently utilize a carbon source for the production of a target polypeptide, quickly grow to high cell densities in a fermentation reaction, express the target polypeptide only when induced, and grow on a medium that is devoid of regulatory and environmental concerns.

There are many hurdles to the creation of a superior host cell. First, in order to produce a recombinant polypeptide, an expression vector encoding the target protein must be inserted into the host cell. Many bacteria are capable of reverting back into an untransformed state, wherein the expression vector is eliminated from the host. Such revertants can decrease the fermentation efficiency of the production of the desired recombinant polypeptide.

Expression vectors encoding a target peptide typically include a selection marker in the vector. Often, the selection marker is a gene whose product is required for survival during the fermentation process. Host cells lacking the selection marker, such as revertants, are unable to survive. The use of selection markers during the fermentation process is intended to ensure that only bacteria containing the expression vector survive, eliminating competition between the revertants and transformants and reducing the efficiency of fermentation.

The most commonly used selection markers are antibiotic resistance genes. Host cells are grown in a medium supplemented with an antibiotic capable of being degraded by the selected antibiotic resistance gene product. Cells that do not contain the expression vector with the antibiotic resistance gene are killed by the antibiotic. Typical antibiotic resistance genes include tetracycline, neomycin, kanamycin, and ampicillin. The presence of antibiotic resistance genes in a bacterial host cell, however, presents environmental, regulatory, and commercial problems. For example, antibiotic resistance gene-containing products (and products produced by the use of antibiotic resistance gene) have been identified as potential biosafety risks for environmental, human, and animal health. For example, see M. Droge et al., Horizontal Gene Transfer as a Biosafety issue: A natural phenomenon of public concern, J. Biotechnology. 64(1): 75-90 (17 Sep. 1998); Gallagher, D. M., and D. P. Sinn. 1983. Penicillin-induced anaphylaxis in a patient under hypotensive anaesthesia. Oral Surg. Oral Med. Oral Pathol. 56:361-364; Jorro, G., C. Morales, J. V. Braso, and A. Pelaez. 1996. Anaphylaxis to erythromycin. Ann. Allergy Asthma Immunol. 77:456-458; F. Gebhard & K. Smalla, Transformation of Acinetobacter sp. strain BD413 by transgenic sugar beet DNA, Appl. & Environ. Microbiol. 64(4):1550-54 (April 1998); T. Hoffmann et al., Foreign DNA sequences are received by a wild type strain of *Aspergillus niger* after co-culture with transgenic higher plants, Curr. Genet. 27(1): 70-76 (December 1994); DK Mercer et al., Fate of free DNA and transformation of the oral bacterium Streptococcus gordonoii DL1 by plasmid DNA in human saliva, Appl. & Environ. Microbiol. 65(1):6-10 (January 1999); R. Schubert et al., Foreign (M13) DNA ingested by mice reaches peripheral leukocytes, spleen, and liver via the intestinal wall mucosa and can be covalently linked to mouse DNA, PNAS USA 94:961-66 (Feb. 4, 1997); and AA Salyers, Gene transfer in the mammalian intestinal tract, Curr. Opin. in Biotechnol. 4(3):294-98 (June 1993).

As a result of these concerns, many governmental food, drug, health, and environmental regulatory agencies, as well as many end users, require that antibiotic resistance gene nucleic acid be removed from products or be absent from organisms for use in commerce. In addition, evidence demonstrating clearance of the selection antibiotics from the final product must be provided in order to secure regulatory clearance. The United Kingdom, Canada, France, the European Community, and the United States have all addressed the use of antibiotic resistance genes in foods, animal feeds, drugs and drug production, including recombinant drug production. Clearance of these agents, and especially demonstrating such clearance, is expensive, time consuming, and often only minimally effective.

Because of the concerns inherent in the use of antibiotic resistance genes for selection in the production of recombinant polypeptides, alternative selection methods have been examined.

Auxotrophic Selection Markers

Auxotrophic selection markers have been utilized as an alternative to antibiotic selection in some systems. For example, auxotrophic markers have been widely utilized in yeast, due largely to the inefficiency of antibiotic resistance selection markers in these host cells. See, for example, J T Pronk, (2002) "Auxotrophic yeast strains in fundamental and applied research," App. & Envirn. Micro. 68(5): 2095-2100; Boeke et al., (1984) "A positive selection for mutants lacking orotodine-5'-phosphate decarboxylase activity in yeast; 5-fluoro-orotic acid resistance," Mol. Gen. Genet. 197: 345-346; Botstein & Davis, (1982) "Principles and practice of recombinant DNA research with yeast," p. 607-636, in J N Strathern, E W Jones. And J R Broach (ed.), The molecular biology of the yeast *Saccharomyces cerevisiae*, Metabolism and gene expression, Cold Spring Harbor Laboratory Press, Cold Spring Harbor, N.Y.; Cost & Boeke, (1996) "A useful colony color phenotype associated with the yeast selectable/counter selectable marker MET15,"Yeast 12: 939-941. However, yeast expression systems due not provide the potential speed and efficiency for producing target proteins that bacterial systems do.

Auxotrophic marker selection in bacteria has also previously been described. See, for example, U.S. Pat. Nos. 4,920,048, 5,691,185, 6,291,245, 6,413,768, 6,752,994, Struhl et al. (1976) PNAS USA 73; 1471-1475; MacCormick, C. A., et al., (1995) "Construction of a food-grade host/vector system for *Lactococcus lactis* based on the lactose operon," FEMS Microbiol. Lett. 127:105-109; Dickely et al. (1995), "Isolation of *Lactococcus lactis* nonsense suppressors and construction of a food-grade cloning vector," Mol. Microbiol. 15:839-847; Sørensen et al., (2000) "A food-grade cloning system for industrial strains of *Lactococcus lactis,"* Appl. Environ. Microbiol. 66:1253-1258; Fiedler & Skerra, (2001) "proBA complementation of an auxotrophic *E. coli* strain improves plasmid stability and expression yield during fermenter production of a recombinant antibody fragment," Gene 274: 111-118.

The use of auxotrophic selection markers in the previously described commercial scale bacterial fermentation systems has drawbacks that limit their use. A major drawback, as noted in U.S. Pat. No. 6,413,768, is that nutritional auxotrophic selection marker systems generally suffer from cross feeding. The term cross feeding refers to the ability of a first cell, auxotrophic for a particular metabolite, to survive in the absence of the metabolite by obtaining its supply of that metabolite from its environment, and typically, from the medium for which the cell is auxotrophic by utilizing excreted intermediates of the metabolite, the metabolite itself, or a prototrophic enabling molecule produced by a second cell, prototrophic for the metabolite absent from the medium. See also GR Barker et al., Biochem. J. 157(1):221-27 (1976) (cross feeding of thymine in *E. coli*): T J Kerr & G J Tritz, J. Bact. 115(3):982-86 (September 1973) (cross feeding of NAD in *E. coli* auxotrophic for NAD synthesis); G A Sprenger et al., FEMS Microbiol. Lett. 37(3):299-304 (1986) (selection of nalidixic acid to avoid the cross feeding problem).

Because cross feeding allows revertant bacteria to survive, cross feeding decreases the overall capacity of the fermentation process to produce the desired product at efficient and maximized levels due to the presence of fewer target protein producing host cells.

Expression Vector Control

Another hurdle to the creation of the ideal host cell is the inefficient and low level production of target polypeptides in the fermentation process. Controlling expression of the target protein until optimal host cell densities and fermentation conditions are reached allows for a more efficient and larger yield of polypeptide. The reasons for this are several fold, including a more efficient utilization of a particular carbon source and the reduction of extended metabolic stresses on the host cell.

In many cases, however, repression of expression of the target protein during cell growth can be imperfect, resulting in a significant amount of expression prior to the particular induction phase. This "leaky" repression results in host cell stress, inefficient utilization of carbon source due to metabolic energy being diverted from normal cell growth to transgene, and a delay in reaching optimal cell density induction points, resulting in a more lengthy and costly fermentation run, and often, a reduced yield of the target protein.

Therefore, it is an object of the present invention to provide an improved expression system for the production of target proteins, wherein the production is efficient, regulatable, and performed in a medium that minimizes of regulatory and environmental concerns.

It is another object of the present invention to provide organisms for use as host cells in an improved expression system for the production of target proteins.

It is still another object of the present invention to provide processes for the improved production of target proteins.

It is yet another object of the present invention to provide novel constructs and nucleic acids for use in an improved expression system for the production of target proteins.

SUMMARY OF THE INVENTION

It has been discovered that bacterial protein production can be improved by selecting as a host cell a Pseudomonad organism that is capable of non-antibiotic resistant, auxotrophic selection, and/or contains a chromosomal insert of a lacI gene or derivative.

Specifically, it has been discovered that the Pseudomonad organism *Pseudomonas fluorescens* is particularly well suited for this purpose. To this end, it has been surprisingly discovered that *Pseudomonas fluorescens* does not exhibit adverse cross feeding inhibition under auxotrophic selection during the high-cell density fermentation of recombinant polypeptides. Such a discovery allows for the use of auxotrophic *Pseudomonas fluorescens* as host cells in the efficient production of high levels of recombinant polypeptides, overcoming the drawbacks inherent with the use of antibiotic resistance selection markers and the problems of auxotrophic cross feeding present in other bacterial expression systems.

It has also been surprisingly discovered that the use of a LacI-encoding gene other than as part of a whole or truncated Plac-lacI-lacZYA operon in Pseudomonads surprisingly resulted in substantially improved repression of pre-induction recombinant protein expression, higher cell densities in commercial-scale fermentation, and higher yields of the desired product in comparison with previously taught lacI-lacZYA Pseudomonad chromosomal insertion (U.S. Pat. No. 5,169,760). This lacI insertion is as effective in repressing Plac-Ptac family promoter-controlled transgenes as a multicopy plasmid encoding a LacI repressor protein in *Pseudomonas fluorescens*, thereby eliminating the need to maintain a separate plasmid encoding a LacI repressor protein in the cell and reducing potential production inefficiencies caused by such maintenance.

It has also been discovery that the use of dual lac operator sequences provides superior repression of recombinant protein expression prior to induction without a concomitant reduction in subsequent induction yields in *Pseudomonas fluorescens*

Therefore, in one aspect of the present invention, Pseudomonad organisms are provided for use as host cells in the improved production of proteins.

In one embodiment, the Pseudomonad organisms have been genetically modified to induce an auxotrophy. In a particular embodiment, the Pseudomonad organism is *Pseudomonas fluorescens*. In one embodiment, the auxotrophy is a result of genetic modifications to at least one nitrogenous base compound biosynthesis gene, or at least one amino acid biosynthesis gene. In a further embodiment, the genetic modification is to a gene encoding an enzyme active in the uracil biosynthetic pathway, the thymidine biosynthetic pathway, or the proline biosynthetic pathway. In still a further embodiment, the genetic modification is to the pyrF gene encoding orotidine-5'-phosphate decarboxylase, the thyA gene encoding thymidylate synthase, or the proC gene encoding Δ$^1$-pyrroline-5-carboxylate reductase.

In another embodiment, the present invention provides Pseudomonad organisms that have been genetically modified to provide at least one copy of a LacI-encoding gene inserted into the genome, other than as part of the whole or truncated Plac-lacI-lacZYA operon. In a particular embodiment, the Pseudomonad host cell is *Pseudomonas fluorescens*. In one embodiment, the Pseudomonad contains a native *E. coli* lacI gene encoding the LacI repressor protein. In another embodiment, the Pseudomonad cell contains the lacI$^Q$ gene. In still another embodiment, the Pseudomonad cell contains the lacI$^{Q1}$ gene.

In another embodiment, a Pseudomonad organism is provided comprising a nucleic acid construct containing a nucleic acid comprising at least one lacO sequence involved in the repression of transgene expression. In a particular embodiment, the Pseudomonad host cell is *Pseudomonas fluorescens*. In one embodiment, the nucleic acid construct comprises more than one lacO sequence. In another embodiment, the nucleic acid construct comprises at least one, and preferably more than one, lacOid sequence. In one embodiment, the nucleic acid construct comprises a lacO sequence, or derivative thereof, located 3' of a Plac family promoter, and a lacO sequence, or derivative thereof, located 5' of a Plac family promoter. In a particular embodiment, the lacO derivative is a lacOid sequence.

In a further embodiment, the present invention provides Pseudomonad organisms that have been genetically modified to induce an auxotrophy and further modified to contain a chromosomal insertion of a native *E. coli* lacI gene, lacI$^Q$ gene, or lacI$^{Q1}$ gene other than as part of a whole or truncated Plac-lacI-lacZYA operon. In another embodiment, the Pseudomonad organism is further modified to contain a nucleic acid construct comprising at least one lacO sequence involved in the repression of transgene expression. In a particular embodiment, the Pseudomonad organism is a *Pseudomonas fluorescens*.

In another aspect of the present invention, nucleic acid sequences are provided for use in the improved production of proteins.

In one embodiment, nucleic acid sequences encoding prototrophy-restoring enzymes for use in an auxotrophic Pseudomonad host cells are provided. In a particular embodiment, nucleic acid sequences encoding nitrogenous base compound biosynthesis enzymes purified from the organism *Pseudomonas fluorescens* are provided. In one embodiment, nucleic acid sequences encoding the pyrF gene in *Pseudomonas fluorescens* is provided (SEQ. ID No.s 1 and 3). In another embodiment, a nucleic acid sequence encoding the thyA gene in *Pseudomonas fluorescens* is provided (SEQ. ID. No. 4). In still another embodiment, nucleic acid sequences encoding an amino acid biosynthetic compound purified from the organism *Pseudomonas fluorescens* are provided. In a particular embodiment, a nucleic acid sequence encoding the proC gene in *Pseudomonas fluorescens* is provided (SEQ. ID No.s 6 and 8).

In another aspect, the present invention produces novel amino acid sequences which are the products of the novel nucleic acid expression.

In still another aspect of the present invention, nucleic acid constructs are provided for use in the improved production of peptides.

In one embodiment, a nucleic acid construct for use in transforming a Pseudomonad host cell comprising a) a nucleic acid sequence encoding a recombinant polypeptide, and b) a nucleic acid sequence encoding a prototrophy-enabling enzyme is provided. In another embodiment, the nucleic acid construct further comprises c) a Plac-Ptac family promoter. In still another embodiment, the nucleic acid construct further comprises d) at least one lacO sequence, or derivative, 3' of a lac or tac family promoter. In yet another embodiment, the nucleic acid construct further comprises e) at least one lacO sequence, or derivative, 5' of a lac or tac family promoter. In one embodiment, the derivative lacO sequence can be a lacOid sequence. In a particular embodiment, the Pseudomonad organism is *Pseudomonas fluorescens*.

In one embodiment of the present invention, nucleic acid constructs are provided for use as expression vectors in Pseudomonad organisms comprising a) a nucleic acid sequence encoding a recombinant polypeptide, b) a Plac-Ptac family promoter, c) at least one lacO sequence, or derivative, 3' of a lac or tac family promoter, d) at least one lacO sequence, or derivative, 5' of a lac or tac family promoter. In one embodiment, the derivative lacO sequence can be a lacOid sequence. In one embodiment, the nucleic acid construct further comprises e) a prototrophy-enabling selection marker for use in an auxotrophic Pseudomonad cell. In a particular embodiment, the Pseudomonad organism is *Pseudomonas fluorescens*.

In another aspect of the present invention, modified cells are provided for use in the improved production of proteins.

In one embodiment, an auxotrophic Pseudomonad cell is provided that has a nucleic acid construct comprising i) a recombinant polypeptide, and ii) a prototrophy-enabling nucleic acid. In another embodiment, the nucleic acid construct further comprises iii) a Plac-Ptac family promoter. In still another embodiment, the nucleic acid construct further comprises iv) more than one lacO sequence. In one embodiment, the Pseudomonad is an auxotrophic *Pseudomonas fluorescens* cell. In a further embodiment, the invention further comprises auxotrophic Pseudomonad organisms, including *Pseudomonas fluorescens*, that have been further genetically modified to contain a chromosomal insertion of a native *E. coli* lacI gene, lacI$^Q$ gene, or lacI$^{Q1}$ gene other than as part of a whole or truncated Plac-lacI-lacZYA operon.

In another embodiment, a Pseudomonad cell is provided that comprises a lacI transgene, or derivative thereof, other than as part of a whole or truncated Plac-lacI-lacZYA operon, inserted into the chromosome, and b) a nucleic acid construct comprising i) a recombinant polypeptide, and ii) a Plac-Ptac family promoter. In still another embodiment, the nucleic acid construct further comprises iii), at least one lacO sequence, and preferably, more than one lacO sequence. In one embodiment, the lacO sequence is a lacOid sequence.

In one embodiment, the Pseudomonad has been further modified to induce auxotrophy. In one embodiment, the Pseudomonad cell is a *Pseudomonas fluorescens*.

In one aspect of the present invention, processes of expressing recombinant polypeptides for use in improved protein production are provided.

In one embodiment, the process provides expression of a nucleic acid construct comprising nucleic acids encoding a) a recombinant polypeptide, and b) a prototrophy-restoring enzyme in a Pseudomonad that is auxotrophic for at least one metabolite. In an alternative embodiment, the Pseudomonad is auxotrophic for more than one metabolite. In one embodiment, the Pseudomonad is a *Pseudomonas fluorescens* cell. In a particular embodiment, a recombinant polypeptide is expressed in a Pseudomonad that is auxotrophic for a metabolite, or combination of metabolites, selected from the group consisting of a nitrogenous base compound and an amino acid. In a more particular embodiment, recombinant polypeptides are expressed in a Pseudomonad that is auxotrophic for a metabolite selected from the group consisting of uracil, proline, and thymidine. In another embodiment, the auxotrophy can be generated by the knock-out of the host pyrF, proC, or thyA gene, respectively. An alternative embodiment, recombinant polypeptides are expressed in an auxotrophic Pseudomonad cell that has been genetically modified through the insertion of a native E. coli lacI gene, lacI$^Q$ gene, or lacI$^{Q1}$ gene, other than as part of the PlacI-lacI-lacZYA operon, into the host cell's chromosome. In one particular embodiment, the vector containing the recombinant polypeptide expressed in the auxotroph comprises at least one lacOid operator sequences. In one particular embodiment, the vector containing the recombinant polypeptide expressed in the auxotrophic host cell comprises at least two lac operator sequences, or derivatives thereof. In still a further embodiment, the recombinant polypeptide is driven by a Plac family promoter.

In another embodiment, the process involves the use of Pseudomonad host cells that have been genetically modified to provide at least one copy of a LacI encoding gene inserted into the Pseudomonad host cell's genome, wherein the lacI encoding gene is other than as part of the PlacI-lacI-lacZYA operon. In one embodiment, the gene encoding the Lac repressor protein is identical to that of native E. coli lacI gene. In another embodiment, the gene encoding the Lac repressor protein is the lacI$^Q$ gene. In still another embodiment, the gene encoding the Lac repressor protein is the lacI$^{Q1}$ gene. In a particular embodiment, the Pseudomonad host cell is *Pseudomonas fluorescens*. In another embodiment, the Pseudomonad is further genetically modified to produce an auxotrophic cell. In another embodiment, the process produces recombinant polypeptide levels of at least about 3 g/L, 4 g/L, 5 g/L 6 g/L, 7 g/L, 8 g/L, 9 g/L or at least about 10 g/L. In another embodiment, the recombinant polypeptide is expressed in levels of between 3 g/L and 100 g/L.

DETAILED DESCRIPTION OF THE INVENTION

Figure 1:
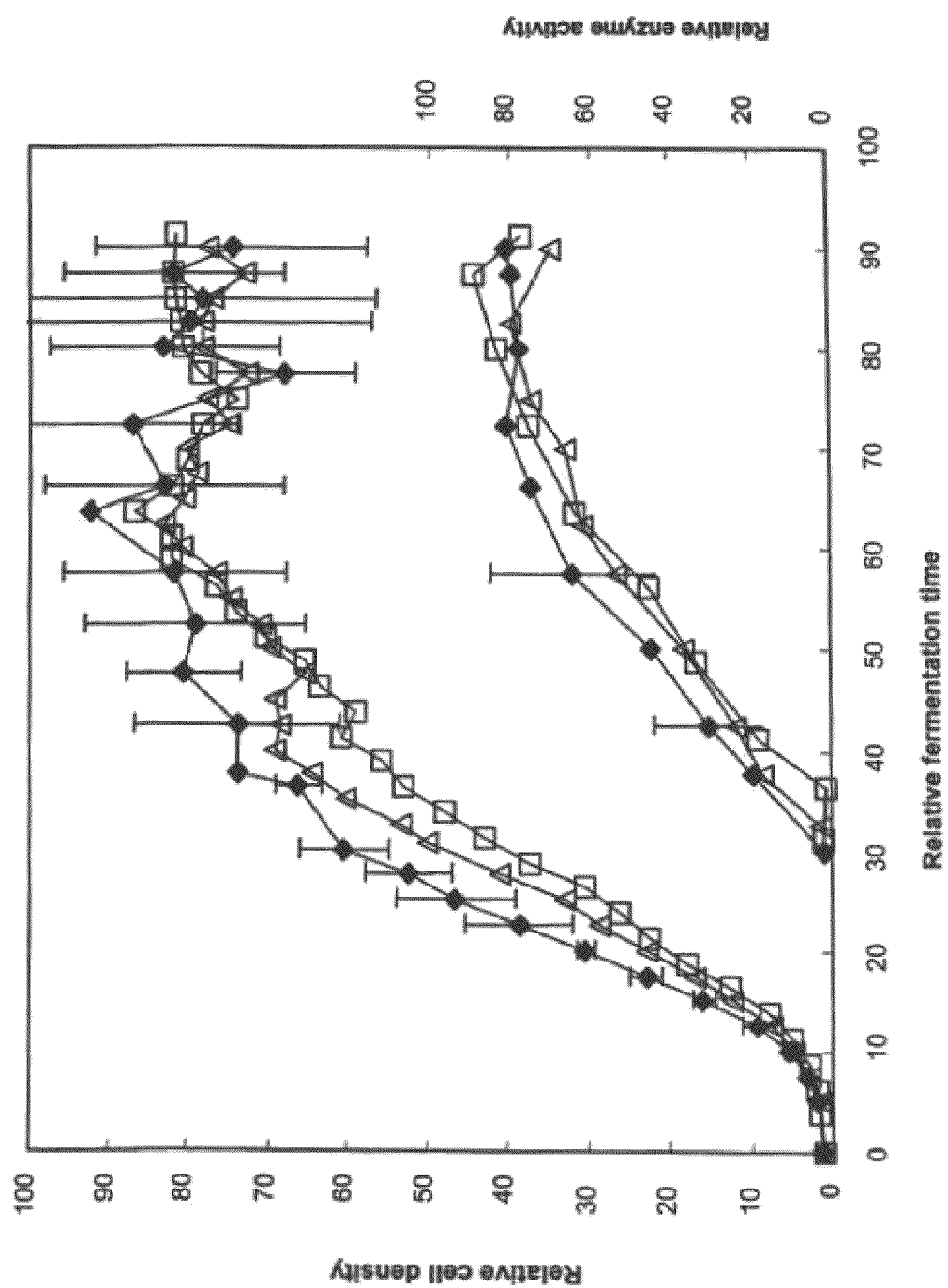
FIG. 1 represents a comparison of the performance of P. fluorescens dual-plasmid expression systems using a pyrF marker (Δ and □) against the performance of P. fluorescens dual-plasmid expression systems using only antibiotic resistance markers (♦). All data shown are averages of 9-multiple, representative 20-L fermentations, with IPTG being added to induce target enzyme expression during mid-exponential phase. The upper set of three curves presents relative cell density data, which is read with reference to the left vertical axis. The lower set of three curves presents relative enzyme activity data for the target enzyme produced in the corresponding fermentations, and is read with reference to the right vertical axis. ♦—P. fluorescens containing pMYC plasmid having a tac promoter-controlled target enzyme expression cassette and a tetracycline resistance marker gene and containing a pCN plasmid having a lacI repressor expression cassette and a kanamycin resistance marker gene. Variance bars shown are for these data points (n=4), and represent the normal variance typically observed for this expression system among different fermentation runs. Δ—P. fluorescens strain with inactivated genomic pyrF containing pMYC plasmid having a tac promoter-controlled target enzyme expression cassette and a pyrF auxotrophic marker gene and containing pCN plasmid having a lacI repressor expression cassette and a kanamycin resistance marker gene. □—P. fluorescens strain with inactivated genomic pyrF and proC containing pMYC plasmid having a tac promoter-controlled target enzyme expression cassette and a pyrF auxotrophic marker gene and containing pCN plasmid having a lacI repressor expression cassette and a proC auxotrophic marker gene.

In one embodiment, the Pseudomonad organisms have been genetically modified to induce an auxotrophy. In a particular embodiment, the Pseudomonad organism is *Pseudomonas fluorescens*. In one embodiment, the auxotrophy is a result of genetic modifications to at least one nitrogenous base compound biosynthesis gene, or at least one amino acid biosynthesis gene. In a further embodiment, the genetic modification is to a gene encoding an enzyme active in the uracil biosynthetic pathway, the thymidine biosynthetic pathway, or the proline biosynthetic pathway. In still a further embodiment, the genetic modification is to the pyrF gene encoding orotidine-5'-phosphate decarboxylase, the thyA gene encoding thymidylate synthase, or the proC gene encoding $\Delta^1$-pyrroline-5-carboxylate reductase.

In another embodiment, the present invention provides Pseudomonad organisms that have been genetically modified to provide at least one copy of a LacI-encoding gene inserted into the genome, other than as part of the PlacI-lacI-lacZYA operon. In a particular embodiment, the Pseudomonad host cell is *Pseudomonas fluorescens*. In one embodiment, the Pseudomonad contains a native E. coli lacI gene encoding the LacI repressor protein. In another embodiment, the Pseudomonad cell contains the lacI$^Q$ gene. In still another embodiment, the Pseudomonad cell contains the lacI$^{Q1}$ gene.

In another embodiment, a Pseudomonad organism is provided comprising a nucleic acid construct containing a nucleic acid comprising at least one lacO sequence involved in the repression of transgene expression. In a particular embodiment, the Pseudomonad host cell is *Pseudomonad fluorescens*. In one embodiment, the nucleic acid construct comprises more than one lacO sequence. In another embodiment, the nucleic acid construct comprises at least one, and preferably more than one, lacOid sequence. In one embodiment, the nucleic acid construct comprises a lacO sequence, or derivative thereof, located 3' of a Plac family promoter, and a lacO sequence, or derivative thereof, located 5' of a Plac family promoter. In a particular embodiment, the lacO derivative is a lacOid sequence.

In a further embodiment, the present invention provides Pseudomonad organisms that have been genetically modified to induce an auxotrophy and further modified to contain a chromosomal insertion of a native *E. coli* lacI gene, lacI Q gene, or lacIQ1 gene other than as part of a whole or truncated Plac-lacI-lacZYA operon. In another embodiment, the Pseudomonad organism is further modified to contain a nucleic acid construct comprising at least one lacO sequence involved in the repression of transgene expression. In a particular embodiment, the Pseudomonad organism is a *Pseudomonas fluorescens*.

The host cell provided by the present invention for use in an expression system producing recombinant polypeptides can be selected from the "Pseudomonads and closely related bacteria" or from a Subgroup thereof, as defined below. In one embodiment, the host cell is selected from the genus *Pseudomonas*. In a particular embodiment, the particular species of *Pseudomonas* is *P. fluorescens*. In a particular embodiment, the host cell is *Pseudomonas fluorescens* biotype A or biovar I.

Definitions

The term "isolated" refers to nucleic acid, protein, or peptide that is substantially or essentially free from other material components, for example, which can be cellular components.

The term "fragment" means a portion or partial sequence of a nucleotide, protein, or peptide sequence.

As used herein, the term "percent total cell protein" means the amount of protein or peptide in the host cell as a percentage of aggregate cellular protein.

The term "operably attached," as used herein, refers to any configuration in which the transcriptional and any translational regulatory elements are covalently attached to the encoding sequence in such disposition(s), relative to the coding sequence, that in and by action of the host cell, the regulatory elements can direct the expression of the coding sequence The term "auxotrophic," as used herein, refers to a cell which has been modified to eliminate or reduce its ability to produce a specific substance required for growth and metabolism.

As used herein, the term "percent total cell protein" means a measure of the fraction of total cell protein that represents the relative amount of a given protein expressed by the cell.

The term "prototrophy," as used herein, refers to a cell that is capable of producing a specific substance required for growth and metabolism.

As used herein, the term "homologous" or means either i) a protein or peptide that has an amino acid sequence that is substantially similar (i.e., at least 70, 75, 80, 85, 90, 95, or 98%) to the sequence of a given original protein or peptide and that retains a desired function of the original protein or peptide or ii) a nucleic acid that has a sequence that is substantially similar (i.e., at least 70, 75, 80, 5, 90, 95, or 98%) to the sequence of a given nucleic acid and that retains a desired function of the original nucleic acid sequence. In all of the embodiments of this invention and disclosure, any disclosed protein, peptide or nucleic acid can be substituted with a homologous or substantially homologous protein, peptide or nucleic acid that retains a desired function. In all of the embodiments of this invention and disclosure, when any nucleic acid is disclosed, it should be assumed that the invention also includes all nucleic acids that hybridize to the disclosed nucleic acid.

In one non-limiting embodiment, the non-identical amino acid sequence of the homologous polypeptide can be amino acids that are members of any one of the 15 conservative or semi-conservative groups shown in Table 1.

TABLE 1

SIMILAR AMINO ACID SUBSTITUTION GROUPS

| Conservative Groups (8) | Semi-Conservative Groups (7) |
|---|---|
| Arg, Lys | Arg, Lys, His |
| Asp, Glu | Asn, Asp, Glu, Gln |
| Asn, Gln | |
| Ile, Leu, Val | Ile, Leu, Val, Met, Phe |
| Ala, Gly | Ala, Gly, Pro, Ser, Thr |
| Ser, Thr | Ser, Thr, Tyr |
| Phe, Tyr | Phe, Trp, Tyr |
| Cys (non-cystine), Ser | Cys (non-cystine), Ser, Thr |

Amino acid sequences provided herein are represented by the following abbreviations:

| A | Ala | alanine |
|---|---|---|
| P | Pro | proline |
| B | | aspartate or asparagine |
| Q | Gln | glutamine |
| C | Cys | cysteine |
| R | Arg | arginine |
| D | Asp | aspartate |
| S | Ser | serine |
| E | Glu | glutamate |
| T | Thr | threonine |
| F | Phe | phenylalanine |
| G | Gly | glycine |
| V | Val | valine |
| H | His | histidine |
| W | Trp | tryptophan |
| I | Ile | isoleucine |
| Y | Tyr | tyrosine |
| Z | | glutamate or glutamine |
| K | Lys | lysine |
| L | Leu | leucine |
| M | Met | methionine |
| N | Asn | asparagine |

I. Selection of Pseudomonads and Related Bacteria as Host Cells

The present invention provides the use of Pseudomonads and related bacteria as host cells in the improved production of proteins.

Auxotrophic Selection Efficiency

It has been discovered that Pseudomonads have the ability to utilize auxotrophic selection markers for the maintenance of protein expressing plasmids without the drawbacks typically associated with other systems, such as plasmid instability and cross-feeding.

Auxotrophic markers, in other host cell systems, are not always sufficient to maintain plasmids in every cell, especially during fermentations where loss of the plasmid may give plasmid-less cells a selective advantage, resulting in the accumulation of a large fraction of nonproductive cells, reducing product formation. Such revertant strains are especially troublesome if they have the ability to cross-feed the auxotrophic metabolite from prototrophic enabled bacteria. For example, use of the trp operon on a plasmid in an *E. coli* tryptophan auxotroph was not sufficient to prevent a large proportion of plasmid-less cells from accumulating, until combined with the valS gene (encoding valyl t-RNA synthetase) in a valS$^{ts}$ host (Skogman, S. G.; Nilsson, J., Temperature-dependent retention of a tryptophan-operon-bearing plasmid in *Escherichia coli*. Gene 1984, 31, (1-3), 117-22.) Presumably, the cells containing the trp operon on a plasmid secreted enough tryptophan or related molecules to allow growth of plasmid-less cells. Likewise, using the LEU2 gene on a xylitol-reductase production plasmid in leu2 mutant yeast resulted in plasmid loss; up to 80% of a fed-batch culture was made up of cells without a production plasmid, because leucine was secreted by plasmid-containing cells into the broth (Meinander, N. Q.; Hahn-Haegerdal, B., Fed-batch xylitol production with two recombinant *Saccharomyces cerevisiae* strains expressing XYL1 at different levels, using glucose as a cosubstrate: a comparison of production parameters and strain stability. *Biotechnology and Bioengineering* 1997, 54, (4), 391-399).

It has been discovered that *Pseudomonas fluorescens* (Pf) does not exhibit the inherent problems associated with cross-feeding observed in other host cell systems, for example, *E. coli* and yeast. While not wanting to be bound by any particular theory, it is thought that auxotrophic *Pseudomonas fluorescens* is a particularly suitable organism for use as a host cell because of the observed inability of a Pf auxotrophic cell to out compete a auxotrophic cell containing a prototrophic-enabling plasmid on a supplemented medium that contains the auxotrophic metabolite, indicating an innate difficulty of an Pf auxotroph to import the required metabolite. Because of this, Pf auxotrophic cells that lose the selection marker plasmid do not gain a selective advantage over Pf auxotrophic cells containing the selection marker, even in the presence of a supplemental metabolite, greatly reducing any potential effects of cross-feeding. Because of the reduced effects of cross-feeding, production yields of the recombinant polypeptide in a fermentation run are not reduced due to the presence of non-recombinant polypeptide producing cells.

LacI Insert

It has been discovered that Pseudomonads are able to use a single-copy lacI transgene, other than as part of a whole or truncated Plac-lacI-lacZYA operon, chromosomal insert to effectively repress protein expression until induction.

Transcription initiation from regulated promoters by RNA polymerase is activated or deactivated by the binding or releasing of a regulatory protein. Thus, regulated promoters include those that participate in negative control (i.e. repressible promoters), wherein the gene encoding the target polypeptide of interest is expressed only when the promoter is free of the regulator protein (i.e. a "repressor" protein), and those that participate in positive control, wherein the gene is expressed only when the promoter is bound by the regulator protein (i.e. an "activator" protein).

One of the most common classes of repressible promoters used in bacterial expression systems is the family of Plac-based promoters. The family of Plac-based promoters originates with the native *E. coli* lactose operon, referred to as the "lac" operon, also symbolized as "lacZYA," the expression of which is regulated by the expression product of the lacI gene. The native *E. coli* structure of the operon is "PlacI-lacI-PlacZ-lacZYA," wherein the native *E. coli* Plac promoter is represented by "PlacZ" (also called "PlacZYA"). "PlacI" represents the native promoter for the lacI gene, and "lacI" represents the gene encoding the lac repressor, i.e. the LacI protein. "lacZYA" represents the operon encoding the lactose utilization pathway.

The LacI-regulated promoters include, among others, the native *E. coli* lactose operon promoter ("Plac"). In addition, improved mutants have also been discovered, as have intra promoter hybrids of Plac, such as the "Ptac" promoter, "Ptrc" promoter, and the "PtacII" promoters. The Ptac promoter in *E. coli*, for example, is 3-fold stronger than the Plac promoter when fully derepressed. Therefore, it is frequently used for promoting high level regulated gene expression in *E. coli*. However, while the Plac promoter is 1,000-fold repressed by LacI, while the Plac promoter is only 50-fold repressed under similar conditions (Lanzer, M. & H. Bujard. 1988. Proc. Natl. Acad. Sci. USA. 85:8973). Repression of the *E. coli* Ptac promoter or other lac related promoters, depends upon the concentration of the repressor, LacI. (De Boer, et al., 1983. Proc. Natl. Acad. Sci. USA. 78:21-25). As set forth above, release from repression can occur through the addition of an inducer which reduces the affinity of the repressor for its specific DNA binding site, in this case, the lac operator (lacO). Alternatively, a reduction in the concentration of the repressor relative to the molar concentration of specific DNA binding sites on the plasmid can also derepress the promoter. If the lacI gene is located on a high copy number cloning plasmid, then a large amount of inducer is required to initiate expression because of the large amount of repressor produced in such a system.

In commercial production systems, the lac repressor is typically encoded by a gene whose expression is constitutive, i.e. non-regulated, thus providing an intracellular environment in which the desired transgene, encoding the desired target protein, is repressed until a desired host cell biomass or cell density is achieved. At that time, a quantity of a small molecule known as an inducer whose presence is effective to dissociate the repressor from the transgene, is added to the cell culture and taken up by the host cell, thereby permitting transcription of the transgene. In the case of lac repressor proteins, the inducer can be lactose or a non-metabolized, gratuitous inducer such as isopropyl-beta-D-thio-galactoside ("IPTG"). The selected point in time at which the inducer is to be added is referred to as the "induction phase."

A variety of lac repressor genes have been identified as useful for the repression of Plac family promoters present on recombinant polypeptide expression vectors. These include the native *E. coli* lacI gene and/or by variants thereof, including the lacI$^Q$ and lacI$^{Q1}$ genes that encode the same LacI protein, but at a higher expression level. For example, the lacI$^Q$ mutation is a single CG to TA change at −35 of the promoter region of lacI (Calos, M. 1978. Nature 274:762) which causes a 10-fold increase in LacI expression in *E. coli* (Mueller-Hill, B., et al. 1968. Proc. Natl. Acad. Sci. USA. 59:1259). Wild-type *E. coli* cells have a concentration of LacI of 10$^{-8}$ M or about 10 molecules per cell, with 99% of the protein present as a tetramer (Fickert, R. & B. Mueller-Hill 1992. J. Mol. Biol. 226:59). Cells containing the lacI$^Q$ mutation contain about 100 molecules per cell or 10$^{-7}$ M LacI. As a result, a number of bacterial expression systems have been developed in which Plac family promoter controlled transgenes, resident in plasmids, are maintained in host cells expressing LacI proteins at different levels, thereby repressing the desired transgene until a chosen "induction phase" of cell growth.

In many cases, however, repression of expression of the target protein during cell growth can be imperfect, resulting in a significant amount of expression prior to the particular induction phase. This "leaky" repression results in host cell stress, inefficient utilization of carbon source due to metabolic energy being diverted from normal cell growth to transgene, and a delay in reaching optimal cell density induction points, resulting in a more lengthy and costly fermentation run, and often, a reduced yield of the target protein.

One common strategy for improving repression of Plac-family promoter-driven transgenes has been to place a lacI or a lacI$^Q$ gene on the plasmid bearing the Plac-family promoter-driven target gene (e.g. see MJR Stark in Gene 51:255-67 (1987) and E Amann et al. in Gene:301-15 (1988)). However, this often results in overproduction of the Lac repressor protein, which then requires use of an even higher inducer concentration to restore induction levels of the transgene to overcome the decrease in recombinant protein production. Moreover, the use of a second plasmid containing the lacI gene, separate from the plasmid containing the Plac-family promoter-driven target gene, requires the use of two different selection marker genes in order to maintain both plasmids in the expression host cell: one selection marker gene for each of the two different plasmids. The presence of the second selection marker gene, i.e. the selection marker gene for the second plasmid, in turn requires the use of either: 1) a separate antibiotic in the case of an antibiotic-resistance selection marker gene, which is costly and disadvantageous from a health/safety regulatory perspective; or 2) a separate metabolic deficiency in the host cell genome, in the case of an auxotrophic selection marker gene, which requires the additional work of mutating the host cell.

It has surprisingly been discovered that a lacI insertion, other than as part of a whole or truncated PlacI-lacI-lacZYA operon, is as effective in repressing Plac-Ptac family promoter-controlled transgenes as a multi-copy plasmid encoding a LacI repressor protein in Pseudomonas fluorescens. This surprising discovery eliminates the need to maintain a separate plasmid encoding a LacI repressor protein in the cell, or eliminates the need to define an additional auxotrophic selection marker, and further reduces the potential production inefficiencies caused by such maintenance of a lacI containing plasmid.

In a previous attempt to regulate transgene expression in Pseudomonas, an E. coli PlacI-lacI-lacZYA operon that has been deleted of the lacZ promoter region, but that retains the constitutive PlacI promoter, was chromosomally inserted (See U.S. Pat. No. 5,169,760). The deletion allows for constitutive expression of the gene products of the lac operon. However, the inserted operon contains the E. coli lacy gene, which encodes for the lactose transporter protein lactose permease. Lactose permease is capable of transporting lactose, or similar derivatives, into the host cell from the medium. The presence of lactose permease may lead to increased importation of lactose-like contaminants from the medium, ultimately resulting in derepression of the Plac family promoter prior to induction. Furthermore, expression of the lac operon lacZ, lacy, and lacA gene products may result in the inefficient dedication of carbon utilization resources to these products, resulting in increased metabolic stress on the cells, and delaying the establishment of a high cell density for induction. In addition, the larger lacI-lacZYA fusion operon may produce increased message instability compared to a lacI insert alone in a host cell.

It has been surprisingly discovered that the use of a LacI-encoding gene other than as part of a whole or truncated PlacI-lacI-lacZYA operon in Pseudomonads surprisingly resulted in substantially improved repression of pre-induction recombinant protein expression, higher cell densities in commercial-scale fermentation, and higher yields of the desired product in comparison with previously taught lacI-lacZYA Pseudomonad chromosomal insertion (U.S. Pat. No. 5,169,760).

Additional attempts to utilize derivative lacI genes, such as lacI$^Q$ and lacI$^{Q1}$, which are expressed at greater levels than lacI due to promoter modifications, have also been described. C G Glascock & M J Weickert describe E. coli strains in which a separate LacI protein-encoding gene was present in the chromosome of the host cell in an attempt to assess the level of control of a plasmid-borne Ptac-driven target gene. See C G Glascock & M J Weickert, "Using chromosomal lacI$^{Q1}$ to control expression of genes on high-copy number plasmids in Escherichia coli," Gene 223(1-2):221-31 (1998); See also WO 97/04110. Among the LacI protein-encoding genes tested were lacI, lacI$^Q$, and lac$^{Q1}$. The results obtained for the lacI gene and the lacI$^Q$ gene demonstrated inferior levels of repression of the Ptac-driven target gene when present on a high-copy number plasmid, resulting in substantial levels of pre-induction target gene expression. Only the high expressing lacI$^{Q1}$ gene provided sufficient repression in that system.

Such a strategy, however, has the potential to increase costs by increasing the amount of inducer required to sufficiently derepress the promoter at induction, and decreasing yields due to the inability of the inducer to sufficiently bind all of the constitutively expressed repressor protein.

Comparatively, it has surprisingly been discovered that a single-copy lacI chromosomal insert was sufficient to repress Plac-Ptac family promoter driven transgene expression. Such a discovery allows potential cost saving measures on the amount of inducer used, and provides additional flexibility in the development of Pseudomonas fluorescens as a host cell in the improved production of proteins.

Pseudomonas Organisms

Pseudomonads and closely related bacteria, as used herein, is co-extensive with the group defined herein as "Gram(−) Proteobacteria Subgroup 1." "Gram(−) Proteobacteria Subgroup 1" is more specifically defined as the group of Proteobacteria belonging to the families and/or genera described as falling within that taxonomic "Part" named "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 4 presents the families and genera of organisms listed in this taxonomic "Part."

TABLE 1

FAMILIES AND GENERA LISTED IN THE PART, "GRAM-NEGATIVE AEROBIC RODS AND COCCI" (IN BERGEY (1974))

| | |
|---|---|
| Family I. Pseudomonadaceae | Gluconobacter |
| | Pseudomonas |
| | Xanthomonas |
| | Zoogloea |
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Family V. Halobacteriaceae | Halobacterium |
| | Halococcus |

TABLE 1-continued

FAMILIES AND GENERA LISTED IN THE PART, "GRAM-NEGATIVE AEROBIC RODS AND COCCI" (IN BERGEY (1974))

| Other Genera | *Acetobacter* |
| --- | --- |
| | *Alcaligenes* |
| | *Bordetella* |
| | *Brucella* |
| | *Francisella* |
| | *Thermus* |

"Gram(−) Proteobacteria Subgroup 1" contains all Proteobacteria classified there under, as well as all Proteobacteria that would be classified according to the criteria used in forming that taxonomic "Part." As a result, "Gram(−) Proteobacteria Subgroup 1" excludes, e.g.: all Gram-positive bacteria; those Gram-negative bacteria, such as the Enterobacteriaceae, which fall under others of the 19 "Parts" of this Bergey (1974) taxonomy; the entire "Family V. Halobacteriaceae" of this Bergey (1974) "Part," which family has since been recognized as being a non-bacterial family of Archaea; and the genus, Thermus, listed within this Bergey (1974) "Part," which genus which has since been recognized as being a non-Proteobacterial genus of bacteria.

"Gram(−) Proteobacteria Subgroup 1" further includes those Proteobacteria belonging to (and previously called species of) the genera and families defined in this Bergey (1974) "Part," and which have since been given other Proteobacterial taxonomic names. In some cases, these re-namings resulted in the creation of entirely new Proteobacterial genera. For example, the genera *Acidovorax, Brevundimonas, Burkholderia, Hydrogenophaga, Oceanimonas, Ralstonia,* and *Stenotrophomonas,* were created by regrouping organisms belonging to (and previously called species of) the genus *Pseudomonas* as defined in Bergey (1974). Likewise, e.g., the genus *Sphingomonas* (and the genus *Blastomonas,* derived therefrom) was created by regrouping organisms belonging to (and previously called species of) the genus *Xanthomonas* as defined in Bergey (1974). Similarly, e.g., the genus *Acidomonas* was created by regrouping organisms belonging to (and previously called species of) the genus *Acetobacter* as defined in Bergey (1974). Such subsequently reassigned species are also included within "Gram(−) Proteobacteria Subgroup 1" as defined herein.

In other cases, Proteobacterial species falling within the genera and families defined in this Bergey (1974) "Part" were simply reclassified under other, existing genera of Proteobacteria. For example, in the case of the genus *Pseudomonas, Pseudomonas enalia* (ATCC 14393), *Pseudomonas nigfifaciens* (ATCC 19375), and *Pseudomonas putrefaciens* (ATCC 8071) have since been reclassified respectively as *Alteromonas haloplanktis, Alteromonas nigrifaciens,* and *Alteromonas putrefaciens.* Similarly, e.g., *Pseudomonas acidovorans* (ATCC 15668) and *Pseudomonas testosteroni* (ATCC 11996) have since been reclassified as *Comamonas acidovorans* and *Comamonas testosteroni,* respectively; and *Pseudomonas nigrifaciens* (ATCC 19375) and *Pseudomonas piscicida* (ATCC 15057) have since been reclassified respectively as *Pseudoalteromonas nigrifaciens* and *Pseudoalteromonas piscicida.* Such subsequently reassigned Proteobacterial species are also included within "Gram(−) Proteobacteria Subgroup 1" as defined herein.

"Gram(−) Proteobacteria Subgroup I" also includes Proteobacterial species that have since been discovered, or that have since been reclassified as belonging, within the Proteobacterial families and/or genera of this Bergey (1974) "Part."

In regard to Proteobacterial families, "Gram(−) Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram(−) Proteobacteria Subgroup 1" include: 1) *Azotobacter* group bacteria of the genus *Azorhizophilus;* 2) Pseudomonadaceae family bacteria of the genera Cellvibrio, Oligella, and Teredinibacter; 3) Rhizobiaceae family bacteria of the genera Chelatobacter, Ensifer, Liberibacter (also called "Candidatus Liberibacter"), and *Sinorhizobium;* and 4) Methylococcaceae family bacteria of the genera *Methylobacter, Methylocaldum, Methylomicrobium, Methylosarcina,* and *Methylosphaera.*

In one embodiment, the host cell is selected from "Gram(−) Proteobacteria Subgroup 1," as defined above.

In another embodiment, the host cell is selected from "Gram(−) Proteobacteria Subgroup 2." "Gram(−) Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): Acidomonas (2); *Acetobacter* (93); *Gluconobacter* (37); Brevundimonas (23); Beierinckia (13); Derxia (2); Brucella (4); *Agrobacterium* (79); Chelatobacter (2); Ensifer (3); Rhizobium (144); Sinorhizobium (24); Blastomonas (1); Sphingomonas (27); Alcaligenes (88); Bordetella (43); Burkholderia (73); Ralstonia (33); Acidovorax (20); Hydrogenophaga (9); Zoogloea (9); Methylobacter (2); Methylocaldum (1 at NCIMB); Methylococcus (2); Methylomicrobium (2); Methylomonas (9); Methylosarcina (1); Methylosphaera; Azomonas (9); Azorhizophilus (5); Azotobacter (64); Cellvibrio (3); Oligella (5); Pseudomonas (1139); Francisella (4); Xanthomonas (229); Stenotrophomonas (50); and Oceanimonas (4).

Exemplary host cell species of "Gram(−) Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonzii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas* fluorescens (ATCC 35858); Francisella tularensis (ATCC 6223); Stenotrophomonas maltophilia (ATCC 13637); Xanthomonas campestris (ATCC 33913); and Oceanimonas doudoroffii (ATCC 27123).

In another embodiment, the host cell is selected from "Gram(−) Proteobacteria Subgroup 3." "Gram(−) Proteobacteria Subgroup 3" is defined as the group of Proteobacteria of the following genera: Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; and Oceanimonas.

In another embodiment, the host cell is selected from "Gram(−) Proteobacteria Subgroup 4." "Gram(−) Proteobacteria Subgroup 4" is defined as the group of Proteobacteria of the following genera: Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; and Oceanimonas.

In an embodiment, the host cell is selected from "Gram(−) Proteobacteria Subgroup 5." "Gram(−) Proteobacteria Subgroup 5" is defined as the group of Proteobacteria of the following genera: Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; and Oceanimonas.

The host cell can be selected from "Gram(−) Proteobacteria Subgroup 6." "Gram(−) Proteobacteria Subgroup 6" is defined as the group of Proteobacteria of the following genera: Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas; and Oceanimonas.

The host cell can be selected from "Gram(−) Proteobacteria Subgroup 7." "Gram(−) Proteobacteria Subgroup 7" is defined as the group of Proteobacteria of the following genera: Azomonas; Azorhizophilus; Azotobacter; Cellvibrio; Oligelia; Pseudomonas; Teredinibacter; Stenotrophomonas; Xanthomonas; and Oceanimonas.

The host cell can be selected from "Gram(−) Proteobacteria Subgroup 8." "Gram(−) Proteobacteria Subgroup 8" is defined as the group of Proteobacteria of the following genera: Brevundimonas; Blastomonas; Sphingomonas; Burkholderia; Ralstonia; Acidovorax; Hydrogenophaga; Pseudomonas; Stenotrophomonas; Xanthomonas; and Oceanimonas.

The host cell can be selected from "Gram(−) Proteobacteria Subgroup 9." "Gram(−) Proteobacteria Subgroup 9" is defined as the group of Proteobacteria of the following genera: Brevundimonas; Burkholderia; Ralstonia; Acidovorax; Hydrogenophaga; Pseudomonas; Stenotrophomonas; and Oceanimonas.

The host cell can be selected from "Gram(−) Proteobacteria Subgroup 10." "Gram(−) Proteobacteria Subgroup 10" is defined as the group of Proteobacteria of the following genera: Burkholderia; Ralstonia; Pseudomonas; Stenotrophomonas; and Xanthomonas.

The host cell can be selected from "Gram(−) Proteobacteria Subgroup 11." "Gram(−) Proteobacteria Subgroup 11" is defined as the group of Proteobacteria of the genera: Pseudomonas; Stenotrophomonas; and Xanthomonas.

The host cell can be selected from "Gram(−) Proteobacteria Subgroup 12." "Gram(−) Proteobacteria Subgroup 12" is defined as the group of Proteobacteria of the following genera: Burkholderia; Ralstonia; Pseudomonas.

The host cell can be selected from "Gram(−) Proteobacteria Subgroup 13." "Gram(−) Proteobacteria Subgroup 13" is defined as the group of Proteobacteria of the following genera: Burkholderia; Ralstonia; Pseudomonas; and Xanthomonas.

The host cell can be selected from "Gram(−) Proteobacteria Subgroup 14." "Gram(−) Proteobacteria Subgroup 14" is defined as the group of Proteobacteria of the following genera: Pseudomonas and Xanthomonas.

The host cell can be selected from "Gram(−) Proteobacteria Subgroup 15." "Gram(−) Proteobacteria Subgroup 15" is defined as the group of Proteobacteria of the genus Pseudomonas.

The host cell can be selected from "Gram(−) Proteobacteria Subgroup 16." "Gram(−) Proteobacteria Subgroup 16" is defined as the group of Proteobacteria of the following Pseudomonas species (with the ATCC or other deposit numbers of exemplary strain(s) shown in parenthesis): Pseudomonas abietaniphila (ATCC 700689); Pseudomonas aeruginosa (ATCC 10145); Pseudomonas alcaligenes (ATCC 14909); Pseudomonas anguilliseptica (ATCC 33660); Pseudomonas citronellolis (ATCC 13674); Pseudomonas flavescens (ATCC 51555); Pseudomonas mendocina (ATCC 25411); Pseudomonas nitroreducens (ATCC 33634); Pseudomonas oleovorans (ATCC 8062); Pseudomonas pseudoalcaligenes (ATCC 17440); Pseudomonas resinovorans (ATCC 14235); Pseudomonas straminea (ATCC 33636); Pseudomonas agarici (ATCC 25941); Pseudomonas alcaliphila; Pseudomonas alginovora; Pseudomonas andersonii; Pseudomonas asplenii (ATCC 23835); Pseudomonas azelaica (ATCC 27162); Pseudomonas beijerinckii (ATCC 19372); Pseudomonas borealis; Pseudomonas boreopolis (ATCC 33662); Pseudomonas brassicacearum; Pseudomonas butanovora (ATCC 43655); Pseudomonas cellulosa (ATCC 55703); Pseudomonas aurantiaca (ATCC 33663); Pseudomonas chlororaphis (ATCC 9446, ATCC 13985, ATCC 17418, ATCC 17461); Pseudomonas fragi (ATCC 4973); Pseudomonas lundensis (ATCC 49968); Pseudomonas taetrolens (ATCC 4683); Pseudomonas cissicola (ATCC 33616); Pseudomonas coronafaciens; Pseudomonas diterpeniphila; Pseudomonas elongata (ATCC 10144); Pseudomonas flectens (ATCC 12775); Pseudomonas azotoformans; Pseudomonas brenneri; Pseudomonas cedrella; Pseudomonas corrugata (ATCC 29736); Pseudomonas extremorientalis; Pseudomonas fluorescens (ATCC 35858); Pseudomonas gessardii; Pseudomonas libanensis; Pseudomonas mandelii (ATCC 700871); Pseudomonas marginalis (ATCC 10844); Pseudomonas migulae; Pseudomonas mucidolens (ATCC 4685); Pseudomonas orientalis; Pseudomonas rhodesiae; Pseudomonas synxantha (ATCC 9890); Pseudomonas tolaasii (ATCC 33618); Pseudomonas veronii (ATCC 700474); Pseudomonas frederiksbergensis; Pseudomonas geniculata (ATCC 19374); Pseudomonas gingeri; Pseudomonas graminis; Pseudomonas grimontii; Pseudomonas halodenitrificans; Pseudomonas halophila; Pseudomonas hibiscicola (ATCC 19867); Pseudomonas hut-

*tiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas fulva* (ATCC 31418); *Pseudomonas monteilii* (ATCC 700476); *Pseudomonas mosselii; Pseudomonas oiyzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*.

The host cell can be selected from "Gram(−) Proteobacteria Subgroup 17." "Gram(−) Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

The host cell can be selected from "Gram(−) Proteobacteria Subgroup 18." "Gram(−) Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 orbiovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* PfO-1; *Pseudomonas fluorescens* Pf-5 (ATCC BAA477); *Pseudomonas fluorescens* SBW25; and *Pseudomonas fluorescens* subsp. *cellulosa* (NCIMB 10462).

The host cell can be selected from "Gram(−) Proteobacteria Subgroup 19." "Gram(−) Proteobacteria Subgroup 19" is defined as the group of all strains of *Pseudomonas fluorescens* biotype A. A particularly particular strain of this biotype is *P. fluorescens* strain MB 101 (see U.S. Pat. No. 5,169,760 to Wilcox), and derivatives thereof.

In one embodiment, the host cell is any of the Proteobacteria of the order Pseudomonadales. In a particular embodiment, the host cell is any of the Proteobacteria of the family Pseudomonadaceae.

In a particular embodiment, the host cell is selected from "Gram(−) Proteobacteria Subgroup 1." In a particular embodiment, the host cell is selected from "Gram(−) Proteobacteria Subgroup 2." In a particular embodiment, the host cell is selected from "Gram(−) Proteobacteria Subgroup 3." In a particular embodiment, the host cell is selected from "Gram(−) Proteobacteria Subgroup 5." In a particular embodiment, the host cell is selected from "Gram(−) Proteobacteria Subgroup 7." In a particular embodiment, the host cell is selected from "Gram(−) Proteobacteria Subgroup 12." In a particular embodiment, the host cell is selected from "Gram(−) Proteobacteria Subgroup 15." In a particular embodiment, the host cell is selected from "Gram(−) Proteobacteria Subgroup 17." In a particular embodiment, the host cell is selected from "Gram(−) Proteobacteria Subgroup 18." In a particular embodiment, the host cell is selected from "Gram(−) Proteobacteria Subgroup 19."

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [IEM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212 [PJ 832]; 215 [PJ 849]; 216 [PJ 885]; 267 [B-9]; 271 [B-1612]; 401 [C71A; IFO 15831; PJ 187]; NRRL B-3178 [4; IFO 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; N1; SC15208; BNL-WVC; NCTC 2583 [NCIB 8194]; H13; 1013 [ATCC 11251; CCEB 295]; IFO 3903; 1062; or Pf-5.

II. Auxotrophic Selection Markers

The present invention provides Pseudomonads and related cells that have been genetically modified to induce auxotrophy for at least one metabolite. The genetic modification can be to a gene or genes encoding an enzyme that is operative in a metabolic pathway, such as an anabolic biosynthetic pathway or catabolic utilization pathway. Preferably, the host cell has all operative genes encoding a given biocatalytic activity deleted or inactivated in order to ensure removal of the biocatalytic activity. In a particular embodiment, the Pseudomonad is a *Pseudomonas fluorescens* cell.

One or more than one metabolic activity may be selected for knock-out or replacement. In the case of native auxotrophy(ies), additional metabolic knockouts or replacements can be provided. Where multiple activities are selected, the auxotrophy-restoring selection markers can be of a biosynthetic-type (anabolic), of a utilization-type (catabolic), or may be chosen from both types. For example, one or more than one activity in a given biosynthetic pathway for the selected compound may be knocked-out; or more than one activity, each from different biosynthetic pathways, may be knocked-out. The corresponding activity or activities are then provided by at least one recombinant vector which, upon transformation into the cell, restores prototrophy to the cell.

Compounds and molecules whose biosynthesis or utilization can be targeted to produce auxotrophic host cells include: lipids, including, for example, fatty acids; mono-and disaccharides and substituted derivatives thereof, including, for example, glucose, fructose, sucrose, glucose-6-phosphate, and glucuronic acid, as well as Entner-Doudoroff and Pentose Phosphate pathway intermediates and products; nucleosides, nucleotides, dinucleotides, including, for example, ATP, dCTP, FMN, FAD, NAD, NADP, nitrogenous bases, including, for example, pyridines, purines, pyrimidines, pterins, and hydro-, dehydro-, and/or substituted nitrogenous base derivatives, such as cofactors, for example, biotin, cobamamide, riboflavine, thiamine; organic acids and glycolysis and citric acid cycle intermediates and products, including, for example, hydroxyacids and amino acids; storage carbohydrates and storage poly(hydroxyalkanoate) polymers, including, for example, cellulose, starch, amylose, amylopectin, glycogen, poly-hydroxybutyrate, and polylactate.

In one embodiment, the biocatalytic activity(ies) knocked out to produce the auxotrophic host cell is selected from the group consisting of: the lipids; the nucleosides, nucleotides, dinucleotides, nitrogenous bases, and nitrogenous base derivatives; and the organic acids and glycolysis and citric acid cycle intermediates and products. Preferably, the biocatalytic activity(ies) knocked out is selected from the group consisting of: the nucleosides, nucleotides, dinucleotides, nitrogenous bases, and nitrogenous base derivatives; and the organic acids and glycolysis and citric acid cycle intermediates and products. More preferably, the biocatalytic activity(ies) knocked out is selected from the group consisting of: the pyrimidine nucleosides, nucleotides, dinucleotides, nitrogenous bases, and nitrogenous base derivatives; and the amino acids.

A given transgenic host cell may use one or more than one selection marker or selection marker system. For example, one or more biosynthesis selection marker(s) or selection marker system(s) according to the present invention may be used together with each other, and/or may be used in combination with a utilization-type selection marker or selection marker system according to the present invention. In any one of these prototrophy-enabling embodiments, the host cell may also contain one or more non-auxotrophic selection marker(s) or selection marker system(s). Examples of non-auxotrophic selection marker(s) and system(s) include, for example: toxin-resistance marker genes such as antibiotic-resistance genes that encode an enzymatic activity that degrades an antibiotic; toxin-resistant marker genes, such as, for example, imidazolinone-resistant mutants of acetolactate synthase ("ALS;" EC 2.2.1.6) in which mutation(s) are expressed that make the enzyme insensitive to toxin-inhibition exhibited by versions of the enzyme that do not contain such mutation(s). The compound(s) may exert this effect directly; or the compound(s) may exert this effect indirectly, for example, as a result of metabolic action of the cell that converts the compound(s) into toxin form or as a result of combination of the compound(s) with at least one further compound(s).

Bacterial-host-operative genes encoding such marker enzymes can be obtained from the bacterial host cell strain chosen for construction of the knock-out cell, from other bacteria, or from other organisms, and may be used in native form or modified (e.g., mutated or sequence recombined) form. For example, a DNA coding sequence for an enzyme exhibiting the knocked out biocatalytic activity may be obtained from one or more organisms and then operatively attached to DNA regulatory elements operative within the host cell. In specific, all of the chosen host's intracellular genes that encode a selected enzymatic activity are knocked-out; the bacterial knock-out host is then transformed with a vector containing at least one operative copy of a native or non-native gene encoding an enzyme exhibiting the activity lost by the bacterial knockout.

Bacterial and other genes encoding such enzymes can be selected and obtained through various resources available to one of ordinary skill in the art. These include the nucleotide sequences of enzyme coding sequences and species-operative DNA regulatory elements. Useful on-line InterNet resources include, e.g.,: (1) the ExPASy proteomics facility (see the ENZYME and BIOCHEMICAL PATHWAYS MAPS features) of the Swiss Institute of Bioinformatics (Bâatiment Ecole de Pharmacie, Room 3041; Université de Lausanne; 1015 Lausanne-Dorigny; Switzerland) and (2) the GenBank facility and other Entrez resources (see the PUBMED, PROTEIN, NUCLEOTIDE, STRUCTURE, GENOME, et al. features) offered by the National Center for Biotechnology Information (NCBI, National Library of Medicine, National Institutes of Health, U.S. Dep. Of Health & Human Services; Building 38A; Bethesda, Md., USA).

The selected coding sequence may be modified by altering the genetic code thereof to match that employed by the bacterial host cell, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari Kisarazu, Chiba 292-0818 Japan); and (2) the Genetic Codes tables available from the NCBI Taxonomy database on the NIH website. For example, *Pseudomonas* species are reported as utilizing Genetic Code Translation Table 11 of the NCBI Taxonomy site, and as exhibiting the codon usage frequency as shown at the Kazusa site.

In a particular embodiment, *Pseudomonas fluorescens* can be used as the host cell. In one embodiment, *Pseudomonas fluorescens* provides at least one auxotrophic selection marker gene. In an alternative embodiment, *Pseudomonas fluorescens* provides all auxotrophic selection marker genes. In a particular embodiment, *Pseudomonas fluorescens* can both be the host cell and provide at least one, and preferably all, auxotrophic selection marker genes.

Biosynthetic Nucleoside and Nitrogenous Base Selection Markers

In one embodiment, a biosynthetic enzyme involved in anabolic metabolism can be chosen as the auxotrophic selection marker. In particular, the biosynthetic enzyme can be selected from those involved in biosynthesis of the nucleosides, nucleotides, dinucleotides, nitrogenous bases, and nitrogenous base derivatives.

In a particular embodiment at least one purine-type biosynthetic enzyme can be chosen as an auxotrophic selection marker. Such purine biosynthetic enzymes include, for example, adenine phosphoribosyltransferases, adenylosuccinate lyases, adenylosuccinate synthases, GMP synthases, IMP cyclohydrolases, IMP dehydrogenases, phosphoribosylamine-glycine ligases, phosphoribosyl-aminoimidazolecarboxamide formyltransferases, phosphoribosylaminoimidazole carboxylases, phosphoribosyl aminoimidazolesuccinocarboxamide synthases, phosphoribosyl-formylglycinamidine cyclo ligases, phosphoribosyl-formylglycinamidine synthases, phosphoribosyl-glycinamide formyltransferases, ribose-phosphate diphosphokinases, and ribose-5-phosphate-ammonia ligases.

In another particular embodiment, a pyrimidine-type biosynthetic enzyme can be chosen as an auxotrophic selection marker. Such pyrimidine-type biosynthetic include enzymes involved in biosynthesis of UMP, such as carbamate kinase (EC 2.7.2.2), carbamoyl-phosphate synthase (EC 6.3.5.5), aspartate carbamoyltransferase (EC 2.1.3.2), dihydroorotase (EC 3.5.2.3), dihydroorotate dehydrogenase (EC 1.3.3.1), orotate phosphoribosyltransferase ("OPRT;" EC 2.4.2.10), and orotidine-5'-phosphate decarboxylase ("ODCase;" EC 4.1.1.23).

Examples of genes encoding pyrimidine-type biosynthetic enzymes are well known. In the case of bacterial synthesis of UMP, examples of useful genes include: arcC genes, encoding carbamate kinases; carA and carB genes, collectively encoding carbamoyl-phosphate synthases; pyrB genes, encoding aspartate carbamoytransferases; pyrC genes, encoding dihydroorotases; pyrD genes, singly or collectively encoding dihydroorotate dehydrogenases; pyrE genes encoding orotate phosphoribosyltransferases; and pyrF genes, encoding orotidine-5'-phosphate decarboxylases.

In a particular embodiment, an expression system according to the present invention will utilize a pyrF auxotrophic selection marker gene. pyrF genes encode ODCase, an enzyme required for the bacterial pyrimidine nucleotide biosynthesis pathway, by which the cell performs de novo synthesis of pyrimidine nucleotides proper (UTP, CTP), as well as pyrimidine deoxynucleotides (dTTP, dCTP). The pathway's initial reactants are ATP, an amino group source (i.e. ammonium ion or L-glutamine), and a carboxyl group source (i.e. carbon dioxide or bicarbonate ion); the pathway's ultimate product is dTTP, with dCTP, UTP, and CTP also being formed in the process. Specifically, the bacterial de novo pyrimidine nucleotide biosynthesis pathway begins with the formation of carbamoyl phosphate. Carbamoyl phosphate is synthesized either: (a) by action of carbamate kinase (EC 2.7.2.2), encoded by the arcC gene; or, more commonly, (b) by action of the glutamine-hydrolyzing, carbamoyl-phosphate synthase (EC 6.3.5.5), whose small and large subunits are encoded by the carA and carB genes, respectively. Carbamoyl phosphate is then converted to UDP by the following six-step route: 1) conversion of carbamoyl phosphate to N-carbamoyl-L-aspartate, by aspartate carbamoyltransferase (EC 2.1.3.2), encoded by pyrB; then 2) conversion thereof to (S)-dihydroorotate, by dihydroorotase (EC 3.5.2.3), encoded by pyrC; then 3) conversion thereof to orotate, by dihydroorotate dehydrogenase (EC 1.3.3.1), encoded by pyrD gene(s); then 4) conversion thereof to orotidine-5'-monophosphate ("OMP"), by orotate phosphoribosyltransferase ("OPRT;" EC 2.4.2.10), encoded by pyrE; and then 5) conversion thereof to uridine-5'-monophosphate ("UMP"), by orotidine-5'-phosphate decarboxylase ("ODCase;" EC 4.1.1.23), encoded by pyrF. The UMP is then utilized by a variety of pathways for synthesis of pyrimidine nucleotides (UTP, CTP, dTTP, dCTP), nucleic acids, nucleoproteins, and other cellular metabolites.

In bacteria in which one or more of the carA, carB, or pyrB-pyrF genes has become inactivated or lost, or mutated to encode a non-functional enzyme, the cell can still thrive if uracil is added to the medium, provided that the cell contains a functioning uracil salvage pathway. Most bacteria contain a native uracil salvage pathway, including the Pseudomonads and related species. In a uracil salvage pathway, the cell imports and converts exogenous uracil into UMP, to synthesize the required pyrimidine nucleotides. In this, uracil is reacted with 5-phosphoribosyl-1-pyrophosphate to form UMP, by the action of either uracil phosphoribosyltransferase (EC 2.4.2.9), encoded by the upp gene, or by the bifunctional, pyrimidine operon regulatory protein ("pyrR bifunctional protein"), encoded by pyrR. The resulting UMP is then converted to UDP, and then the subsequent pyrimidine nucleotides, as described above.

Consequently, a pyrF(−) Pseudomonad or related cell can be maintained on uracil-containing medium. After a pyrF gene-containing DNA construct is transfected into the pyrF (−) cell and expressed to form a functioning ODCase enzyme, the resulting combined pyrF(+) plasmid-host cell system can be maintained in a medium lacking uracil.

The coding sequence of the pyrF gene for use in a Pseudomonad or related host cell can be provided by any gene encoding an orotidine-5'-phosphate decarboxylase enzyme ("ODCase"), provided that the coding sequence can be transcribed, translated, and otherwise processed by the selected Pseudomonad or related host cell to form a functioning ODCase. The pyrF coding sequence may be a native sequence, or it may be an engineered sequence resulting from, for example, application of one or more sequence-altering, sequence-combining, and/or sequence-generating techniques known in the art. Before use as part of a pyrF selection marker gene, the selected coding sequence may first be improved or optimized in accordance with the genetic code and/or the codon usage frequency of a selected Pseudomonad or related host cell. Expressible coding sequences will be operatively attached to a transcription promoter capable of functioning in the chosen host cell, as well as all other required transcription and translation regulatory elements. A native coding sequence for a pyrF gene as described above may be obtained from a bacterium or from any other organism, provided that it meets the above-described requirements.

In one embodiment, the pyrF coding sequence is isolated from the Pseudomonad or related host cell in which it is intended to be used as a selection marker. The entire pyrF gene (including the coding sequence and surrounding regulatory regions) can be isolated there from. In a particular embodiment, a bacterium providing the pyrF gene or coding sequence will be selected from the group consisting of a member of the order Pseudomonadales, a member of the suborder Pseudomonadineae, a member of the family Pseudomonadaceae, a member of the tribe Pseudomonadeae, a member of the genus *Pseudomonas*, and a member of the *Pseudomonas fluorescens* species group (i.e. the "fluorescent pseudomonads"). In a particular embodiment, the bacterium will belong to the species, *Pseudomonas fluorescens*.

In a particular embodiment, the pyrF gene contains the nucleic acid sequence of SEQ ID NO. 1 (Table 2), or a variant thereof. Alternatively, the ODCase encoded by the pyrF gene contains the amino acid sequence of SEQ ID NO. 2 (Table 3), a variant thereof, or a variant having a codon sequence redundant therewith, in accordance with the genetic code used by a given host cell according to the present invention.

Alternatively, the pyrF gene contains a nucleic acid sequence encoding an ODCase enzyme selected from the group consisting of a nucleic acid sequence at least 70%, 75%, 80%, 85%, 88%, 90%, and 95% homologous to SEQ ID No. 1. Likewise, the pyrF gene encodes an ODCase selected from the group consisting of an amino acid sequence at least 70%, 75%, 80%, 85%, 88%, 90%, and 95% homologous to SEQ ID No. 2.

In another embodiment, the pyrF gene can contain a coding sequence having a nucleotide sequence at least 90%, 93%, 95%, 96%, 97%, 98% or 99% homologous to the nucleotide sequence of nucleotides 974-1669 of SEQ ID NO: 1.

In a particular embodiment, the pyrF gene can contain a coding sequence having a codon sequence that hybridizes to the anti-codon sequence of SEQ ID NO:3 (Table 4), when hybridization has been performed under highly stringent hybridization conditions, or can have a codon sequence redundant therewith. In a particularly particular embodiment, the pyrF gene will contain the nucleotide sequence of SEQ ID No. 3

TABLE 2

*PSEUDOMONAS FLUORESCENS* PYRF NUCLEIC ACID SEQUENCE gatcagttgcggagccttggggtcatcccccagtttc SEQ ID NO. 1
tgacgcaggcgcgacaccagcaagtcgatgctgcggt
cgaaagcctcgatggaacgcccacgggccgcgtccag
cagctgttcgcggctcagcacacgccgcgggcgttcg
ataaacacccacaacaaacgaaactcggcgttggaca
gcggcaccaccaggccgtcatcggccaccagctggcg
cagtacgctgttcaggcgccaagtgtcgaaacggata
ttggcccgctgttcggtgcggtcatcacgcaccggc
gcaggatggtctggatacgcgcgaccagttcccgggg
ttcgaacggcttggacatatagtcgtctgccccagt
tccaggccgatgatgcggtcggtgggttcgcagcggg
cggtgagcatcaggatcggaatgtccgattcggcgcg
cagccagcggcacaatgtcagcccgtcttcgcccggc
agcatcaggtcgagcaccaccacatcgaaggtctccg
cttgcatggcctggcgcatggcgatgccgtcggtgac
gcctgaggcgagaatattgaagcgtgccaggtagtcg
atcagcagttcgcggatcggcacgtcgtcgtcgacaa
tcagcgcgcgggtgttccagcgcttgtcttcggcgat
caccgcgtcttttggcgcttcgtttacagggtcgcaa
ggggtatgcatagcgaggtcatctgcctggttgtggc
tgtcagcataggcgcccagttccagggctggaagtgc
tgggcgggcggtcatgtgcgcgaggctagccgggcgg
cgtattgggggcgtgtcgtgaatgtatcgggcttgaa
acaattgccttgaatcgccggtattgggcgcttgatc
ggtatttaccgatcatcggatcccgcaacggcgctgc
ttgcgctacaatccgcgccgatttcgacttgcctgag
agcccattccaatgtccgtctgccagactcctatcat
cgtcgccctggattaccccaccccgtgacgccgcactg
aagctggctgaccagttggaccccaagctttgccggg
tcaaggtcggcaaggaattgttcaccagttgcgcggc
ggaaatcgtcggcaccctgcgggacaaaggcttcgaa
gtgttcctcgacctcaaattccatgacatccccaaca
ccacggcgatggccgtcaaagccgcggccgagatggg
cgtgtggatggtcaatgtgcactgctccggtggcctg
cgcatgatgagcgcctgccgcgaagtgctggaacagc
gcagcggccccaaaccgttgttgatcggcgtgaccgt
gctcaccagcatggagcgcgaagacctggcgggcatt
ggcctggatatcgagccgcaggtgcaagtgttgcgcc
tggcagccctggcgcagaaagccggcctcgacggcct
ggtgtgctcagccctggaagcccaggccctgaaaaac
gcacatccgtcgctgcaactggtgacaccgggtatcc
gtcctaccggcagcgcccaggatgaccagcgccgtat
cctgacccgcgccaggccctggatgcgggctctgac
tacctggtgatcggccggccgatcagccaggcggcgg
atcctgcaaaagcgttggcagcggtcgtcgccgagat
cgcctgattttagagtgagcaaaaaatgtgggagct
ggcttgcctgcgatagtatcaactcggtatcacttag
aaaccgagttgcttgcatcgcaggcaagccagctccc
acatttgtttttgtggtgtgtcagctgactttgagca
ccaacttcccgaagttctcgccgttgaacagcttcat
cagcgtttccgggaatgtctccagcccttcgacaata
tcttccttgctcttgagcttgccctgggccatccagc
cggccatttcctgacccgccgcgcgaagttcgccgc
gtggtccatccaccacaaagccttccatacgcgcacgg
ttgaccagcaatgacaggtagttcgccgggcctttga
ccgcttccttgttgttgtactggctgattgcaccgca
aatcaccacgcgggctttgagcgccaggcggctgagc
accgcgtcgagaatatgccgccgacgttatcgaaat
acacgtccacgcctttggggcactcgcgcttgagggc
ggcgggcacgtcttcgcttttgtagtcgatggcggcg
tcgaagcccagctcatcgaccaggaacttgcacttct
cggcgccaccggcgatccccactacgcgacagccttt TABLE 2-continued

*PSEUDOMONAS FLUORESCENS* PYRF NUCLEIC ACID SEQUENCE gagcttagcgatctgcccggccgatgctgcccacggca
ccggcggcgccggagatcaccacggtgtcaccggctt
tcggtgcgccggtctccagcagagcaaagtaggccgt
catgccggtcatgcccagggcggacaggtagcgggc
aggggcgccagcttggggtccaccttatagaaaccac
ggggctcgccaaggaagtaatcctgcacgcccagtgc
accgttcacgtagtcccccaccgcgaagttcggatgg
ttcgaggcaagcaccttgcctacgcccagggcgcgca
tcacttcgccgatgcctaccggtgggatgtaggactt
gccttcattcatccagccacgca

TABLE 3

*PSEUDOMONAS FLUORESCENS* ODCASE AMINO ACID SEQUENCE

Met Ser Val Gys Gln Thr Pro Ile Ile   SEQ ID NO. 2
Val Ala Leu Asp Tyr Pro Thr Arg Asp
Ala Ala Leu Lys Leu Ala Asp Gln Leu
Asp Pro Lys Leu Gys Alg Val Lys Val
Gly Lys Glu Leu Phe Thr Ser Cys Ala
Ala Gln Ile Val Gly Thr Leu Arg Asp
Lys Gly Phe Glu Val Phe Leu Asp Leu
Lys Phe His Asp Ile Pro Asn Thr Thr
Ala Met Ala Val Lys Ala Ala Ala Glu
Met Gly Val Trp Met Val Asn Val His
Cys Ser Gly Gly Leu Arg Met Met Ser
Ala Cys Arg Gln Val Leu Glu Gln Arg
Ser Gly Pro Lys Pro Leu Leu Ile Gly
Val Thr Val Leu Thr Ser Met Glu Arg
Gln Asp Leu Ala Gly Ile Gly Leu Asp
Ile Glu Pro Gln Val Gln Val Leu Arg
Leu Ala Ala Leu Ala Gln Lys Ala Gly
Leu Asp Gly Leu Val Cys Ser Ala Leu
Glu Ala Gln Ala Leu Lys Asn Ala His
Pro Ser Leu Gln Leu Val Thr Pro Gly
Ile Arg Pro Thr Gly Ser Ala Gln Asp
Asp Gln Arg Arg Ile Leu Thr Pro Arg
Gln Ala Leu Asp Ala Gly Ser Asp Tyr
Leu Val Ile Gly Arg Pro Ile Ser Gln
Ala Ala Asp Pro Ala Lys Ala Leu Ala
Ala Val Val Ala Glu Ile Ala

TABLE 4

*PSEUDOMONAS FLUORESCENS* PYRF NUCLEIC ACID SEQUENCE atgtccgtctgccagactcctatcatcgtcgccctgg   SEQ ID No. 3
attaccccacccgtgacgccgcactgaagctggctga
ccagttggaccccaagctttgccgggtcaaggtcggc
aaggaattgttcaccagttgcgcggcggaaatcgtcg
gcaccctgcgggacaaaggcttcgaagtgttcctcga
cctcaaattccatgacatccccaacaccacggcgatg
gccgtcaaagccgcggccgagatgggcgtgtggatgg
tcaatgtgcactgctccggtggcctgcgcatgatgag
cgcctgccgcgaagtgctggaacagcgcagcggcccc
aaaccgttgttgatcggcgtgaccgtgctcaccagca
tggagcgcgaagacctggcgggcattggcctggatat
cgagccgcaggtgcaagtgttgcgcctggcagccctg
gcgcagaaagccggcctcgacggcctggtgtgctcag
ccctggaagcccaggccctgaaaaacgcacatccgtc
gctgcaactggtgacaccgggtatccgtcctaccggc
agcgcccaggatgaccagcgccgtatcctgacccgc
gccaggccctggatgcgggctctgactacctggtgat
cggccggccgatcagccaggcggcggatcctgcaaaa
gcgttggcagcggtcgtcgccgagatcgcc In an alternate embodiment, an expression system according to the present invention will utilize a thyA auxotrophic selection marker gene. thyA genes encode thymidylate synthase (EC 2.1.1.45), an enzyme required for the bacterial pyrimidine nucleotide biosynthesis pathway. Since DNA contains thymine (5-methyluracil) as a major base instead of uracil, the synthesis of thymidine monophospate (dTMP or thymidylate) is essential to provide dTTP (thymidine triphosphate) needed for DNA replication together with DATP, DGTP, and dCTP. Methylation of dUMP by thymidylate synthase utilizing 5,10-methylenetetrahydrofolate as the source of the methyl group generates thymidylate. Thymidylate synthesis can be interrupted, and consequently the synthesis of DNA arrested, by the removal, inhibition, or disruption of thymidylate synthase.

In bacteria in which the thyA gene has become inactivated or lost, or mutated to encode a non-functional enzyme, the cell can still thrive if exogenous thymidine is added to the medium.

In *Pseudomonas fluorescens*, the addition of an *E. coli* tdk gene, encoding thymidine kinase, is required for survival on exogenous thymidine. Therefore, prior to selection, a plasmid comprising a tdk gene can be used to transform thyA(−) *P. fluorescens* host cells, generating a thyA(−)/ptdk cell, allowing survival on a thymidine containing medium. Alternatively, a tdk gene producing a functional thymidylate synthase enzyme capable of utilizing exogenous thymidine in *Pseudomonas fluorescens* can be inserted into the genome, producing a thyA(−)/tdk(+) host cell. After a thyA gene-containing DNA construct is transfected into the thyA(−)/ptdk cell and expressed to form a functioning thymidylate synthase enzyme, the resulting combined thyA(+) plasmid-host cell system can be maintained in a medium lacking thymidine.

The coding sequence of the thyA gene for use in a Pseudomonad or related host cell can be provided by any gene encoding a thymidylate synthase enzyme ("TS"), provided that the coding sequence can be transcribed, translated, and otherwise processed by the selected Pseudomonad or related host cell to form a functioning TS. The thyA coding sequence may be a native sequence, or it may be an engineered sequence resulting from, for example, application of one or more sequence-altering, sequence-combining, and/or sequence-generating techniques known in the art. Before use as part of a thyA selection marker gene, the selected coding sequence may first be improved or optimized in accordance with the genetic code and/or the codon usage frequency of a selected Pseudomonad or related host cell. Expressible coding sequences will be operatively attached to a transcription promoter capable of functioning in the chosen host cell, as well as all other required transcription and translation regulatory elements. A native coding sequence for a thyA gene as described above may be obtained from a bacterium or from any other organism, provided that it meets the above-described requirements.

In one embodiment, the thyA coding sequence is isolated from the Pseudomonad or related host cell in which it is intended to be used as a selection marker. The entire thyA gene (including the coding sequence and surrounding regulatory regions) can be isolated there from. In a particular embodiment, a bacterium providing the thyA gene or coding sequence will be selected from the group consisting of a member of the order Pseudomonadales, a member of the suborder Pseudomonadineae, a member of the family Pseudomonadaceae, a member of the tribe Pseudomonadeae, a member of the genus *Pseudomonas*, and a member of the *Pseudomonas fluorescens* species group (i.e. the "fluorescent pseudomonads"). In a particular embodiment, the bacterium will belong to the species, *Pseudomonas fluorescens*.

In a particular embodiment, the thyA gene contains the nucleic acid sequence of SEQ ID NO. 4 (Table 5). Alternatively, the TS encoded by the thyA gene contains the amino acid sequence of SEQ ID NO. 5 (Table 6), a variant thereof, or a variant having a codon sequence redundant therewith, in accordance with the genetic code used by a given host cell according to the present invention.

TABLE 5

*PSEUDOMONAS FLUORESCENS* THYA NUCLEIC ACID SEQUENCE atgaagcaatatctcgaactactgaacgacgtcgtga  SEQ ID NO. 4
ccaatggattgaccaagggcgatcgcaccggcaccgg
caccaaagccgtatttgcccgtcagtatcggcataac
ttggccgacggcttcccgctgctgaccaccaagaagc
ttcatttcaaaagtatcgccaacgagttgatctggat
gttgagcggcaacaccaacatcaagtggctcaacgaa
aatggcgtgaaaatctgggacgagtgggccaccgaag
acggcgacctgggcccggtgtacggcgagcaatggac
cgcctggccgaccaaggacggcggcaagatcaaccag
atcgactacatggtccacaccctcaaaaccaacccca
acagccgccgcatcctgtttcatggctggaacgtcga
gtacctgccggacgaaaccaagagcccgcaggagaac
gcgcgcaacggcaagcaagccttgccgccgtgccatc
tgttgtaccaggcgttcgtgcatgacgggcatctgtc
gatgcagttgtatatccgcagctccgacgtcttcctc
ggcctgccgtacaacaccgccgcgttggccttgctga
ctcacatgctggctcagcaatgcgacctgatccctca
cgagatcatcgtcaccaccggcgacacccatgcttac
agcaaccacatggaacagatccgcacccagctggcgc
gtacgccgaaaaagctgccggaactggtgatcaagcg
taaacctgcgtcgatctacgattacaagtttgaagac
tttgaaatcgttggctacgacgccgacccgagcatca
aggctgacgtggctatctga

TABLE 6

*PSEUDOMONAS FLUORESCENS* TS AMINO ACID SEQUENCE

MKQELYLLNDVVTNGLTKGDRTGTGTKAVFARQYRHN  SEQ ID NO. 5
LADGFPLLTTKKLHFKSIANELIWMLSGNTNIKWLNE
NGVKIWDEWATEDGDLGPVYGEQWTAWPTKDGGKINQ
IDYMVHTLKTNPNSRRILFHGWNVEYLPDETKSPQEN
ARNGKQALPPCHLLYQAFVHDGHLSMQLYIRSSDVFL
GLPYNTAALALLTHMLAQQCDLIPHEIIVTTGDTHAY
SNHMEQIRTQLARTPKKLPELVIKRKPASIYDYKFED
FEIVGYDADPSIKADVAI

Biosynthetic Amino Acid Selection Markers

In an alternative embodiment, the biosynthetic enzyme involved in anabolic metabolism chosen as the auxotrophic selection marker can be selected from those involved in the biosynthesis of amino acids. In particular embodiments, the biosynthetic amino acid enzymes are selected from the group consisting of enzymes active in the biosynthesis of: the Glutamate Family (Glu; Gln, Pro, and Arg); the Aspartate Family (Asp; Asn, Met, Thr, Lys, and Ile); the Serine Family (Ser; Gly and Cys); the Pyruvate Family (Ala, Val, and Leu); the Aromatic Family (Trp, Phe, and Tyr); and the Histidine Family (H is). Examples of genes and enzymes involved in these biosynthetic pathways include: the Glutamate Family member arg, gdh, gin, and, pro genes, including, for example, argA-argH, gdhA, ginA, proA, proC; the Aspartate Family member asd, asn, asp, dap, lys, met, and thr genes, including, for example, asnA, asnB, aspC, dapA, dapB, dapD-dapF, lysA, lysC, metA-metC, metE, metH, metL, thrA-thrC; the Serine Family member cys, gly, and ser genes, including, for example, cysE, cysK, glyA, serA-serC; the Aromatic Family member aro, phe, trp, and tyr genes, including, for example, aroA-aroH, aroK, aroL, trpAtrpE, tyrA, and tyrB; and the Histidine Family member his genes, including hisA-hisD, hisF-hisH.

In a further particular embodiment, the auxotrophic selection marker can be selected from enzymes involved in the biosynthesis of members of the Glutamate Family. Examples of useful Glutamate Family auxotrophic selection markers include the following, listed with representative examples of their encoding genes: argA, encoding N-acetylglutamate synthases, amino acid acetyltransferases; argB, encoding acetylglutamate kinases; argC, encoding N-acetyl-gamma-glutamylphosphate reductases; argD, encoding acetylornithine delta-aminotransferases; argE, encoding acetylornithine deacetylases; argF and argI, encoding ornithine carbamoyltransferases; argg, encoding argininosuccinate synthetases; argH, encoding argininosuccinate lyases; gdhA, encoding glutamate dehydrogenases; ginA, encoding glutamine synthetases; proA, encoding gamma-glutamylphosphate reductases; proB, encoding gamma-glutamate kinases; and proC, encoding pyrroline-5-carboxylate reductases.

In one embodiment, an amino acid biosynthesis selection marker gene can be at least one member of the proline biosynthesis family, in particular proA, prob, or proC. In a particular embodiment, the proline biosynthesis selection marker gene can comprise a proC gene. proC genes encode an enzyme catalyzing the final step of the proline biosynthesis pathway. In bacteria, the proline (i.e. L-proline) biosynthesis pathway comprises a three-enzyme process, beginning with L-glutamic acid. The steps of this process are: 1) conversion of L-glutamic acid to L-glutamyl-5-phosphate, by glutamate-5-kinase ("GK;" EC 2.7.2.11), encoded by proB; then 2a) conversion thereof to L-glutamate-5-semialdehyde, by glutamate-5-semialdehyde dehydrogenase (EC 1.2.1.41), also known as glutamyl-5-phosphate reductase ("GPR"), encoded by proA, followed by 2b) spontaneous cyclization thereof to form .i-pyrroline-5-carboxylate; and then 3) conversion thereof to L-proline, by $\Delta^1$-pyrroline-5-carboxylate reductase ("P5CR;" EC 1.5.1.2), encoded by proC. In most bacteria, proC encodes the P5CR subunit, with the active P5CR enzyme being a homo-multimer thereof.

In bacteria in which one or more of the proA, proB, or proC genes has become inactivated or lost, or mutated to encode a non-functional enzyme, the cell can still thrive if proline is added to the medium. Consequently, a proC(−) Pseudomonad or related cell can be maintained on a proline-containing medium. After a proC gene-containing DNA construct is transfected into the proC(−) cell and expressed to form a functioning P5CR enzyme, the resulting combined proC(+) plasmid-host cell system can be maintained in a medium lacking proline.

The coding sequence of the proC gene for use in a Pseudomonad or related host cell can be provided by any gene encoding an $\Delta^1$-pyrroline-5-carboxylate reductase enzyme (P5CR), provided that the coding sequence can be transcribed, translated, and otherwise processed by the selected Pseudomonad or related host cell to form a functioning P5CR. The proC coding sequence may be a native sequence, or it may be an engineered sequence resulting from, for example, application of one or more sequence-altering, sequence-combining, and/or sequence-generating techniques known in the art. Before use as part of a proC selection marker gene, the selected coding sequence may first be improved or optimized in accordance with the genetic code and/or the codon usage frequency of a selected Pseudomonad or related host cell. Expressible coding sequences will be operatively attached to a transcription promoter capable of functioning in the chosen host cell, as well as all other required transcription and translation regulatory elements. A native coding sequence for a proC gene as described above may be obtained from a bacterium or from any other organism, provided that it meets the above-described requirements.

In one embodiment, the proC coding sequence is isolated from the Pseudomonad or related host cell in which it is intended to be used as a selection marker. The entire proC gene (including the coding sequence and surrounding regulatory regions) can be isolated therefrom. In a particular embodiment, a bacterium providing the proC gene or coding sequence will be selected from the group consisting of a member of the order Pseudomonadales, a member of the suborder Pseudomonadineae, a member of the family Pseudomonadaceae, a member of the tribe Pseudomonadeae, a member of the genus *Pseudomonas*, and a member of the *Pseudomonas fluorescens* species group (i.e. the "fluorescent pseudomonads"). In a particular embodiment, the bacterium will belong to the species, *Pseudomonas fluorescens*.

In a particular embodiment, the proC gene contains the nucleic acid sequence of SEQ ID NO:6 (Table 7), or a variant thereof. Alternatively, the P5CR encoded by the proC gene contains the amino acid sequence of SEQ ID NO. 7 (Table 8), a variant thereof, or a variant having a codon sequence redundant therewith, in accordance with the genetic code used by a given host cell according to the present invention.

Alternatively, the proC gene contains a nucleic acid sequence encoding an P5CR enzyme that is at least 70%, 75%, 80%, 85%, 88%, 90%, and 95% homologous to SEQ ID No. 6. Likewise, the proC gene encodes an ODCase that is at least 70%, 75%, 80%, 85%, 88%, 90%, and 95% homologous to SEQ ID No. 7.

In another embodiment, the proC gene can contain a coding sequence at least 90%, 93%, 95%, 96%, 97%, 98% or 99% homologous to the nucleotide sequence of SEQ. ID NO. 8 (Table 9).

In a particular embodiment, the proC gene can contain a coding sequence having a codon sequence that hybridizes to the anti-codon sequence of SEQ ID NO. 8, when hybridization has been performed under stringent hybridization conditions, or can have a codon sequence redundant therewith. In a particularly particular embodiment, the proC gene will contain the nucleotide sequence of SEQ ID NO. 8.

TABLE 7

| PSEUDOMONAS FLUORESCENS PROC NUCLEIC ACID SEQUENCE |
|---|
| gcccttgagttggcacttcatcggccccattcaatcg SEQ ID NO. 6<br>aacaagactcgtgccatcgccgagcacttcgcttgggt<br>gcactccgtggaccgcctgaaaatcgcacaacgcctgt<br>ccgaacaacgcccggccgacctgccgccgctcaatatc<br>tgcatccaggtcaatgtcagtggcgaagccagcaagtc<br>cggctgcacgcccgctgacctgccggccctggccacag<br>cgatcagcgccctgccgcgcttgaagctgcggggcttg<br>atggcgattcccgagccgacgcaagacgggcggagca<br>ggatgcggcgttcgccacggtgcgcgacttgcaagcca<br>gcttgaacctggcgctggacacactttccatgggcatg<br>agccacgaccttgagtcggccattgcccaaggcgccac<br>ctgggtgcggatcggtaccgccctgtttggcgcccgcg<br>actacggccagccgtgaaatggctgacatccctcgaaa<br>taaggacctgtcatgagcaacacgcgtattgcctttat<br>cggcgccggtaacatggcggccagcctgatcggtggcc<br>tgcgggccaagggcctggacgccgagcagatccgcgcc<br>agcgacccccggtgccgaaacccgcgagcgcgtcagagc<br>cgaacacggtatccagaccttcgccgataacgccgagg<br>ccatccacggcgtcgatgtgatcgtgctggcggtcaag<br>ccccaggccatgaaggccgtgtgcgagagcctgagccc<br>gagcctgcaaccccatcaactggtggtgtcgattgccg<br>ctggcatcacctgcgccagcatgaccaactggctcggt<br>gcccagccattgtgcgctgcatgcccaacaccccggc<br>gctgctgcgccagggcgtcagcggtttgtatgccactg<br>gcgaagtcaccgcgcagcaacgtgaccaggcccaggaa<br>ctgctgtctgcggtgggcatcgccgtgtggctggagca<br>ggaacagcaactggatgcggtcaccgccgtctccggca<br>gcggcccggcttacttcttcctgttgatcgaggccatg<br>acggccgcaggcgtcaagctgggcctgccccacgacgt |

TABLE 7-continued

PSEUDOMONAS FLUORESCENS PROC NUCLEIC ACID SEQUENCE

```
ggccgagcaactggcggaacaaaccgccctgggcgccg
ccaagatggcggtcggcagcgaggtggatgccgccgaa
ctgcgccgtcgcgtcacctcgccaggtggtaccacaca
agcggctattgagtcgttccaggccggggcctttgaag
ccctggtggaaacagcactgggtgccgccgcacatcgt
tcagccgagatggctgagcaactgggcaaatagtcgtc
ccttaccaaggtaatcaaacatgctcggaatcaatgac
gctgccattttcatcatccagaccctgggcagcctgta
cctgctgatcgtactgatgcgctttatcctgcaactgg
tgcgtgcgaacttctacaacccgctgtgccagttcgtg
gtgaaggccacccaaccgctgctcaagccgctgcgccg
ggtgatcccgagcctgttcggcctggacatgtcgtcgc
tggtgctggcgctgttgctgcagattttgctgttcgtg
gtgatcctgatgctcaatggataccaggccttcaccgt
gctgctgttgccatggggcctgatcgggattttctcgc
tgttcctgaagatcattttctggtcgatgatcatcagc
gtgatcctgtcctgggtcgcaccgggtagccgtagccc
gggtgccgaattggtggctcagatcaccgagccggtgc
tggcacccttccgtcgcctgattccgaacctgggtggc
ctggatatctcgccgatcttcgcgtttatc
```

TABLE 8

PSEUDOMONAS FLUORESCENS P5CR AMINO ACID SEQUENCE

```
Met Ser Asn Thr Arg Ile Ala Phe Ile    SEQ ID NO. 7
Gly Ala Gly Asn Met Ala Ala Ser Leu
Ile Gly Gly Leu Arg Ala Lys Gly Leu
Asp Ala Glu Gln Ile Arg Ala Ser Asp
Pro Gly Ala Glu Thr Arg Gln Arg Val
Arg Ala Glu His Gly Ile Gln Thr Phe
Ala Asp Asn Ala Glu Ala Ile His Gly
Val Asp Val Ile Val Leu Ala Val Lys
Pro Gln Ala Met Lys Ala Val Cys Glu
Ser Leu Ser Pro Ser Leu Gln Pro His
Gln Leu Val Val Ser fle Ala Ala Gly
Ile Thr Cys Ala Ser Met Thr Asn Trp
Leu Gly Ala Gln Pro Ile Val Alg Cys
Met Pro Asn Thr Pro Ala Leu Leu Arg
Gln Gly Val Ser Gly Leu Tyr Ala Thr
Gly Glu Val Thr Ala Gln Gln Arg Asp
Gln Ala Gln Glu Leu Leu Ser Ala Val
Gly Ile Ala Val Trp Leu Gln Gln Gln
Gln Gln Leu Asp Ala Val Thr Ala Val
Ser Gly Ser Gly Pro Ala Tyr Phe Phe
Leu Leu Ile Gln Ala Met Thr Ala Ala
Gly Val Lys Leu Gly Leu Pro His Asp
Val Ala Glu Gln Leu Ala Glu Gln Thr
Ala Leu Gly Ala Ala Lys Met Ala Val
Gly Ser Glu Val Asp Ala Ala Glu Leu
Arg Arg Arg Val Thr Ser Pro Gly Gly
Thr Thr Gln Ala Ala Ile Glu Ser Phe
Gln Ala Gly Gly Phe Gln Ala Leu Val
Glu Thr Ala Leu Gly Ala Ala Ala His
Arg Ser Ala Gln Met Ala Glu Gln Leu
Gly Lys
```

TABLE 9

PSEUDOMONAS FLUORESCENS PROC NUCLEIC ACID SEQUENCE

```
atgagcaacacgcgtattgcctttatcggcgccggta    SEQ ID NO. 8
acatggcggccagcctgatcggtggctgcgggccaa
gggcctggacgccgagcagatccgcgccagcgacccc
ggtgccgaaaccgcgagcgcgtcagagccgaacacg
gtatccagaccttcgccgataacgccgaggccatcca
cggcgtcgatgtgatcgtgctggcggtcaagcccag
gccatgaaggccgtgtgcgagagcctgagcccgagcc
tgcaaccccatcaactggtggtgtcgattgccgctgg
catcacctgcgccagcatgaccaactggctcggtgcc
cagcccattgtgcgctgcatgcccaacaccccggcgc
tgctgcgccagggcgtcagcggtttgtatgccactgg
cgaagtcaccgcgcagcaacgtgaccaggccaggaa
```

TABLE 9-continued

PSEUDOMONAS FLUORESCENS PROC NUCLEIC ACID SEQUENCE

```
ctgctgtctgcggtgggcatcgccgtgtggctggagc
aggaacagcaactggatgcggtcaccgccgtctccgg
cagcggcccggcttacttcttcctgttgatcgaggcc
atgacggccgcaggcgtcaagctgggcctgccccacg
acgtggccgagcaactggcggaacaaaccgccctggg
cgccgccaagatggcggtcggcagcgaggtggatgcc
gccgaactgcgccgtcgcgtcacctcgccaggtggta
ccacacaagcggctattgagtcgttccaggccggggg
ctttgaagccctggtggaaacagcactgggtgccgcc
gcacatcgttcagccgagatggctgagcaactgggca
aa
```

Utilization Selection Markers

In one embodiment, an enzyme involved in the catabolic utilization of metabolites can be chosen as the auxotrophic selection marker. In particular, the enzymes can be selected from those involved in the utilization of a carbon source. Examples of such enzymes include, for example, sucrases, lactases, maltases, starch catabolic enzymes, glycogen catabolic enzymes, cellulases, and poly(hydroxyalkanoate) depolymerases. If the bacterial host cell exhibits native catabolic activity of the selected type, it can be knocked-out before transformation with the prototrophy-restoring vector. Bacteria exhibiting native auxotrophy for these compounds can also be used in their native state for such transformation. In those embodiments in which a compound not importable or diffusible into the cell can be selected and supplied to the medium, the prototrophy restoring or prototrophy-enabling enzyme(s) can be secreted for use. In that case, the secreted enzyme(s) can degrade the compound extracellularly to produce smaller compounds, for example glucose, that are diffusible or importable into the cell, by selecting or designing the coding sequence of the enzyme(s) to include a coding sequence for a secretion signal peptide operative within the chosen host cell. In these embodiments, the prototrophy-restorative gene can be selected or be engineered to include a coding sequence for a secretion signal peptide operative within the chosen host cell to obtaining transport of the enzyme across the cytoplasmic membrane. In either of these embodiments, or those in which the selected compound is importable or diffusible into the cell, the cell will be grown in medium supplying no other carbon source apart from the selected compound.

In a carbon-source-utilization-based marker system, every prototrophy-restorative or prototrophy-enabling carbon-source utilization enzyme can be involved in utilization of only one carbon source. For example, two genes from the same catabolic pathway may be expressed together on one vector or may be co-expressed separately on different vectors in order to provide the prototrophy. Specific examples of such multi-gene carbon-source-utilization-based marker systems include, for example, the use of glycogen as the sole carbon source with transgenic expression of both a glycogen phosphorylase and an (alpha-1,4) glucantransferase; and the use of starch as the sole carbon source with transgenic expression of both an alpha-amylase, and an alpha(1->6) glucosidase. However, the selected single-or multi-gene carbon-source marker system can be used simultaneously with other types of marker system(s) in the same host cell, provided that the only carbon source provided to the cell is the compound selected for use in the carbon-source catabolic selection marker system.

Other examples of useful enzymes for biochemical-utilization-type activities are well known in the art, and can include racemases and epimerases that are capable of converting a non-utilizable D-carbon source, supplied to the cell, to a nutritive L-carbon source. Examples of these systems include, for example: a D-acid or a D-acyl compound used with trangenic expression of the corresponding racemase; and lactate used with transgenically expressed lactate racemase.

Similarly, where an amino acid biosynthetic activity has been selected for use in the marker system, the auxotrophy may also be overcome by supplying the cell with both a non-utilizable R-amino acid and an R-amino acid racemase or epimerase (EC 5.1.1) that converts the R-amino acid into the corresponding L-amino acid for which the cell is auxotrophic.

Trait Stacking

A plurality of phenotypic changes can also be made to a host cell, before or after insertion of an auxotrophic selection marker gene, for target gene expression, according to the present invention. For example, the cell can be genetically engineered, either simultaneously or sequentially, to exhibit a variety of enhancing phenotypic traits. This process is referred to as "trait stacking." A pryF deletion may be present as one such phenotypic trait. In such a strain, a pyrF gene, according to the present invention, can be used on a suicide vector as both a selectable marker and a counterselectable marker (in the presence of 5'-fluoroorotic acid) in order to effect a cross-in/cross-out allele exchange of other desirable traits. Thus, a pyrF gene according to the present invention may be used in a process for "trait stacking" a host cell. In such a process, a suicide vector containing such a pyrF gene can be transformed into the host cell strain in a plurality of separate transformations; in each such procedure the re-establishment of the pyrF phenotype can be used to create, ad infinitum, subsequent genetically-enhancing phenotypic change. Thus, not only can the pyrF gene itself provide a trait, it can be used to obtain additional phenotypic traits in a process of trait-stacking.

In one embodiment, the present invention provides auxotrophic Pseudomonads and related bacteria that have been further genetically modified to induce additional auxotrophies. For example, a pyrF(−) auxotroph can be further modified to inactivate another biosynthetic enzyme present in an anabolic or catabolic pathway, such as through the inactivation of a proC gene or a thyA gene. In this way, multiple auxotrophies in the host cell can be produced.

In another embodiment, genetic alterations can be made to the host cell in order to improve the expression of recombinant polypeptides in the host cell. Further modifications can include genetic alterations that allow for a more efficient utilization of a particular carbon source, thereby optimizing the overall efficiency of the entire fermentation.

In one particular embodiment, auxotrophic host cells are further modified by the insertion of a lacI containing transgene into the host chromosome. Preferably, the lacI transgene, or derivate thereof, is other than part of a whole or truncated structural gene containing PlacI-lacI-lacZYA construct.

Modifications to induce Auxotrophism

A Pseudomonad or related host cell selected for use in an expression system according to the present invention can be deficient in its ability to express any functional biocatalyst exhibiting the selected auxotrophic activity. For example, where an orotidine-5'-phosphate decarboxylase activity is selected, the host cell can be deficient in its ability to express a) any pyrF gene product (i.e. any functional ODCase enzyme), and b) any effective replacement therefore (i.e. any other biocatalyst having ODCase activity). In a one embodiment, the host cell will be made biocatalytically-deficient for the selected activity by altering its genomic gene(s) so that the cell cannot express, from its genome, a functional enzyme involved in the targeted auxotrophy (i.e. ODCase). In other words, the prototrophic cell (activity(+) cell) will become auxotrophic through the "knock-out" of a functional enzymatic encoding gene involved in the targeted prototrophic pathway (i.e. an activity(−) cell). This alteration can be done by altering the cell's genomic coding sequence(s) of the gene(s) encoding the selected activty(ies). In one embodiment, the coding sequence alteration(s) will be accomplished by introducing: insertion or deletion mutation(s) that change the coding sequence reading frame(s); substitution or inversion mutations that alter a sufficient number of codons; and/or deletion mutations that delete a sufficiently large group of contiguous codons there from capable of producing a non-functional enzyme.

In a one embodiment in which the host cell strain has also provided the auxotrophic gene(s) for use as selection marker(s) therein, preferably each of the selected gene's transcription promoter and/or transcription terminator element(s) can also be inactivated by introduction of mutation(s), including deletion mutations. For example, the transcription element inactivafion can be optionally performed in addition to the coding sequence alteration(s) described above. In a one embodiment in which the host cell strain has also provided the auxotrophic selection marker gene(s), all of the selected gene(s)'s DNA can be deleted from the host cell genome.

Such knock-out strains can be prepared according to any of the various methods known in the art as effective. For example, homologous recombination vectors containing homologous targeted gene sequences 5' and 3' of the desired nucleic acid deletion sequence can be transformed into the host cell. Ideally, upon homologous recombination, a desired targeted enzymatic gene knock-out can be produced.

Specific examples of gene knock-out methodologies include, for example: Gene inactivation by insertion of a polynucleotide has been previously described. See, e.g., DL Roeder & A Colhmer, *Marker-exchange mutagenesis of a pectate lyase isozyme gene in Erwinia chrysanthemi*, J. Bacteriol. 164(1):51-56 (1985). Alternatively, transposon mutagenesis and selection for desired phenotype (such as the inability to metabolize benzoate or anthranilate) can be used to isolate bacterial strains in which target genes have been insertionally inactivated. See, e.g., K Nida & P P Cleary, *Insertional inactivation of streptolysin S expression in Streptococcus pyogenes*, J. Bacteriol. 155(3):1156-61 (1983). Specific mutations or deletions in a particular gene can be constructed using cassette mutagenesis, for example, as described in J A Wells et al., *Cassette mutagenesis: an efficient method for generation of multiple mutations at defined sites*, Gene 34(2-3):315-23 (1985); whereby direct or random mutations are made in a selected portion of a gene, and then incorporated into the chromosomal copy of the gene by homologous recombination.

In one embodiment, both the organism from which the selection marker gene(s) is obtained and the host cell in which the selection marker gene(s) is utilized can be selected from a prokaryote. In a particular embodiment, both the organism from which the selection marker gene(s) is obtained and the host cell in which a selection marker gene(s) is utilized can be selected from a bacteria. In another embodiment, both the bacteria from which the selection marker gene(s) is obtained and the bacterial host cell in which a selection marker gene(s) is utilized, will be selected from the Proteobacteria. In still another embodiment, both the bacteria from which the selection marker gene(s) is obtained and the bacterial host cells in which a selection marker gene(s) is utilized, can be selected from the Pseudomonads and closely related bacteria or from a Subgroup thereof, as defined below.

In a particular embodiment, both the selection marker gene(s) source organism and the host cell can be selected from the same species. Preferably, the species will be a prokaryote; more preferably a bacterium, still more preferably a Proteobacterium. In another particular embodiment, both the selection marker gene(s) source organism and the host cell can be selected from the same species in a genus selected from the Pseudomonads and closely related bacteria or from a Subgroup thereof, as defined below. In one embodiment, both the selection marker gene(s) source organism and the host cell can be selected from a species of the genus *Pseudomonas*, particularly the species *Pseudomonas fluorescens*, and preferably the species *Pseudomonas fluorescens* biotype A.

III. lacI Insertion

The present invention provides Pseudomonads and related cells that have been genetically modified to contain a chromosomally insert lacI transgene or derivative, other than as part of a whole or truncated PlacI-lacI-lacZYA operon. In one embodiment, the lacI insert provides stringent expression vector control through the expression of the LacI repressor protein which binds to the lacO sequence or derivative on the vector, and inhibits a Plac-Ptac family promoter on the vector. The result is reduced basal levels of recombinant polypeptide expression prior to induction.

In one embodiment, Pseudomonad host cells containing a chromosomal insertion of a native *E. coli* lacI gene, or lacI gene derivative such as lacI$^Q$ or lacI$^{Q1}$, are provided wherein the lac insert is other than part of a whole or truncated, structural gene-containing PlacI-lacI-lacZYA construct. Other derivative lacI transgenes useful in the present invention include: lacI derivatives that have altered codon sequences different from a native lacI gene (for example, the native *E. coli* lacI gene contains a 'gtg' initiation codon, and this may be replaced by an alternative initiation codon effective for translation initiation in the selected expression host cell, e.g., 'atg'); lacI derivatives that encode LacI proteins having mutated amino acid sequences, including temperature-sensitive lacI mutants, such as that encoded by lacI$^{ts}$ (or "lacI(Ts)"), which respond to a shift in temperature in order to achieve target gene induction, e.g., a shift up to 42° C. (see, e.g., Bukrinsky et al., *Gene* 70:415-17 (1989); N Hasan & W Szybalski, *Gene* 163(1):35-40 (1995); H Adari et al., *DNA Cell Biol.* 14:945-50 (1995)); LacI mutants that respond to the presence of alternative sugars other than lactose in order to achieve induction, e.g., arabinose, ribose, or galactose (see, e.g., WO 99/27108 for Lac Repressor Proteins with Altered Responsivity); and LacI mutants that exhibit at least wild-type binding to lac operators, but enhanced sensitivity to an inducer (e.g., IPTG), or that exhibit enhanced binding to lac operators, but at least wild-type de-repressibility (see, e.g., L Swint-Kruse et al., *Biochemistry* 42(47):14004-16 (2003)).

In a particular embodiment, the gene encoding the Lac repressor protein inserted into the chromosome is identical to that of native *E. coli* lacI gene, and has the nucleic acid sequence of SEQ ID NO. 9 (Table 10). In another embodiment, the gene inserted into the host chromosome encodes the Lac repressor protein having the amino acid sequence of SEQ ID NO. 10 (Table 11).

TABLE 10

NUCLEIC ACID SEQUENCE OF NATIVE *E. COLI* LACI GENE

```
Gacaccatcgaatggcgcaaaaccttcgcggtatgg   SEQ ID NO 9
catgatagcgcccggaagagagtcaattcagggtggt
gaatgtgaaaccagtaacgttatacgatgtcgcagag
tatgccggtgtctcttatcagaccgtttcccgcgtgg
tgaaccaggccagccacgtttctgcgaaaacgcggga
aaaagtggaagcggcgatggcggagctgaattacatt
cccaaccgcgtggcacaacaactggcgggcaaacagt
cgttgctgattggcgttgccacctccagtctggccct
gcacgcgccgtcgcaaattgtcgcggcgattaaatct
cgcgccgatcaactgggtgccagcgtggtggtgtcga
tggtagaacgaagcggcgtcgaagcctgtaaagcggc
ggtgcacaatcttctcgcgcaacgcgtcagtgggctg
atcattaactatccgctggatgaccaggatgccattg
ctgtggaagctgcctgcactaatgttccggcgttatt
tcttgatgtctctgaccagacacccatcaacagtatt
attttctcccatgaagacggtacgcgactgggcgtgg
agcatctggtcgcattgggtcaccagcaaatcgcgct
gttagcgggcccattaagttctgtctcggcgcgtctg
cgtctggctggctggcataaatatctcactcgcaatc
aaattcagccgatagcggaacgggaaggcgactggag
tgccatgtccggttttcaacaaaccatgcaaatgctg
aatgagggcatcgttcccactgcgatgctggttgcca
acgatcagatggcgctgggcgcaatgcgcgccattac
cgagtccgggctgcgcgttggtgcggatatctcggta
gtgggatacgacgataccgaagacagctcatgttata
tcccgccgtcaaccaccatcaaacaggattttcgcct
gctggggcaaaccagcgtggaccgcttgctgcaactc
tctcagggccaggcggtgaagggcaatcagctgttgc
ccgtctcactggtgaaaagaaaaaccaccctggcgcc
caatacgcaaaccgcctctccccgcgcgttggccgat
tcattaatgcagctggcacgacaggtttcccgactgg
aaagcgggcagtgagcgcaacgcaattaatgtgagtt
agctcactcattaggcacccaggctttacactttat
gcttccggctcgtatgttgtgtggaattgtgagcgga
taacaatttcacacaggaaacagctatgaccatgatt
acggattcactggccgtcgttttacaacgtcgtga
```

TABLE 11

AMINO ACID SEQUENCE OF LACI REPRESSOR

```
Met Lys Pro Val Thr Leu Tyr Asp Val   SEQ ID NO. 10
Ala Glu Tyr Ala Gly Val Ser Tyr Gln
Thr Val Ser Arg Val Val Asn Gln Ala
Ser His Val Ser Ala Lys Thr Arg Glu
Lys Val Gly Ala Ala Met Ala Glu Leu
Asn Tyr Ile Pro Asn Arg Val Ala Gln
Gln Leu Ala Gly Lys Gln Ser Leu Leu
Ile Gly Val Ala Thr Ser Ser Leu Ala
Leu His Ala Pro Ser Gln Ile Val Ala
Ala Ile Lys Ser Arg Ala Asp Gln Leu
Gly Ala Ser Val Val Val Ser Met Val
Glu Arg Ser Gly Val Glu Ala Cys Lys
Ala Ala Val His Asn Leu Leu Ala Gln
Arg Val Ser Gly Leu Ile Ile Asn Tyr
Pro Leu Asp Asp Gln Asp Ala Ile Ala
Val Glu Ala Ala Cys Thr Asn Val Pro
Ala Leu Phe Leu Asp Val Ser Asp Gln
Thr Pro Ile Asn Ser Ile Phe Ser His
Glu Asp Gly Thr Arg Leu Gly Val Glu
His Leu Val Ala Leu Gly His Gln Gln
Ile Ala Leu Leu Ala Gly Pro Leu Ser
Ser Val Ser Ala Arg Leu Arg Leu Ala
Gly Trp His Lys Tyr Leu Thr Arg Asn
Gln Ile Gln Pro Ile Ala Glu Arg Glu
Gly Asp Trp Ser Ala Met Ser Gly Phe
Gln Gln Thr Met Gln Met Leu Asn Glu
Gly Ile Val Pro Thr Ala Met Leu Val
Ala Asn Asp Gln Met Ala Leu Gly Ala
Met Arg Ala Ile Thr Glu Ser Gly Leu
Arg Val Gly Ala Asp Ile Ser Val Val
Gly Tyr Asp Asp Thr Glu Asp Ser Ser
Cys Tyr Ile Pro Pro Ser Thr Thr Ile
Lys Gln Asp Phe Arg Leu Leu Gly Gln
Thr Ser Val Asp Arg Leu Leu Gln Leu
```

TABLE 11-continued

AMINO ACID SEQUENCE OF LACI REPRESSOR

Ser Gln Gly Gln Ala Val Lys Gly Asn
Gln Leu Leu Pro Val Ser Leu Val Lys
Arg Lys Thr Thr Leu Ala Pro Asn Thr
Gln Thr Ala Ser Pro Arg Ala Leu Ala
Asp Ser Leu Met Gln Leu Ala Arg Gln
Val Ser Arg Leu Glu Ser Gly Gln

In an alternative embodiment, the inserted lacI transgene is a derivative of the native *E. coli* lacI gene. In one particular embodiment, the lacI derivative gene is the lacI$^Q$ gene having the nucleic acid sequence of SEQ ID NO.11 (Table 12). The lacI$^Q$ variant is identical to the native *E. coli* lacI gene except that it has a single point mutation in the −35 region of the promoter which increases the level of lacI repressor by 10-fold in *E. coli*. See, for example, MP Calos, Nature 274 (5673): 762-65 (1978).

TABLE 12

NUCLEIC ACID SEQUENCE OF LACI$^Q$ GENE

```
gacaccatcgaatggtgcaaaaccttcgcggtatgg    SEQ ID NO. 11
catgatagcgcccgaagagagtcaattcagggtggt
gaatgtgaaaccagtaacgttatacgatgtcgcagag
tatgccggtgtctcttatcagaccgtttcccgcgtgg
tgaaccaggccagccacgtttctgcgaaaacgcggga
aaaagtggaagcggcgatggcggagctgaattacatt
cccaaccgcgtggcacaacaactggcgggcaaacagt
cgttgctgattggcgttgccacctccagtctggccct
gcacgcgccgtcgcaaattgtcgcggcgattaaatct
cgcgccgatcaactgggtgccagcgtggtggtgtcga
tggtagaacgaagcggcgtcgaagcctgtaaagcggc
ggtgcacaatcttctcgcgcaacgcgtcagtgggctg
atcattaactatccgctggatgaccaggatgccattg
ctgtggaagctgcctgcactaatgttccggcgttatt
tcttgatgtctctgaccagacacccatcaacagtatt
attttctcccatgaagacggtacgcgactgggcgtgg
agcatctggtcgcattgggtcaccagcaaatcgcgct
gttagcgggcccattaagttctgtctcggcgcgtctg
cgtctggctggctggcataaatatctcactcgcaatc
aaattcagccgatagcggaacgggaaggcgactggag
tgccatgtccggttttcaacaaaccatgcaaatgctg
aatgagggcatcgttcccactgcgatgctggttgcca
acgatcagatggcgctgggcgcaatgcgcgccattac
cgagtccgggctgcgcgttggtgcggatatctcggta
gtgggatacgacgataccgaagacagctcatgttata
tcccgccgtcaaccaccatcaaacaggattttcgcct
gctggggcaaaccagcgtggaccgcttgctgcaactc
tctcagggccaggcggtgaaggcaatcagctgttgc
ccgtctcactggtgaaaagaaaaaccaccctggcgcc
aatacgcaaaccgcctctccccgcgcgttggccgat
tcattaatgcagctggcacgacaggtttcccgactgg
aaagcgggcagtgagcgcaacgcaattaatgtg
agctcactcattaggcaccccaggctttacactttat
gcttccggctcgtatgttgtgtggaattgtgagcgga
taacaatttcacacaggaaacagctatgaccatgatt
acggattcactggccgtcgttttac
```

In still another embodiment, the lacI derivate gene is the lacI$^{Q1}$ gene having the nucleic acid sequence of SEQ ID NO. 12 (Table 13). The lacI$^{Q1}$ variant has a rearrangement which substitutes a −35 region whose nucleotide sequence exactly matches that of the *E. coli*—region consensus sequence, resulting in expression that is 100-fold higher than the native promoter in *E. coli*. See, for example, M P Colas & J H Miller, Mol. & Gen. Genet. 183(3): 559-60 (1980).

TABLE 13

NUCLEIC ACID SEQUENCE OF LACI$^{Q1}$ GENE

```
agcggcatgcatttacgttgacaccacctttcgcggt    SEQ ID NO. 12
atggcatgatagcgcccggaagagagtcaattcaggg
tggtgaatgtgaaaccagtaacgttatacgatgtcgc
agagtatgccggtgtctcttatcagaccgtttcccgc
gtggtgaaccaggccagccacgtttctgcgaaaacgc
gggaaaaagtggaagcggcgatggcggagctgaatta
cattcccaaccgcgtggcacaacaactggcgggcaaa
cagtcgttgctgattggcgttgccacctccagtctgg
ccctgcacgcgccgtcgcaaattgtcgcggcgattaa
atctcgcgccgatcaactgggtgccagcgtggtggtg
tcgatggtagaacgaagcggcgtcgaagcctgtaaag
cggcggtgcacaatcttctcgcgcaacgcgtcagtgg
gctgatcattaactatccgctggatgaccaggatgcc
attgctgtggaagctgcctgcactaatgttccggcgt
tatttcttgatgtctctgaccagacacccatcaacag
tattattttctcccatgaagacggtacgcgactgggc
gtggagcatctggtcgcattgggtcaccagcaaatcg
cgctgttagcgggcccattaagttctgtctcggcgcg
tctgcgtctggctggctggcataaatatctcactcgc
aatcaaattcagccgatagcggaacgggaaggcgact
ggagtgccatgtccggttttcaacaaaccatgcaaat
gctgaatgagggcatcgttcccactgcgatgctggtt
gccaacgatcagatggcgctgggcgcaatgcgcgcca
ttaccgagtccgggctgcgcgttggtgcggatatctc
ggtagtgggatacgacgataccgaagacagctcatgt
tatatcccgccgtcaaccaccatcaaacaggattttc
gcctgctggggcaaaccagcgtggaccgcttgctgca
actctctcagggccaggcggtgaaggcaatcagctg
ttgcccgtctcactggtgaaaagaaaaaccaccctgg
cgcccaatacgcaaaccgcctctccccgcgcgttggc
cgattcattaatgcagctggcacgacaggtttcccga
ctggaaagcgggcagtgagcgcaacgcaattaatgtg
agttagctcactcattaggcaccccaggctttacact
ttatgcttccggctcgtatgttgtgtggaattgtgag
cggataacaatttcacacaggaaacagctatgaccat
gattacggattcactggccgtcgttttac
```

In the present invention, the host cell chromosome can be modified by insertion of at least one nucleic acid sequence containing at least one copy of a gene encoding a LacI protein, the gene being capable of use by the cell to, preferably, constitutively express the encoded LacI protein, and the polynucleotide containing the gene being other than a PlacI-lacI-lacZYA nucleic acid sequence (i.e. a Plac(−) version of the PlacI-lacI-lacZYA operon) or a PlacI-lacI-lacZ polynucleotide (i.e. a structural lac utilization operon gene-containing portion of such a Plac(−) operon, such as an at least partially truncated version of a PlacI-lacI-lacZYA nucleic acid sequence).

The gene encoding the chosen LacI protein is preferably constitutively expressed. This may be accomplished by use of any promoter that is constitutively expressed in the selected expression host cell. For example, a native *E. coli* PlacI may be operably attached to the selected LacI coding sequence, or a different constitutively expressed promoter may be operably attached thereto. In some cases, a regulated promoter may be used, provided that the regulated promoter is maintained throughout fermentation in a state wherein the LacI protein is continually expressed there from. In a particular embodiment, a lac or tac family promoter is utilized in the present invention, including Plac, Ptac, Ptrc, PtacII, PlacUV5, lpp-PlacUV5, lpp-lac, nprM-lac, T7lac, T5lac, T3lac, and Pmac.

Genomic Insertion Sites

Chromosomal insertion may be performed according to any technique known in the art. For example, see: D S Toder, "Gene replacement in *Pseudomonas aeruginosa*," *Methods in Enzymology* 235:466-74 (1994); and J Quandt & M F Hynes, "Versatile suicide vectors which allow direct selection for gene replacement in Gram negative bacteria," *Gene* 127

(1):15-21 (1993). Transposon-type insertion techniques such as are known in the art, followed by selection, may also be used; see, e.g., I Y Goryshin & W S Reznikoff, "Tn5 in vitro transposition," *Journal of Biological Chemistry* 273(13):7367-74 (1998). Alternatively, gene transfection by (non-lytic) phage transduction may also be used for chromosomal insertion; see, e.g., J H Miller, *Experiments in Molecular Genetics* (1972) (Cold Spring Harbor Lab., NY).

Sites within the bacterial expression host cell chromosome that are useful places in which to insert the lacI gene(s), or derivative thereof, include any location that is are not required for cell function under the fermentation conditions used, for example within any gene whose presence, transcription, or expression is important for the healthy functioning of the cell under the fermentation conditions used. Illustrative examples of such insertion sites include, but are not limited to: sucrose import and metabolism genes (e.g., sacB), fructose import and catabolism genes (e.g., fructokinase genes, 1-phosphofructokinase genes), aromatic carbon source import and utilization genes (e.g., anthranilate operon genes, such as antABC genes, benzoate operon genes, as benABCD genes), beta-lactamase genes (e.g., ampC, blll, blc genes, blo genes, blp genes), alkaline phosphatase genes (e.g., phoA), nucleobase or nucleotide biosynthetic genes (e.g., pyrBCDEF genes), amino acid biosynthetic genes (e.g., proABC genes), aspartate semi-aldehyde dehydrogenase genes (e.g., asd), 3-isopropylmalate dehydrogenase genes (e.g., leuB), and anthranilate synthase genes (e.g., trpE).

In any embodiment in which the genomic insertion has resulted in or is concomitant with an auxotrophy, then either the host cell will be grown in media supplying an effective replacement metabolite to the cell to overcome (and avoid) the lethal effect, or a replacement gene will be provided in the host cell that expresses a biocatalyst effective to restore the corresponding prototrophy, e.g., as a selection marker gene. The gene or genes selected for deletion or inactivation (i.e. "knock-out") in constructing a metabolic auxotroph can be any gene encoding an enzyme that is operative in a metabolic pathway. The enzyme can be one that is involved in the anabolic biosynthesis of molecules that are necessary for cell survival. Alternatively, the enzyme can be one that is involved in the catabolic utilization of molecules that are necessary for cell survival. Preferably, all operative genes encoding a given biocatalytic activity are deleted or inactivated in order to ensure removal of the targeted enzymatic activity from the host cell in constructing the auxotrophic host cell. Alternatively, the host cell can exhibit a pre-existing auxotrophy (i.e. native auxotrophy), wherein no further genetic modification via deletion or inactivation (knock-out) need be performed.

For example, an amino acid biosynthetic gene (e.g., aproA, proB, or proC gene) or a nucleobase or nucleotide biosynthetic gene (e.g., pyrB, pyrC, pyrD, pyrE, or pyrF) may be used as the insertion site, in which case a necessary biosynthetic activity is normally disrupted, thus producing an auxotrophy. In such a case, either: 1) the medium is supplemented to avoid metabolic reliance on the biosynthetic pathway, as with a proline or uracil supplement; or 2) the auxotrophic host cell is transformed with a further gene that is expressed and thus replaces the biocatalyst(s) missing from the biosynthetic pathway, thereby restoring prototrophy to the cell, as with a metabolic selection marker gene such as proC, pyrF, or thyA. In a particular embodiment, the lacI transgene, or variant thereof, is inserted into a cell that is concomitantly or subsequently auxotrophically induced through the knock-out of a gene, or combination of genes, selected from the group consisting ofpyrF, thya, and proC. In a specific embodiment, a native *E. coli* lacI, lacI$^Q$, or lacI$^{Q1}$ transgene is inserted into a cell that is concomitantly or subsequently rendered auxotrophic through the knock-out of pyrF. In another specific embodiment, a native *E. coli* lacI, lacI$^Q$, or lacI$^{Q1}$ transgene is inserted into a cell that is concomitantly of subsequently rendered auxotrophic through the knock-out of proC. In still a further embodiment, a native *E. coli* lacI, lacI$^Q$, or lacI$^{Q1}$ transgene is inserted into a cell that is concomitantly or subsequently rendered auxotrophic through the knock-out of pyrF and proC.

In another embodiment, a native *E. coli* lacI, lacI$^Q$, or lacI$^{Q1}$ transgene, or derivative thereof, can be inserted into the Levansucrase locus of the host cell. For example, in one particular embodiment, a native *E. coli* lacI, lacI$^Q$, or lacI$^{Q1}$ transgene, or derivative thereof, can be inserted in the Levansucrase gene locus of *Pseudomonas fluorescens*. In particular, a native *E. coli* lacI, lacI$^Q$, or lacI$^{Q1}$ transgene, or derivative thereof, can be inserted into the Levansucrase gene locus of *Pseudomonas fluorescens* having the nucleic acid sequence of SEQ ID. NO. 13 (Table 14).

TABLE 14

| OPEN READING FRAME OF PF LEVAN SUCRASE GENE LOCUS |
|---|
| ctacccagaacgaagatcagcgcctcaatggcctcaa SEQ ID NO. 13 |
| ggttctactggtcgatgattcagccgaagtcgttgag |
| gtgctgaacatgctgctggaaatggaaggcgcccaag |
| tgagcgccttcagcgaccctttgagcgcgcttgaaac |
| agcccgggatgcccattacgacgtgattatttcggac |
| atcggcatgccgaaaatgaatggccatgagctgatgc |
| agaagctgcgtaaagtaggccaccttcgacaggctcc |
| cgccatcgccttaacgggctatggcgctggcaatgac |
| cagaaaaaggcgactgaatcgggctttaatgcgcatg |
| tcagcaaacccgttggccatgattcgctcatcaccct |
| gatcgaaaaactgtgccgctcccgccctaggcgtgg |
| ggcaggcgttcaagggtagatgaactgagaaaagcgc |
| acggacgcgcccgtttctggtcgcgacacctgggtat |
| ccacgctgcccaccgtgtcgctgcgcaaggtcaggta |
| caacacggcctggccggcgctgtcactcagcatccag |
| acgctcacaccctcccccggccgccctggccttgagcg |
| gctgaggctgcagcatctcgatattgaaaccgcgcag |
| cagctcaccgctcaactcgacctccaggggttcctgg |
| gccttaccttgcacatgaatcaccagcccatcggagg |
| cgccattgcgcaaaaagcgttggtactccacgcgcaa |
| ctgcccatcggcactgcgcacctcgcggctgctcagc |
| ggcccgctggaaaacagccctgccaagctcaagccga |
| tcagcaccagcagcgcgtaccaacccacccgctcaaa |
| gcgccagacccttgcgctgcaaggccatgttttcctgc |
| accggataattgcggctgtgtaagtcgtcagggtctg |
| ggttgttcatagcggggcccggactcaaccccttgctg |
| tgctcgggagaagacggcccccttggtgacaccccgtg |
| ggccggcaatcgcccatatcgcagcgcccagaaacgg |
| cagcaccacgactaccgcactccagcctgccttgctg |
| gccgaggcgttatcgctgcgccagatgctgttgatga |
| tccacgcatcgagcagtacgaggatcactgccaggcc |
| tatccagaagtaagtggtttgcatgatgcacctccag |
| gttatgtaacttttggtgcgcgggtgcgggcagggtt |
| cattatttttaggttctctgcctggcgcttggtttgc |
| cgccatcatgcgggcaacttcgccgatctacttaatg |
| atcgaacctcttcaaacaagacaagctgaaacgtctc |
| agctcctataaaaagccaaatcatgcacaaatgcatt |
| ttttgccttgaccacgggaatcgagtcttctaaagtc |
| aaatcactgtatatgaatacagtaatttgattccctt |
| catggacgagacttactatgaaaagcaccccttcgaa |
| atttggcaaaacaccccatcaacccagcctgtggacc |
| cgcgccgatgcgcttaaagtgcatgcggacgacccca |
| ccaccaccccagccgctggtcagcgcgaacttcccggt |
| attgagtgacgaggtgtttatctgggacaccatgccg |
| ctgcgtgatatcgacggcaacatcacctccgtcgatg |
| gctggtcggtgatcttcaccctcaccggcgatcgcca |
| cccgaacgacccgcaatacctcgatcagaatggcaac |
| tacgacgtcatccgcgactggaacgatcgccatggcc |
| gggcaaagatgtactactggttctcccgcaccggcaa |
| agactggaagctcggcggccgagtgatggctgaaggg |
| gtttcgcccaccgtgcgcgaatgggccggcacgccga |
| tcctgttgaacgagcaaggcgaagtagacctgtacta |
| caccgccgtcacgcccggcgcgaccatcgtcaaggtg |

TABLE 14-continued

OPEN READING FRAME OF PF LEVAN SUCRASE GENE LOCUS

```
cgtggccgcgtggtgaccaccgagcatggcgtcagcc
tggtgggctttgagaaggtcaagccgctgttcgaggc
ggacggcaagatgtaccagaccgaagcgcaaaatgcg
ttctggggcttcgcgatccatggccgttccgcgacc
cgaaagacggcaagctgtacatgctgttcgaaggtaa
cgtggccggcgaacgcggctcgcacaaggtcggtaaa
gccgaaatcggcgacgtgccgccaggttatgaagacg
tcggtaactcgcgcttccagactgcctgcgtcggtat
cgccgtggcccgcgacgaagacggcgacgactgggaa
atgctgccaccgctgctgaccgcggtgggcgtcaacg
accagaccgaacgcccgcacttcgtgttccaggacgg
caagtactacctgttcaccatcagccacaccttcacc
tacgccgacggcgtgaccggcccggacggcgtgtacg
gcttcgtcgccgattcgctgttcggtccgtatgtgcc
gttgaacggctctggtctggtactgggcaacccgtcc
tcccaaccgttccagacctactcgcactgcgtcatgc
ccaacggcctggtgacctccttcatcgacagcgtacc
gaccgacgacaccggcacgcagatccgtatcggcggc
accgaagcaccgacggtgggcatcaagatcaaaggc
agcaaacgtttgtggtcgctgagtatgactacggtta
catcccgccgatgctcgacgttacgctcaagtaaccg
gaggctatgaggtagcggctttgagctcgatgacaaa
cccgcggtgaatattcgctgcacctgtggcgagggag
cttgctcccggttgggccggacagccgccatcgcagg
caagccagctcccacatttggttcctggggcgtcag
ggaggtatgtgtcggctgaggggccgtcacgggagca
agctccctcgccacaggttcaacagcccattgggtgg
atattcaggaaatagaaatgcctgcaccattgagttg
agtc
```

IV. lacO Sequences

Attempts to repress the leakiness of a promoter must be balanced by the potential concomitant reduction in target recombinant polypeptide expression. One approach to further repress a promoter and reduce the leakiness of the promoters is to modify regulatory elements known as operator sequences, to increase the capacity of the associated repressor protein to bind to the operator sequence without reducing the potential expression of the target recombinant polypeptide upon induction.

It has been discovered that the use of a dual lac operator in *Pseudomonas fluorescens* offers superior repression of pre-induction recombinant protein expression without concomitant reductions in induced protein yields.

In one embodiment, a Pseudomonad organism is provided comprising a nucleic acid construct containing a nucleic acid comprising at least one lacO sequence involved in the repression of transgene expression. In a particular embodiment, the Pseudomonad host cell is *Pseudomonad fluorescens*. In one embodiment, the nucleic acid construct comprises more than one lacO sequence. In another embodiment, the nucleic acid construct comprises at least one, and preferably more than one, lacOid sequence. In one embodiment, the nucleic acid construct comprises a lacO sequence, or derivative thereof, located 3' of a promoter, and a lacO sequence, or derivative thereof, located 5' of a promoter. In a particular embodiment, the lacO derivative is a lacOid sequence.

In another embodiment of the present invention, nucleic acid constructs comprising more than one Zac operator sequence, or derivative thereof for use in a Pseudomonad host cell is provided. In one embodiment, at least one lac operator sequence may be a $lacO_{id}$ sequence.

The native *E. coli* Zac operator acts to down regulate expression of the lac operon in the absence of an inducer. To this end, the Zac operator is bound by the LacI repressor protein, inhibiting transcription of the operon. It has been determined that the LacI protein can bind simultaneously to two lac operators on the same DNA molecule. See, for example, Muller et al., (1996) "Repression of lac promoter as a function of distance, phase, and quality of an auxiliary lac operator," J. Mol. Biol. 257: 21-29. The repression is mediated by the promoter-proximal operator $O_1$ and the two auxiliary operators $O_2$ and $O_3$, located 401 base pairs downstream of $O_1$ within the coding region of the lacZ gene and 92 bp upstream of $O_1$, respectively (See FIG. 4). Replacement of the native *E. coli* Zac operator sequences with an ideal lac operator ($O_{id}$) results in increased repression of the native Zac operon in *E. coli*. See Muller et al., (1996) "Repression of Zac promoter as a function of distance, phase, and quality of an auxiliary Zac operator," J. Mol. Biol. 257: 21-29.

The lacO sequence or derivative can be positioned in the *E. coli* native $O_1$ position with respect to a promoter. Alternatively, the lacO sequence or derivative can be positioned in the *E. coli* $O_3$ position with respect to a promoter. In another embodiment, the lacO sequence or derivative can be located in the *E. coli* native $O_1$ position, the native $O_3$ position, or both with respect to a promoter. In one embodiment, the nucleic acid construct contains at least one ZacOid sequence either 5' to the promoter sequence or 3' to the promoter sequence. In a particular embodiment, the nucleic acid construct contains a lacOid sequence 3' of a promoter, and at least one lacO sequence, or derivative, 5' of a promoter. In an alternative embodiment, the nucleic acid construct contains a lacOid sequence 5' of a promoter, and at least one lacO sequence, or derivative, 3' of a promoter. In still another embodiment, the nucleic acid construct contains a ZacOid sequence both 5' and 3' of a promoter.

In a particular embodiment, the lacO sequence is lacOid represented by SEQ ID NO. 14, or a sequence substantially homologous. In another embodiment, a lacOid sequence of SEQ. ID. NO. 59, or a sequence substantially homologous to SEQ ID NO. 59 is employed.

TABLE 15

LACOID SEQUENCE

| | |
|---|---|
| 5'-AATTGTGAGCGCTCACAATT-3' | SEQ ID NO. 14 |
| 5'-tgtgtggAATTGTGAGCGCTCACAATTccacaca-3' | SEQ ID NO. 59 |

V. Isolated Nucleic Acids and Amino Acids

In another aspect of the present invention, nucleic acid sequences are provided for use in the improved production of proteins.

In one embodiment, nucleic acid sequences encoding prototrophy-restoring enzymes for use in an auxotrophic Pseudomonad host cells are provided. In a particular embodiment, nucleic acid sequences encoding nitrogenous base compound biosynthesis enzymes purified from the organism *Pseudomonas fluorescens* are provided. In one embodiment, nucleic acid sequences encoding the pyrF gene in *Pseudomonas fluorescens* is provided (SEQ. ID No.s 1 and 3). In another embodiment, a nucleic acid sequence encoding the thyA gene in *Pseudomonas fluorescens* is provided (SEQ. ID. No. 4). In still another embodiment, nucleic acid sequences encoding an amino acid biosynthetic compound purified from the organism *Pseudomonas fluorescens* are provided. In a particular embodiment, a nucleic acid sequence encoding the proC gene in *Pseudomonas fluorescens* is provided (SEQ. ID No.s 6 and 8).

In another aspect, the present invention provides novel amino acid sequences for use in the improved production of proteins.

In one embodiment, amino acid sequences of nitrogenous base compound biosynthesis enzymes purified from the organism *Pseudomonas fluorescens* are provided. In one embodiment, the amino acid sequence containing SEQ. ID No. 2 is provided In another embodiment, an amino acid sequence containing SEQ. ID. No. 5 is provided. In still another embodiment, amino acid sequences of an amino acid biosynthetic compound purified from the organism *Pseudomonas fluorescens* is provided. In a particular embodiment, an amino acid sequence containing SEQ. ID No. 7 is provided.

One embodiment of the present invention is novel isolated nucleic acid sequences of the *Pseudomonas fluorescens* pyrF gene (Table 2, Seq. ID No. 1; Table 4, Seq. ID No. 3). Another aspect of the present invention provides isolated peptide sequences of the *Pseudomonas fluorescens* pyrF gene (Table 3, Seq. ID No. 2). Nucleic and amino acid sequences containing at least 90, 95, 98 or 99% homologous to Seq. ID Nos. 1, 2, or 3 are provided. In addition, nucleotide and peptide sequences that contain at least 10, 15, 17, 20 or 25, 30, 40, 50, 75, 100, 150, 250, 350, 500, or 1000 contiguous nucleic or amino acids of Seq ID Nos 1, 2, or 3 are also provided. Further provided are fragments, derivatives and analogs of Seq. ID Nos. 1, 2, or 3. Fragments of Seq. ID Nos. 1, 2, or 3 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

Another embodiment of the present invention is novel isolated nucleic acid sequences of the *Pseudomonas fluorescens* thyA gene (Table 5, Seq. ID No. 4). Another aspect of the present invention provides isolated peptide sequences of the *Pseudomonas fluorescens* thyA gene (Table 6, Seq. ID No. 5). Nucleic and amino acid sequences containing at least 90, 95, 98 or 99% homologous to Seq. ID Nos. 4 or 5 are provided. In addition, nucleotide and peptide sequences that contain at least 10, 15, 17, 20 or 25, 30, 40, 50, 75, 100, 150, 250, 350, 500, or 1000 contiguous nucleic or amino acids of Seq. ID Nos 4 or 5 are also provided. Further provided are fragments, derivatives and analogs of Seq. ID Nos. 4 or 5. Fragments of Seq. ID Nos. 4 or 5 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

Another embodiment of the present invention is novel isolated nucleic acid sequences of the *Pseudomonas fluorescens* proC gene (Table 7, Seq. ID No. 6; Table 9, Seq. ID. No. 8). Another aspect of the present invention provides isolated peptide sequences of the *Pseudomonas fluorescens* proC gene (Table 8, Seq. ID No. 7). Nucleic and amino acid sequences containing at least 90, 95, 98 or 99% homologous to Seq. ID Nos. 6, 7, or 8 are provided. In addition, nucleotide and peptide sequences that contain at least 10, 15, 17, 20 or 25, 30, 40, 50, 75, 100, 150, 250, 350, 500, or 1000 contiguous nucleic or amino acids of Seq ID Nos 6, 7, or 8 are also provided. Further provided are fragments, derivatives and analogs of Seq. ID Nos. 6, 7, or 8. Fragments of Seq. ID Nos. 6, 7, or 8 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

Sequence Homology

Sequence homology is determined according to any of various methods well known in the art. Examples of useful sequence alignment and homology determination methodologies include those described below.

Alignments and searches for homologous sequences can be performed using the U.S. National Center for Biotechnology Information (NCBI) program, MegaBLAST. Use of this program with options for percent identity set at 70% for amino acid sequences, or set at 90% for nucleotide sequences, will identify those sequences with 70%, or 90%, or greater homology to the query sequence. Other software known in the art is also available for aligning and/or searching for homologous sequences, e.g., sequences at least 70% or 90% homologous to an information string containing a promoter base sequence or activator-protein-encoding base sequence according to the present invention. For example, sequence alignments for comparison to identify sequences at least 70% or 90% homologous to a query sequence can be performed by use of, e.g. the GAP, BESTFIT, BLAST, FASTA, and TFASTA programs available in the GCG Sequence Analysis Software Package (available from the Genetics Computer Group, University of Wisconsin Biotechnology Center, 1710 University Avenue, Madison, Wis. 53705), with the default parameters as specified therein, plus a parameter for the extent of homology set at 70% or 90%. Also, for example, the CLUSTAL program (available in the PC/Gene software package from Intelligenetics, Mountain View, Cal.) may be used.

These and other sequence alignment methods are well known in the art and may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, *Proc. Nat'l Acad. Sci. USA* 85:2444-48 (April 1988); the local homology method described in T. F. Smith & M. S. Waterman, in *Adv. Appl. Math.* 2:482-89 (1981) and in *J. Molec. Biol.* 147:195-97 (1981); the homology alignment method described in S. B. Needleman & C. D. Wunsch, *J. Molec. Biol.* 48(3):443-53 (March 1970); and the various methods described, e.g., by W. R. Pearson, in *Genomics* 11(3):635-50 (November 1991); by W. R. Pearson, in *Methods Molec. Biol.* 24:307-31 and 25:365-89 (1994); and by D. G. Higgins & P. M. Sharp, in *Comp. Appl'ns in Biosci.* 5:151-53 (1989) and in *Gene* 73(1): 237-44 (15 Dec. 1988).

Nucleic acid hybridization performed under highly stringent hybridization conditions is also a useful technique for obtaining sufficiently homologous sequences for use herein.

VI. Nucleic Acid Constructs

In still another aspect of the present invention, nucleic acid constructs are provided for use in the improved production of peptides.

In one embodiment, a nucleic acid construct for use in transforming a Pseudomonad host cell comprising a) a nucleic acid sequence encoding a recombinant polypeptide, and b) a nucleic acid sequence encoding a prototrophy-enabling enzyme is provided. In another embodiment, the nucleic acid construct further comprises c) a Plac-Ptac family promoter. In still another embodiment, the nucleic acid construct further comprises d) at least one lacO sequence, or derivative, 3' of a lac or tac family promoter. In yet another embodiment, the nucleic acid construct further comprises e) at least one lacO sequence, or derivative, 5' of a lac or tac family promoter. In one embodiment, the derivative lacO sequence can be a lacOid sequence. In a particular embodiment, the Pseudomonad organism is *Pseudomonas fluorescens*.

In one embodiment of the present invention, nucleic acid constructs are provided for use as expression vectors in Pseudomonad organisms comprising a) a nucleic acid sequence encoding a recombinant polypeptide, b) a Plac-Ptac family promoter, c) at least one lacO sequence, or derivative, 3' of a lac or tac family promoter, d) at least one lacO sequence, or derivative, 5' of a lac or tac family promoter. In one embodiment, the derivative lacO sequence can be a lacOid sequence. In one embodiment, the nucleic acid construct further comprises e) a prototrophy-enabling selection marker for use in an auxotrophic Pseudomonad cell. In a particular embodiment, the Pseudomonad organism is *Pseudomonas fluorescens*.

In one embodiment of the present invention, a nucleic acid construct is provided comprising nucleic acids that encode at least one biosynthetic enzyme capable of transforming an auxotrophic host cell to prototrophy. The biosynthetic enzyme can be any enzyme capable of allowing an auxotrophic host cell to survive on a selection medium that, without the expression of the biosynthetic enzyme, the host cell would be incapable of survival due to the auxotrophic metabolic deficiency. As such, the biosynthetic enzyme can be an enzyme that complements the metabolic deficiency of the auxotrophic host by restoring prototrophic ability to grow on non-auxotrophic metabolite supplemented media.

In one particular embodiment, the present invention provides a nucleic acid construct that encodes a functional orotodine-5'-phosphate decarboxylase enzyme that complements an pyrF(−) auxotrophic host. In a particular embodiment, the nucleic acid construct contains the nucleic acid sequence of SEQ ID NO. 1 or 3. In an alternative embodiment, the nucleic acid construct contains a nucleic acid sequence that encodes the amino acid sequence of SEQ ID NO. 2.

In another particular embodiment, the present invention provides a nucleic acid construct that encodes a functional thymidylate synthase enzyme that complements a thyA (−) auxotrophic host. In a particular embodiment, the nucleic acid construct contains the nucleic acid sequence of SEQ ID NO. 4. In an alternative embodiment, the nucleic acid construct contains a nucleic acid sequence that encodes the amino acid sequence of SEQ ID NO. 5.

In a further particular embodiment, the present invention provides a nucleic acid construct that encodes a functional $\Delta^1$-pyrroline-5-carboxylate reductase enzyme that complements a proC (−) auxotrophic host. In a particular embodiment, the nucleic acid construct contains the nucleic acid sequence of SEQ ID NO. 6 or 8. In an alternative embodiment, the nucleic acid construct contains the nucleic acid sequence that encodes the amino acid sequence of SEQ ID NO. 7.

In an alternative embodiment, the present invention provides a nucleic acid construct that encodes at least one biosynthetic enzyme capable of transforming an auxotrophic host cell to prototrophy and an additional non-auxotrophic selection marker. Examples of non-auxotrophic selection markers are well known in the art, and can include markers that give rise to colorimetric/chromogenic or a luminescent reaction such as lacZ gene, the GUS gene, the CAT gene, the luxAB gene, antibiotic resistance selection markers such as amphotericin B, bacitracin, carbapenem, cephalosporin, ethambutol, fluoroquinolones, isonizid, cephalosporin, methicillin, oxacillin, vanomycin, streptomycin, quinolines, rifampin, rifampicin, sulfonamides, ampicillin, tetracycline, neomycin, cephalothin, erythromycin, streptomycin, kanamycin, gentamycin, penicillin, and chloramphenicol resistance genes, or other commonly used non-auxotrophic selection markers.

In another embodiment, the expression vector can comprise more than one biosynthetic enzyme capable of transforming an auxotrophic host cell to prototrophy. The biosynthetic enzymes can be any enzymes capable of allowing an auxotrophic host cell to survive on a selection medium that, without the expression of the biosynthetic enzyme, the host cell would be incapable of survival due to the auxotrophic metabolic deficiency. As such, the biosynthetic enzymes can be enzymes that complement the metabolic deficiencies of the auxotrophic host by restoring prototrophic ability to grow on non-auxotrophic metabolite supplemented media. For example, an expression vector comprise a first and second prototrophy-enabling selection marker gene, allowing the host cell containing the construct to be maintained under either or both of the conditions in which host cell survival requires the presence of the selection marker gene(s). When only one of the marker-gene dependent survival conditions is present, the corresponding marker gene must be expressed, and the other marker gene(s) may then be either active or inactive, though all necessary nutrients for which the cell remains auxotrophic will still be supplied by the medium. This permits the same target gene, or the same set of covalently linked target genes, encoding the desired transgenic product(s) and/or desired transgenic activity(ies), to be maintained in the host cell continuously as the host cell is transitioned between or among different conditions. The coding sequence of each of the chosen selection marker genes independently can be operatively attached to either a constitutive or a regulated promoter.

In a particular embodiment, the nucleic acid vector comprises a nucleic acid construct that encodes a functional orotodine-5'-phosphate decarboxylase enzyme and a functional $\Delta^1$-pyrroline-5-carboxylate reductase enzyme that can complement a pyrF(−) auxotrophic host cell, a proC(−) auxotrophic host cell, or a pyrF(−)/proC(−) dual-auxotrophic host cell. In a particular embodiment, the nucleic acid construct comprises the nucleic acid sequences of SEQ ID NO. 1 or 3, and SEQ ID. NO. 6 or 8. In an alternative embodiment, the nucleic acid construct contains a nucleic acid sequence that encodes the amino acid sequences of SEQ ID NO. 2 and 7.

In an alternative particular embodiment, the nucleic acid vector comprises a nucleic acid construct that encodes a functional orotodine-5'-phosphate decarboxylase enzyme and a functional thymidylate synthase enzyme that can complement a pyrF(−) auxotrophic host cell, a thyA(−) auxotrophic host cell, or a pyrF(−)/thyA(−) dual-auxotrophic host cell. In a particular embodiment, the nucleic acid construct comprises the nucleic acid sequences of SEQ ID NO. 1 or 3, and SEQ ID. NO. 4. In an alternative embodiment, the nucleic acid construct contains a nucleic acid sequence that encodes the amino acid sequences of SEQ ID NO. 2 and 5.

In a particular embodiment, the nucleic acid vector comprises a nucleic acid construct that encodes a functional $\Delta^1$-pyrroline-5-carboxylate reductase enzyme and a thymidylate synthase enzyme that can complement a proC(−) auxotrophic host cell, a thyA(−) auxotrophic host cell, or a proC(−)/thyA(−) dual-auxotrophic host cell. In a particular embodiment, the nucleic acid construct comprises the nucleic acid sequences of SEQ ID NO. 4, and SEQ ID. NO. 6 or 8. In an alternative embodiment, the nucleic acid construct contains a nucleic acid sequence that encodes the amino acid sequences of SEQ ID NO. 5 and 7.

Promoters

In a fermentation process, once expression of the target recombinant polypeptide is induced, it is ideal to have a high level of production in order to maximize efficiency of the expression system. The promoter initiates transcription and is generally positioned 10-100 nucleotides upstream of the ribosome binding site. Ideally, a promoter will be strong enough to allow for recombinant polypeptide accumulation of around 50% of the total cellular protein of the host cell, subject to tight regulation, and easily (and inexpensively) induced.

The promoters used in accordance with the present invention may be constitutive promoters or regulated promoters. Examples of commonly used inducible promoters and their subsequent inducers include lac (IPTG), lacUV5 (IPTG), tac (IPTG), trc (IPTG), $P_{syn}$ (IPTG), trp (tryptophan starvation), araBAD (1-arabinose), lpp$^a$ (IPTG), lpp-lac (IPTG), phoA (phosphate starvation), recA (nalidixic acid), proU (osmolarity), cst-1 (glucose starvation), teta (tretracylin), cada (pH), nar (anaerobic conditions), PL (thermal shift to 42° C.), cspA (thermal shift to 20° C.), T7 (thermal induction), T7-lac operator (IPTG), T3-lac operator (IPTG), T5-lac operator (IPTG), T4 gene32 (T4 infection), nprM-lac operator (IPTG), $P_{syn}$ (alkyl-or halo-benzoates), Pu (alkyl-or halo-toluenes), Psal (salicylates), and VHb (oxygen). See, for example, Makrides, S. C. (1996) Microbiol. Rev. 60, 512-538; Hannig G. & Makrides, S. C. (1998) TIBTECH 16, 54-60; Stevens, R. C. (2000) Structures 8, R177-R185. See, e.g.: J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK).

A promoter having the nucleotide sequence of a promoter native to the selected bacterial host cell can also be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-faction regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a particular embodiment in which a regulated promoter is used, after growth of a desired quantity or density of host cell biomass, an appropriate effector compound is added to the culture in order to directly or indirectly result in expression of the desired target gene(s).

By way of example, where a lac family promoter is utilized, a lacI gene, or derivative thereof such as a lacI$^Q$ or lacI$^{Q1}$ gene, can also be present in the system. The lac gene, which is (normally) a constitutively expressed gene, encodes the Lac repressor protein (LacI protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-β-D-1-thiogalactopyranoside, also called "isopropylthiogalactoside").

In a particular embodiment, a lac or tac family promoter is utilized in the present invention, including Plac, Ptac, Ptrc, PtacII, PlacUV5, lpp-PlacUV5, lpp-lac, nprM-lac, T7lac, T5lac, T3lac, and Pmac.

Other Elements

Other regulatory elements can be included in an expression construct, including lacO sequences and derivatives, as discussed above. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed polypeptide, including His-tag, Flag-tag, T7-tag, S-tag, HSV-tag, B-tag, Strep-tag, polyarginine, polycysteine, polyphenylalanine, polyaspartic acid, (Ala-Trp-Trp-Pro)n (SEQ ID NO: 61), thioredoxin, beta-galactosidase, chloramphenicol acetyltransferase, cyclomaltodextrin gluconotransferase, CTP:CMP-3-deoxy-D-manno-octulosonate cytidyltransferase, trpE or trpLE, avidin, streptavidin, T7 gene 10, T4 gp55, Staphylococcal protein A, streptococcal protein G, GST, DHFR, CBP, MBP, galactose binding domain, Calmodulin binding domain, GFP, KSI, c-myc, ompT, ompA, pelB, NusA, ubiquitin, and hemosylin A.

At a minimum, a protein-encoding gene according to the present invention can include, in addition to the protein coding sequence, the following regulatory elements operably linked thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Starts of bacterial genes: estimating the reliability of computer predictions, Gene 234(2):257-65 (8 Jul. 1999); and B. E. Suzek et al., A probabilistic method for identifying start codons in bacterial genomes, Bioinformatics 17(12):1123-30 (December 2001). In addition, either native or synthetic RBSs may be used, e.g., those described in: EP 0207459 (synthetic RBSs), O. Ikehata et al., Primary structure of nitrile hydratase deduced from the nucleotide sequence of a *Rhodococcus* species and its expression in *Escherichia coli*, Eur. J. Biochem. 181(3):563-70 (1989) (native RBS sequence of AAG-GAAG. Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Vectors

Transcription of the DNA encoding the enzymes of the present invention by a Pseudomonad host can further be increased by inserting an enhancer sequence into the vector or plasmid. Typical enhancers are cis-acting elements of DNA, usually about from 10 to 300 bp in size that act on the promoter to increase its transcription.

Generally, the recombinant expression vectors will include origins of replication and selectable markers permitting transformation of the Pseudomonad host cell, e.g., the prototrophy restoring genes of the present invention, and a promoter derived from a highly-expressed gene to direct transcription of a downstream structural sequence. Such promoters have been described above. The heterologous structural sequence is assembled in appropriate phase with translation initiation and termination sequences, and in certain embodiments, a leader sequence capable of directing secretion of the translated polypeptide. Optionally, and in accordance with the present invention, the heterologous sequence can encode a fusion polypeptide including an N-terminal identification peptide imparting desired characteristics, e.g., stabilization or simplified purification of expressed recombinant product.

Useful expression vectors for use with *P. fluorescens* in expressing enzymes are constructed by inserting a structural DNA sequence encoding a desired target polypeptide together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable hosts for transformation in accordance with the present disclosure include various species within the genera *Pseudomonas*, and particularly particular is the host cell strain of *Pseudomonas fluorescens*.

Vectors are known in the art as useful for expressing recombinant proteins in host cells, and any of these may be modified and used for expressing the genes according to the present invention. Such vectors include, e.g., plasmids, cosmids, and phage expression vectors. Examples of useful plasmid vectors that can be modified for use on the present invention include, but are not limited to, the expression plasmids pBBR1MCS, pDSK519, pKT240, pML122, pPS10, RK2, RK6, pRO1600, and RSF1010. Further examples can include pALTER-Ex1, pALTER-Ex2, pBAD/His, pBAD/Myc-His, pBAD/gIII, pCal-n, pCal-n-EK, pCal-c, pCal-Kc, pcDNA 2.1, pDUAL, pET-3a-c, pET 9a-d, pET-11a-d, pET-12a-c, pET-14b, pET15b, pET-16b, pET-17b, pET-19b, pET-20b(+), pET-21a-d(+), pET-22b(+), pET-23a-d(+), pET24a-d(+), pET-25b(+), pET-26b(+), pET-27b(+), pET28a-c(+), pET-29a-c(+), pET-30a-c(+), pET31b(+), pET-32a-c(+), pET-33b(+), pET-34b(+), pET35b(+), pET-36b(+), pET-37b (+), pET-38b(+), pET-39b(+), pET-40b(+), pET-41a-c(+), pET-42a-c(+), pET43a-c(+), pETBlue-1, pETBlue-2, pET-Blue-3, pGEMEX-1, pGEMEX-2, pGEX1λT, pGEX-2T, pGEX-2TK, pGEX-3X, pGEX4T, pGEX-5X, pGEX-6P, pHAT10/11/12, pHAT20, pHAT-GFPuv, pKK223-3, pLEX, pMAL-c2X, pMAL-c2E, pMAL-c2g, pMAL-p2X, pMAL-p2E, pMAL-p2G, pProEX HT, pPROLar.A, pPROTet.E, pQE-9, pQE-16, pQE-30/31/32, pQE40, pQE-50, pQE-70, pQE-80/81/82L, pQE-100, pRSET, and pSE280, pSE380, pSE420, pThioHis, pTrc99A, pTrcHis, pTrcHis2, pTriEx-1, pTriEx-2, pTrxFus. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1):11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Formichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):14549 (Mar. 1, 1990); J. D. Jones & N. Gutterson, in Gene 61(3):299-306 (1987); M. Bagdasarian et al., in Gene 16(1-3):23747 (December 1981); H. P. Schweizer et al., in Genet Eng. (NY) 23:69-81 (2001); P. Mukhopadhyay et al., in J. Bact. 172(1): 477-80 (January 1990); D. O. Wood et al., in J. Bact. 145(3): 1448-51 (March 1981); and R. Holtwick et al., in Microbiology 147(Pt 2):33744 (February 2001).

Further examples of expression vectors that can be useful in *Pseudomonas* host cells include those listed in Table 16 as derived from the indicated replicons.

TABLE 16

SOME EXAMPLES OF USEFUL EXPRESSION VECTORS

| Replicon | Vector(s) |
|---|---|
| $_p$PS10 | $_p$CN39, $_p$CN51 |
| RSF1010 | $_p$KT261-3 |
| | $_p$MMB66EH |
| | $_p$EB8 |
| | $_p$PLGN1 |
| | $_p$MYC1050 |
| RK2/RP1 | $_p$RK415 |
| | $_p$JB653 |
| $_p$RO1600 | $_p$UCP |
| | $_p$BSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF1010 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid. Other exemplary useful vectors include those described in U.S. Pat. No. 4,680,264 to Puhler et al.

In a one embodiment, an expression plasmid is used as the expression vector. In another embodiment, RSF1010 or a derivative thereof is used as the expression vector. In still another embodiment, pMYC1050 or a derivative thereof, or pMYC1803 or a derivative thereof, is used as the expression vector.

VII. Expression of Recombinant Polypeptides in an Pseudomonad Host Cells

In one aspect of the present invention, processes of expressing recombinant polypeptides for use in improved protein production are provided.

In one embodiment, the process provides expression of a nucleic acid construct comprising nucleic acids encoding a) a recombinant polypeptide, and b) a prototrophy-restoring enzyme in a Pseudomonad that is auxotrophic for at least one metabolite. In an alternative embodiment, the Pseudomonad is auxotrophic for more than one metabolite. In one embodiment, the Pseudomonad is a *Pseudomonas fluorescens* cell. In a particular embodiment, a recombinant polypeptide is expressed in a Pseudomonad that is auxotrophic for a metabolite, or combination of metabolites, selected from the group consisting of a nitrogenous base compound and an amino acid. In a more particular embodiment, recombinant polypeptides are expressed in a Pseudomonad that is auxotrophic for a metabolite selected from the group consisting of uracil, proline, and thymidine. In another embodiment, the auxotrophy can be generated by the knock-out of the host pyrF, proC, or thyA gene, respectively. An alternative embodiment, recombinant polypeptides are expressed in an auxotrophic Pseudomonad cell that has been genetically modified through the insertion of a native *E. coli* lacI gene, lacI$^Q$ gene, or lacI$^{Q1}$ gene, other than as part of the PlacI-lacI-lacZYA operon, into the host cell's chromosome. In one particular embodiment, the vector containing the recombinant polypeptide expressed in the auxotrophic host cell comprises at least two lac operator sequences, or derivatives thereof. In still a further embodiment, the recombinant polypeptide is driven by a Plac family promoter.

In another embodiment, the process involves the use of Pseudomonad host cells that have been genetically modified to provide at least one copy of a LacI encoding gene inserted into the Pseudomonad host cell's genome, wherein the lacI encoding gene is other than as part of the PlacI-lacI-lacZYA operon. In one embodiment, the gene encoding the Lac repressor protein is identical to that of native *E. coli* lacI gene. In another embodiment, the gene encoding the Lac repressor protein is the lacI$^Q$ gene. In still another embodiment, the gene encoding the Lac repressor protein is the lacI$^{Q1}$ gene. In a particular embodiment, the Pseudomonad host cell is *Pseudomonas fluorescens*. In another embodiment, the Pseudomonad is further genetically modified to produce an auxotrophic cell. In another embodiment, the process produces recombinant polypeptide levels of at least about 3 g/L, 4 g/L, 5 g/L 6 g/L, 7 g/L, 8 g/L, 9 g/L or at least about 10 g/L. In another embodiment, the recombinant polypeptide is expressed in levels of between 3 g/L and 100 g/L.

The method generally includes:
a) providing a Pseudomonad host cell, preferably a *Pseudomonas fluorescens*, as described in the present invention,
b) transfecting the host cell with at least one nucleic acid expression vector comprising i) a target recombinant polypeptide of interest, and, in the case of the utilization of an auxotrophic host, ii) a gene encoding a prototrophy enabling enzyme that, when expressed, overcomes the auxotrophy of the host cell;
c) growing the host cell in a growth medium that provides a selection pressure effective for maintaining the nucleic acid expression vector containing the recombinant polypeptide of interest in the host cell; and
d) expressing the target recombinant polypeptide of interest.

The method can further comprise transfecting the host cell with at least once nucleic acid expression vector further comprising iii) a Plac family promoter, and optionally iv) more than one lac operator sequences. In one embodiment, at least one lac operator sequence may be a lacO$_{id}$ sequence. Preferably, the expression system is capable of expressing the target polypeptide at a total productivity of polypeptide of at least 1 g/L to at least 80 g/L. In a particular embodiment, the recombinant polypeptide is expressed at a level of at least 3 g/L, 4 g/L, 5 g/L, 6 g/L, 7 g/L, 8 g/L, 9 g/L, 10 g/L, 12 g/L, 15 g/L, 20 g/L, 25 g/L, 30 g/L, 35 g/L, 40 g/L, 45 g/L, 50 g/L, 60 g/L, 70 g/L, or at least 80 g/L. In a particular embodiment, a lac or tac family promoter is utilized in the present invention, including Plac, Ptac, Ptrc, PtacII, PlacUV5, lpp-PlacUV5, lpp-lac, nprM-lac, T7lac, T5lac, T3lac, and Pmac.

In one embodiment, at least one recombinant polypeptide can be expressed in a Pseudomonad cell that is auxotrophic for one metabolite, wherein the auxotrophy serves as a selection marker for the maintenance of the nucleic acid expression vector encoding the polypeptide of interest and the prototrophy-enabling enzyme. Alternatively, more than one recombinant polypeptide can be expressed in a Pseudomonad cell that is auxotrophic for one metabolite, wherein the nucleic acids encoding the recombinant polypeptides can be contained on the same vector, or alternatively, on multiple vectors.

In yet another embodiment, more than one expression vector encoding different target polypeptides can be maintained in a Pseudomonad host cell auxotrophic for at least one metabolite, wherein one expression vector contains a nucleic acid encoding a prototrophic-enabling enzyme and a first target polypeptide of interest, and a second expression vector contains a nucleic acid encoding an alternative, non-auxotrophic selection marker and a second polypeptide of interest.

In another embodiment, at least one recombinant polypeptide can be expressed in a Pseudomonad cell that is auxotrophic for more than one metabolite, wherein the multiple auxotrophies serve as selection markers for the maintenance of nucleic acid expression vectors. For example, an expression vector may be utilized in which a first and second prototrophy-enabling selection marker gene are present. If both marker genes are located on the same DNA construct, the host cell containing the construct may be maintained under either or both of the conditions in which host cell survival requires the presence of the selection marker gene(s). When only one of the marker-gene dependent survival conditions is present, the corresponding marker gene must be expressed, and the other marker gene(s) can then be either active or inactive, though all necessary nutrients for which the cell remains auxotrophic will still be supplied by the medium. This permits the same target gene, or the same set of covalently linked target genes, encoding the desired transgenic product(s) and/or desired transgenic activity(ies), to be maintained in the host cell continuously as the host cell is transitioned between or among different conditions. If each of the two selection marker genes is located on a different DNA construct, then, in order to maintain both of the DNA constructs in the host cell, both of the marker-gene dependent survival conditions are present, and both of the corresponding marker gene must be expressed. This permits more than one non-covalently linked target gene or set of target gene(s) to be separately maintained in the host cell. The coding sequence of each of the chosen selection marker genes independently can be operatively attached to either a constitutive or a regulated promoter.

Dual-target-gene examples of such a multi-target-gene system include, but are not limited to: (1) systems in which the expression product of one of the target genes interacts with the other target gene itself; (2) systems in which the expression product of one of the target genes interacts with the other target gene's expression product, e.g., a protein and its binding protein or the α-and β-polypeptides of an αn-βn protein; (3) systems in which the two expression products of the two genes both interact with a third component, e.g., a third component present in the host cell; (4) systems in which the two expression products of the two genes both participate in a common biocatalytic pathway; and (5) systems in which the two expression products of the two genes function independently of one another, e.g., a bi-clonal antibody expression system.

In one example of a dual-target-gene system of the above-listed type (1), a first target gene can encode a desired target protein, wherein the first target gene is under the control of a regulated promoter, the second target gene may then encode a protein involved in regulating the promoter of the first target gene, e.g., the second target gene may encode the first target gene's promoter activator or repressor protein. In an example in which the second gene encodes a promoter regulatory protein for the first gene, the coding sequence of the second gene can be under the control of a constitutive promoter. In one embodiment, the second gene will be part of a separate DNA construct that is a maintained in the cell as a high-copy-number construct with a copy number of at least 10, 20, 30, 40, 50, or more than 50 copies being maintained in the host cell.

In another embodiment, the present invention provides the use of more than one lacO sequence on an expression vector in the production of recombinant polypeptides in Pseudomonads, particularly in *Pseudomonas fluorescens*

In another aspect, the present invention provides a method of producing a recombinant polypeptide comprising transforming a bacterial host cell that is a member of the Pseudomonads and closely related bacteria having at least one chromosomally inserted copy of a Lac repressor protein encoding a lacI transgene, or derivative thereof such as $lacI^Q$ or $lacI^{Q1}$, which transgene is other than part of a whole or truncated structural gene containing PlacI-lacI-lacZYA construct with a nucleic acid construct encoding at least one target recombinant polypeptide. The nucleic acid encoding at least one target recombinant polypeptide can be operably linked to a Plac family promoter, in which all of the Plac family promoters present in the host cell are regulated by Lac repressor proteins expressed solely from the lacI transgene inserted in the chromosome. Optionally, the expression system is capable of expressing the target polypeptide at a total productivity of at least 3 g/L to at least 10 g/L. Preferably, the expression system is capable of expressing the target polypeptide at a total productivity of polypeptide of at least 3 g/L, 4 g/L, 5 g/L, 6 g/L, 7 g/L, 8 g/L, 9 g/L, or at least 10 g/L.

In one embodiment, the present invention provides a method of expressing recombinant polypeptides in an expression system utilizing auxotrophic Pseudomonads or related bacteria that have been further genetically modified to provide at least one copy of a LacI encoding gene inserted into the cell's genome, other than as part of the PlacI-lacI-lacZYA operon. In a particular embodiment, a recombinant polypeptide is expressed in an auxotrophic *Pseudomonas fluorescens* host cell containing a lacI transgene insert. In another particular embodiment, a recombinant polypeptide is expressed in an auxotrophic *Pseudomonas fluorescens* host cell containing a $lacI^Q$ transgene insert. In still another particular embodiment, a recombinant polypeptide is expressed in an auxotrophic *Pseudomonas fluorescens* host cell containing a $lacI^{Q1}$ transgene insert. The *Pseudomonas fluorescens* host can be auxotrophic for a biochemical required by the cell for survival. In a particular embodiment, the *Pseudomonas fluorescens* cell is auxotrophic for a nitrogenous base. In a particular embodiment, the *Pseudomonas fluorescens* is auxotrophic for a nitrogenous base selected from the group consisting of thymine and uracil. In a particularly particular embodiment, the *Pseudomonas fluorescens* host cell's auxotrophy is induced by a genetic modification to a pyrF or thyA gene rendering the associated encoded product non-functional. In an alternative embodiment, the *Pseudomonas fluorescens* cell is auxotrophic for an amino acid. In a particular embodiment, the *Pseudomonas fluorescens* is auxotrophic for the amino acid proline. In a particularly particular embodiment, the *Pseudomonas fluorescens* host cell's auxotrophy is induced by a genetic modification to a proC gene rendering the associated encoded product non-functional.

Transformation

Transformation of the Pseudomonad host cells with the vector(s) may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or $CaCll/Mg^{2+}$ treatment, or other well known methods in the art. See, e.g., Morrison, J. Bact., 132:349-351 (1977); Clark-Curtiss & Curtiss, Methods in Enzymology, 101:347-362 (Wu et al., eds, 1983), Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Selection

Preferably, cells that are not successfully transformed are selected against following transformation, and continuously during the fermentation. The selection marker can be an auxotrophic selection marker or a traditional antibiotic selection marker. When the cell is auxotrophic for multiple nutrient compounds, the auxotrophic cell can be grown on medium supplemented with all of those nutrient compounds until transformed with the prototrophy-restoring vector. Where the host cell is or has been made defective for multiple biosynthetic activities, the prototrophy-restorative marker system(s) can be selected to restore one or more or all of the biosynthetic activities, with the remainder being compensated for by continuing to provide, in the medium, the still-lacking nutrients. In selection marker systems in which more than one biosynthetic activity, and/or more than one prototrophy, is restored, the plurality of selection marker genes may be expressed together on one vector or may be co-expressed separately on different vectors. Even where a single metabolite is the target of the selection marker system, multiple biosynthetic activities may be involved in the selection marker system. For example, two or more genes encoding activities from the same anabolic pathway may be expressed together on one vector or may be co-expressed separately on different vectors, in order to restore prototrophy in regard to biosynthesis of the compound that is the product of the pathway.

Where the selection marker is an antibiotic resistance gene, the associated antibiotic can be added to the medium to select against non transformed and revertant cells, as well known in the art.

Fermentation

As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, a mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly particular.

Prior to transformation of the host cell with a nucleic acid construct encoding a prototrophic enabling enzyme, the host cell can be maintained in a media comprising a supplemental metabolite, or analogue thereof, that complements the auxotrophy. Following transformation, the host cell can be grown in a media that is lacking the complementary metabolite that the host cell is auxotrophic for. In this way, host cells that do not contain the selection marker enabling prototrophy are selected against. Likewise cells expressing recombinant proteins from expression vectors containing an antibiotic resistance selection marker gene can be maintained prior to transformation on a medium lacking the associated antibiotic used for selection. After transformation and during the fermentation, an antibiotic can be added to the medium, at concentrations known in the art, to select against non-transformed and revertant cells.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli, in J. Bact. 60:17-28 (1950)). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A particular mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 16 below. The components can be added in the following order: first (N)HPO$_4$, KH$_2$PO$_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose MgSO$_4$ and thiamine-HCL can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for high cell density cultivation (HCDC) for growth of *Pseudomonas* species and related bacteria. The HCDC can start as a batch process which is followed by two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of *Escherichia coli* at controlled specific growth rate" J Biotechnol: 20(1) 17-27.

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive.

Cell Density

An additional advantage in using *Pseudomonas fluorescens* in expressing recombinant proteins includes the ability of *Pseudomonas fluorescens* to be grown in high cell densities compared to *E. coli* or other bacterial expression systems. To this end, *Pseudomonas fluorescens* expressions systems according to the present invention can provide a cell density of about 20 g/L or more. The *Pseudomonas fluorescens* expressions systems according to the present invention can likewise provide a cell density of at least about 70 g/L, as stated in terms of biomass per volume, the biomass being measured as dry cell weight.

In one embodiment, the cell density will be at least 20 g/L. In another embodiment, the cell density will be at least 25 g/L, 30 g/L, 35 g/L, 40 g/L, 45 g/L, 50 g/L, 60 g/L, 70 g/L, 80 g/L, 90 g/L., 100 g/L, 110 g/L, 120 g/L, 130 g/L, 140 g/L, or at least 150 g/L.

In another embodiments, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

Expression Levels of Recombinant Protein

The expression systems according to the present invention can express transgenic polypeptides at a level at between 5% and 80% total cell protein (% tcp). In one embodiment, the expression level will be at or above 5%, 8%, 10%, 12%, 15%, 20%, 25%, 30%, 35%, 40%, 45%, 50%, 55%, 60%, 65%, 70%, 75%, or 80% tcp.

Isolation and Purification

The recombinant proteins produced according to this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); AK Patra et al., Protein Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example., Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QUIAGEN, Inc., Chatsworth, Calif.

Detection of the expressed protein is achieved by methods known in the art and includes, for example, radioimmunoassays, Western blotting techniques or immunoprecipitation.

The recombinantly produced and expressed enzyme can be recovered and purified from the recombinant cell cultures by numerous methods, for example, high performance liquid chromatography (HPLC) can be employed for final purification steps, as necessary.

Certain proteins expressed in this invention may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinknan Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

Alternatively, it is possible to purify the recombinant proteins or peptides from the host periplasm. After lysis of the host cell, when the recombinant protein is exported into the periplasm of the host cell, the periplasmic fraction of the bacteria can be isolated by cold osmotic shock in addition to other methods known to those skilled in the art. To isolate recombinant proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM $MgSO_4$ and kept in an ice bath for approximately 10 minutes. The cell suspension can be centrifuged and the supernatant decanted and saved. The recombinant proteins present in the supernatant can be separated from the host proteins by standard separation techniques well known to those of skill in the art.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed as described below.

Recombinant proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM immidazole. Immidazole can be removed by a final dialyzing step against PBS or 50 mM sodium acetate pH 6 buffer plus 200 mM NaCl. The purified protein can be stored at 4.degree. C. or frozen at −80.degree. C.

Other methods include, for example, those that may be described in MH Lee et al., Protein Expr. Purif., 25(1): p. 166-73 (2002), W. K. Cho et al., J. Biotechnology, 77(2-3): p. 169-78 (2000), Ausubel, et al. (1987 and periodic supplements), Deutscher (1990) "Guide to Protein Purification," Methods in Enzymology vol. 182, and other volumes in this series, Coligan, et al. (1996 and periodic Supplements) Current Protocols in Protein Science Wiley/Greene, NY, S. Roe, Protein Purification Techniques: A Practical Approach (Practical Approach Series), Oxford Press (2001); D. Bollag, et al., Protein Methods, Wiley-Lisa, Inc. (1996).

VI. Recombinant Polypeptides

The present invention provides improved protein production in bacterial expression systems. Examples of recombinant polypeptides that can be used in the present invention include polypeptides derived from prokaryotic and eukaryotic organisms. Such organisms include organisms from the domain Archea, Bacteria, Eukarya, including organisms from the Kingdom Protista, Fungi, Plantae, and Animalia.

Types of proteins that can be utilized in the present invention include non-limiting examples such as enzymes, which are responsible for catalyzing the thousands of chemical reactions of the living cell; keratin, elastin, and collagen, which are important types of structural, or support, proteins; hemoglobin and other gas transport proteins; ovalbumin, casein, and other nutrient molecules; antibodies, which are molecules of the immune system; protein hormones, which regulate metabolism; and proteins that perform mechanical work, such as actin and myosin, the contractile muscle proteins.

Other specific non-limiting polypeptides include molecules such as, e.g., renin, a growth hormone, including human growth hormone; bovine growth hormone; growth hormone releasing factor; parathyroid hormone; thyroid stimulating hormone; lipoproteins; alpha.1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin 13-chain; prorelaxin; mouse gonadotropin-associated peptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, 4, -5, or -6 (NT-3, NT-4, NT-5, or NT-6), or a nerve growth factor such as NGF-.beta.; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-.beta.1, TGF-.beta.2, TGF-.beta.3, TGF-.beta.4, or .TGF-.beta.5; insulin-like growth factor-I and -II (IGF-I and IGF-II); des(1-3)-IGF-I (brain IGF-I), insulin-like growth factor binding proteins; CD proteins such as CD-3, CD4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

The recombinant peptides to be expressed by according to the present invention can be expressed from polynucleotides in which the target polypeptide coding sequence is operably attached to transcription and translation regulatory elements to form a functional gene from which the host cell can express the protein or peptide. The coding sequence can be a native coding sequence for the target polypeptide, if available, but will more preferably be a coding sequence that has been selected, improved, or optimized for use in the selected expression host cell: for example, by synthesizing the gene to reflect the codon use bias of a *Pseudomonas* species such as *Pseudomonas fluorescens*. The gene(s) that result will have been constructed within or will be inserted into one or more vector, which will then be transformed into the expression host cell. Nucleic acid or a polynucleotide said to be provided in an "expressible form" means nucleic acid or a polynucleotide that contains at least one gene that can be expressed by the selected bacterial expression host cell.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank. GenBank is maintained by the National Institutes of Health, Bethesda, Md., and can be accessed at the NIH website. Additional information can also be obtained from GeneCards, an electronic encyclopedia integrating information about genes and their products and biomedical applications, made available by the Department of Molecular Genetics, the Weizmann Institute of Science, Rehovot, Israel. Nucleotide sequence information also can be obtained from the EMBL Nucleotide Sequence Database made available on the worldwide web by the European Bioinformatics Institute (Hinxton,Cambridge, UK) or from the DNA Databank of Japan (Research Organization of Information and Systems, National Institute of Genetics, Center for Information Biology and DNA Data Bank of Japan, 1111 Yata, Mishima, Shizuoka 411-8540, Japan). Additional sites for information on amino acid sequences include the Protein Information Resource website established by the National Biomedical Research Foundation, which includes Swiss-Prot.

EXAMPLES

Example 1

Construction of a pyrF Selection Marker System in a *P. fluorescens* Host Cell Expression System Reagents were acquired from Sigma-Aldrich (St. Louis Mo.) unless otherwise noted. LB is 10 g/L tryptone, 5 g/L yeast extract and 5 g/L NaCl in a gelatin capsule (BIO 101).

When required, uracil (from BIO100, Carlsbad Calif.) or L-proline was added to a final concentration of 250 ug/mL, and tetracycline was added to 15 ugniL. LB/5-FOA plates contain LB with 250 mM uracil and 0.5 mg/mL 5-fluoroorotic acid (5-FOA). M9 media consists of 6 g/L $Na_2HPO_4$, 3 g/L $KH_2PO_4$, 1 g/L $NH_4Cl$, 0.5 g/L NaCl, 10 mM $MgSO_4$, 1× HoLe Trace Element Solution, pH7. Glucose was added to a final concentration of 1%. The 1000× HoLe Trace Element Solution is 2.85 g/L $H_3BO_3$, 1.8 g/L $MnCl_2$ 4H2O, 1.77 g/L sodium tartrate, 1.36 g/L $FeSO_4.7H_2O$, 0.04 g/L $CoCl_2.6H_2O$, 0.027 g/L $CuCl_2.2H_2O$, 0.025 g/L $Na_2MoO_4.2H_2O$, 0.02 g/L $ZnCl_2$.

Oligonucleotides Used Herein

```
MB214pyrF1 (NotI site in bold)
                                         (SEQ ID NO: 60)
5'-GCGGCCGCTTTGGCGCTTCGTTTACAGG-3'

MB214pyrR1
(PvuI site in bold; KpnI site in underlined bold)
                                         (SEQ ID NO: 15)
5'-CGATCGGGTACCTGTCGAAGGGCTGGAGACAT-3' pyrFPstF (PstI site in bold)
                                         (SEQ ID NO: 16)
5'-AACTGCAGGATCAGTTGCGGAGCCTTGG-3' pyrFoverlap
                                         (SEQ ID NO: 17)
5'-TGCTCACTCTAAAAATCTGGAATGGGCTCTCAGGC-3' pyrFXbaR2 (XbaI site in bold)
                                         (SEQ ID NO: 18)
5'-GCTCTAGATGCGTGGCTGGATGAATGAA-3' pyrana1F
                                         (SEQ ID NO: 19)
5'-GGCGTCGAACAGGTAGCCTT-3' pyrana1R
                                         (SEQ ID NO: 20)
5'-CTCGCCTCCTGCCACATCAA-3'

M13F(-40)
                                         (SEQ ID NO: 21)
5'-CAGGGTTTTCCCAGTCACGA-3'
```

Cloning of a pyrF Gene from *P. fluorescens*

The pyrF gene was cloned from *P. fluorescens* by polymerase chain reaction (PCR) amplification, using primers MB214pyrF1 and MB214pyrR1 that bind 297 bp upstream from the pyrF gene start codon and 212 bp downstream of its stop codon, respectively. Restriction sites were included at the 5' ends of the primers to facilitate further cloning reactions The amplified region upstream of the pyrF open reading frame (ORF) was estimated as long enough to include the native promoter upstream of pyrF. A strong stem-loop structure at 14-117 bp downstream of the pyrF ORF, which may be a transcription terminator, was also included in the downstream flanking region.

To PCR-amplify the pyrF gene, the high-fidelity PROOF-START DNA polymerase was mixed in a 50 uL reaction volume containing buffer provided by the manufacturer (Qiagen, Valencia Calif.) 0.3 mM dNTPs (Promega, Madison, Wis.), 1 uM each of MB214pyrF1 and MB214pyrR1 primers, and about 0.3 μg of genomic DNA from *P. fluorescens* MB214. The amplification conditions were 5 min at 95° C., followed by 35 cycles of a 30 sec denaturation at 94° C., 30 sec annealing at 57° C., and a 2 min extension at 72° C., followed by a final step at 72° C. for 10 min. The reaction was separated on a 1% gel of SEAKEM GTG agarose (from BioWhittaker Molecular Applications, Rockland Me.). The expected 1.2 kb band was excised from the gel and purified by extraction on a ULTRAFREE-DA centrifugal gel nebulizer from Millipore (Bedford Mass.) column and de-salted into Tris-HCl buffer with a MICROBIOSPIN 6 P-6 polyacrylamide spin column (from Bio-Rad, Hercules Calif.).

The cloned gene contained a single ORF, encoding orotidine 5'phosphate decarboxylase. The identity of the gene was further confirmed as pyrF by its high similarity (P-value of $3.3×10^{-78}$) along the entire length of the gene (209 out of 232 residues) to the pyrF gene from *P. aeruginosa*, which had been previously reported (Strych et al., 1994). The *P. fluorescens* strain used was found to contain no other copies of anypyrF genes.

Sequencing was performed by The Dow Chemical Company. The pyrF sequence is presented within SEQ ID NO: 1.

Construction of a pyrF(−) *P. fluorescens*

To construct a pyrF(−) *P. fluorescens*, the cell's genomic pyrF gene was altered by deleting of the ORF between and including the gene's start and stop codons. The deletion was made by fusing in vitro the upstream and downstream regions flanking the pyrF region on a nonreplicating plasmid, then using allele exchange, i.e. homologous recombination, to replace the endogenous pyrF gene in MB101 with the deletion allele.

To construct the fusion of the flanking regions, the "Megaprimer" method (Barik 1997) was used, whereby the region upstream and then downstream of the desired deletion were subsequently amplified by PCR using an overlapping primer with homology on both sides of the desired deletion, so that the flanking regions become linked, leaving out the pyrF ORF. The upstream region was amplified from MB214 genomic DNA using the Proofstart polymerase (Qiagen) as described above, with the primers pyrFPstF and pyrFoverlap, and an extension time of 1 minute. After gel purification using binding to glass milk (GENECLEAN Spin Kit from Bio101, Carlsbad, Calif., USA), the 1 kB product was used as the "Megaprimer" for the second amplification.

Because there was difficulty amplifying the desired product in this second step, a template containing the genomic pyrF region was made by PCR amplification in order to increase the template quantity. HOTSTARTAQ DNA polymerase (from Qiagen, Valencia Calif.) was used with *P. fluorescens* genomic DNA and the pyrFPstF and pyrFXbaR2 primers. The Megaprimer and the pyrFXbaR2 primer were then used with this template and HOTSTARTAQ polymerase, to amplify the deletion product by PCR, using amplification conditions of 15 min at 95° C., followed by 30 cycles of a 30 sec denaturation at 94° C., 30 sec annealing at 59° C., and a 2 min extension at 72° C., followed by a final step at 72° C. for 3 min. The expected 2 kB band was separated from a number of other products by gel electrophoresis, and then gel purified as above and cloned into plasmid pCR2.1Topo (from Invitrogen, Carlsbad Calif.) according to instructions from the manufacturer, to form pDOW1215-7 Sequencing the PCR-amplified region of pDOW1215-7 showed that there were 3 mutations introduced by the amplification process; all three changes were within 112 bp downstream of the stop codon for pyrF. Sequencing through this area was difficult, because the process of the reaction stopped in this area. Analysis by M-FOLD (GCG) of the secondary structure of RNA that would be encoded by this area showed the presence of a very stable stem-loop structure and a run of uridine residues that is characteristic of a rho-independent transcription terminator. None of the mutations occurred in the open reading frame.

pDOW1215-7 was used to delete the chromosomal pyrF gene in MB101. To do this, first, electrocompetent P. fluorescens cells made according to the procedure of Artiguenave et al. (1997), were transformed with 0.5 µg of the purified plasmid. Transformants were selected by plating on LB medium with kanamycin at 50 µg/mL. This plasmid cannot replicate in P. fluorescens, therefore kanamycin resistant colonies result from the plasmid integrating into the chromosome. The site of integration of the plasmid was analyzed by PCR using the HOTSTARTAQ polymerase and primers pryanalF and M13F(−40), annealing at 57° C. and with an extension time of 4 min. One out of the 10 isolates (MB101::pDOW1215-7#2) contained an insertion of pDOW1215-7 into the downstream region (2.8 kB analytical product) and in the other nine were in the upstream region (2.1 kb analytical product).

Second, to identify strains that had lost the integrated plasmid by recombination between the homologous regions the following analytical PCR procedure was used: MB101::pDOW1215-7#2 was inoculated from a single colony into LB supplemented with 250 mM uracil, grown overnight, and then plated onto LB-uracil and 500 µg/mL 5-fluoroorotic acid (5-FOA—Zymo Research, Orange Calif.). Eight colonies were analyzed by PCR with HOTSTARTAQ and primers pyranalF and pyranalR, annealing at 57° C. and extending for 4 min. The expected size of the amplified product from the parent MB101 was 3.2 kB, or if the pyrF gene was deleted, then 2.5 kB. Each of the colonies gave rise to the 2.5 kB band expected from a deletion of pyrF. The first three isolates were purified and named PFG116, PFG117, and PFG118 (also known as DC36). The three isolates exhibit the phenotype expected from a pyrF deletion, i.e. they are sensitive to kanamycin, uracil is required for growth, and they are resistant to 5-FOA. The DNA sequence of PFG118 was identical to that of the amplified regions in pDOW1215-7; i.e. the three mutations in the stem-loop structure immediately downstream from pyrF were incorporated into the PFG118 genome, along with the pyrF deletion.

Use of the pyrF Gene as a Selection Marker in P. fluorescens Expression System

The ability of the pyrF gene to act as a selectable marker was tested by cloning it into a pMYC expression plasmid containing both an existing tetracycline resistance marker and the target enzyme coding sequence under the control of the tac promoter. For this, the plasmid pMYC5088 was digested at 37° C. for 2 hr with SnaBI in a 50 uL reaction using NEB Buffer 4 and 0.1 mg/mL of bovine serum albumen (BSA) (from New England Biolabs, Beverly Mass.). The reaction mixture was then treated at 70° C. for 20 min to inactivate the enzyme, then gel-purified as described above. 60 ng of the SnaBI-digested pMYC5088 was ligated to 50 ng of the MB214pyrF1-MB214pyrR1 PCR product using the FAST-LINK DNA Ligation Kit (Epicentre Technologies, Madison Wis.). After 1 hr at 25° C., the reaction was stopped by treating the mixture at 70° C. for 20 min. The result was then transformed into chemically-competent JM109 E. coli cells (Promega Corp., Madison Wis.) using conditions recommended by the manufacturer.

Figure 2:
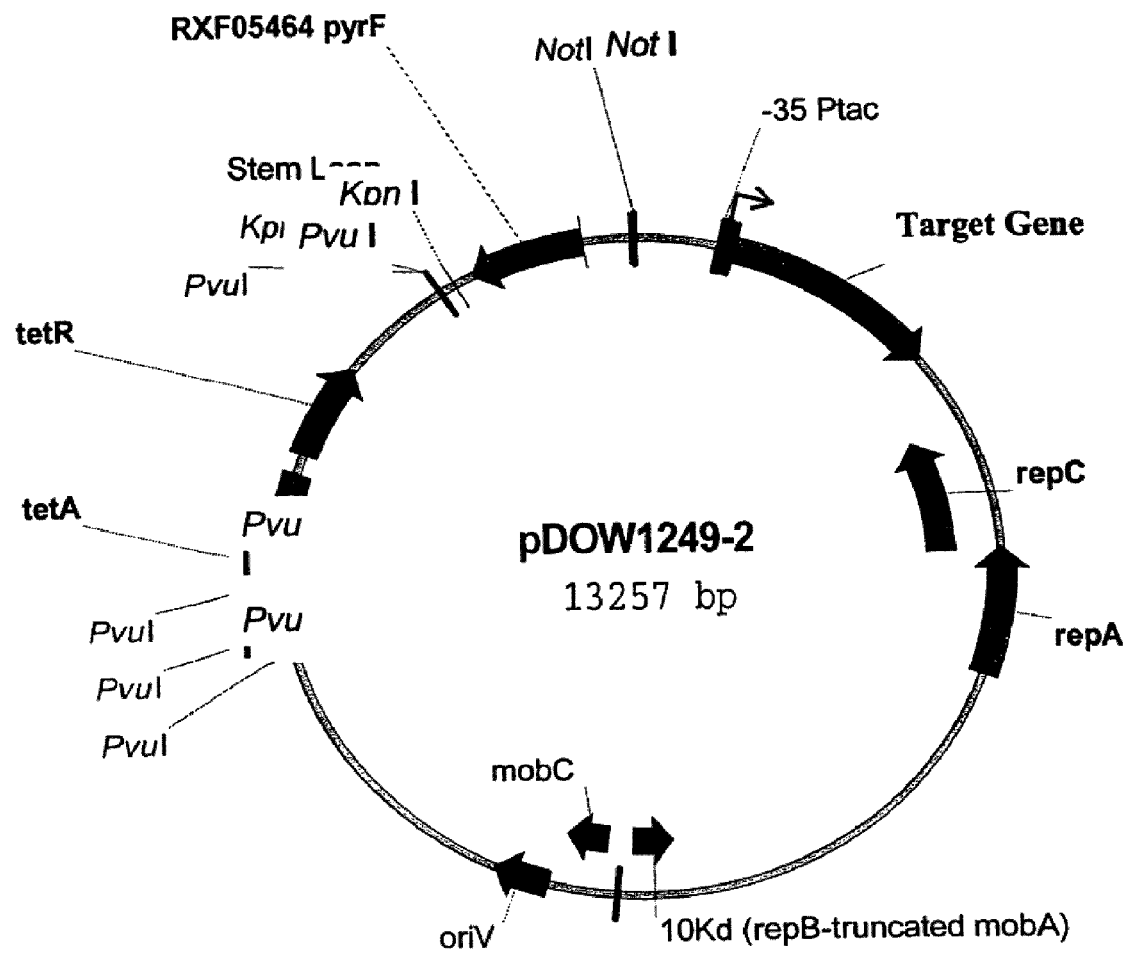
FIG. 2 represents a map of the plasmid pDOW1249-2.

Transformants were selected on LB medium containing tetracycline at 15 µg/mL. Plasmid DNA was prepared from 12 isolates using the QiaPrep Spin Miniprep Kit (Qiagen, Valencia Calif.) and screened with NotI and EcoRI, which indicated that one isolate contained the desired clone, pDOW1249-2 (FIG. 2). The plasmid pDOW1249-2 was transformed into pyrF(−) P. fluorescens containing a pCN plasmid containing a lacI repressor expression cassette and a kanamycin resistance marker gene. Isolates were tested in shake flasks and in 20-L fermentors.

Isolates were grown in minimal salts medium and kanamycin, but no tetracycline, so that the only selective pressure for the pDOW1249-2 plasmid was provided by the ability of the pyrF gene on the plasmid to complement the pyrF deletion in the chromosome. As determined by SDS-PAGE analysis, the amount of target protein produced by the new strain in the shake flask test was similar to that of the control strain, a genomically pyrF(+) P. fluorescens control system containing the same two plasmids, but for the absence of the pyrF gene in pDOW1249-2, and grown on the same medium but further supplemented with tetracycline in order to maintain the plasmid (data not shown). Two strains were chosen for further analysis at the 20-L scale, based on the amount of target protein seen on the SDS-PAGE gel and $OD_{575}$ values in shake flasks. Both strains showed a level of accumulation of target protein within the normal range observed for the control strain (FIG. 1).

Example 2

Construction of a pyrF-proC Dual Auxotrophic Selection Marker System in a P. fluorescens Host Cell Expression System Oligonucleotides Used Herein proC1
(SEQ ID NO: 22)
5'-ATATGAGCTCCGACCTTGAGTCGGCCATTG-3' proC2
(SEQ ID NO: 23)
5'-ATATGAGCTCGGATCCAGTACGATCAGCAGGTACAG-3' proC3
(SEQ ID NO: 24)
5'-AGCAACACGCGTATTGCCTT-3' proC5
(SEQ ID NO: 25)
5'-GCCCTTGAGTTGGCACTTCATCG-3' proC6
(SEQ ID NO: 26)
5'-GATAAACGCGAAGATCGGCGAGATA-3' proC7
(SEQ ID NO: 27)
5'-CCGAGCATGTTTGATTAGACAGGTCCTTATTTCGA-3' proC8
(SEQ ID NO: 28)
5'-TGCAACGTGACGCAAGCAGCATCCA-3' proC9
(SEQ ID NO: 29)
5'-GGAACGATCAGCACAAGCCATGCTA-3' genF2
(SEQ ID NO: 30)
5'-ATATGAGCTCTGCCGTGATCGAAATCCAGA-3' genR2
(SEQ ID NO: 31)
5'-ATATGGATCCGGCGTTGTGACAATTTACC-3'

XbaNotDraU2 linker
(SEQ ID NO: 32)
5'-TCTAGAGCGGCCGCGTT-3'

-continued

XbaNotDraL linker (SEQ ID NO: 33)
5'-GCGGCCGCTCTAGAAAC-3'

Cloning of proC from *P. fluorescens* and Formation of a pCN Expression Plasmid Containing proC Replacing Antibiotic Resistant Gene in pCN5lacI with proC The proC ORF and about 100 bp of adjacent upstream and downstream sequence was amplified from MB101 genomic DNA using proC1 and proC2, an annealing temperature of 56° C. and a 1 min extension. After gel purification of the 1 kB product and digestion with SacI, the fragment was cloned into SacI-digested pDOW1243 (a plasmid derived from pCN51lacI by addition of a polylinker and replacement of kanR with the gentamycin resistance gene), to create pDOW1264-2. This plasmid was tested in the proC(−) mutant strain PFG932 for its ability to regulate amylase synthesis from pDOW1249-2. Expressed target enzyme production levels at the 20-L scale was similar to that of the dual-antibiotic-resistance marker control strain DC88 (data not shown).

Figure 3:
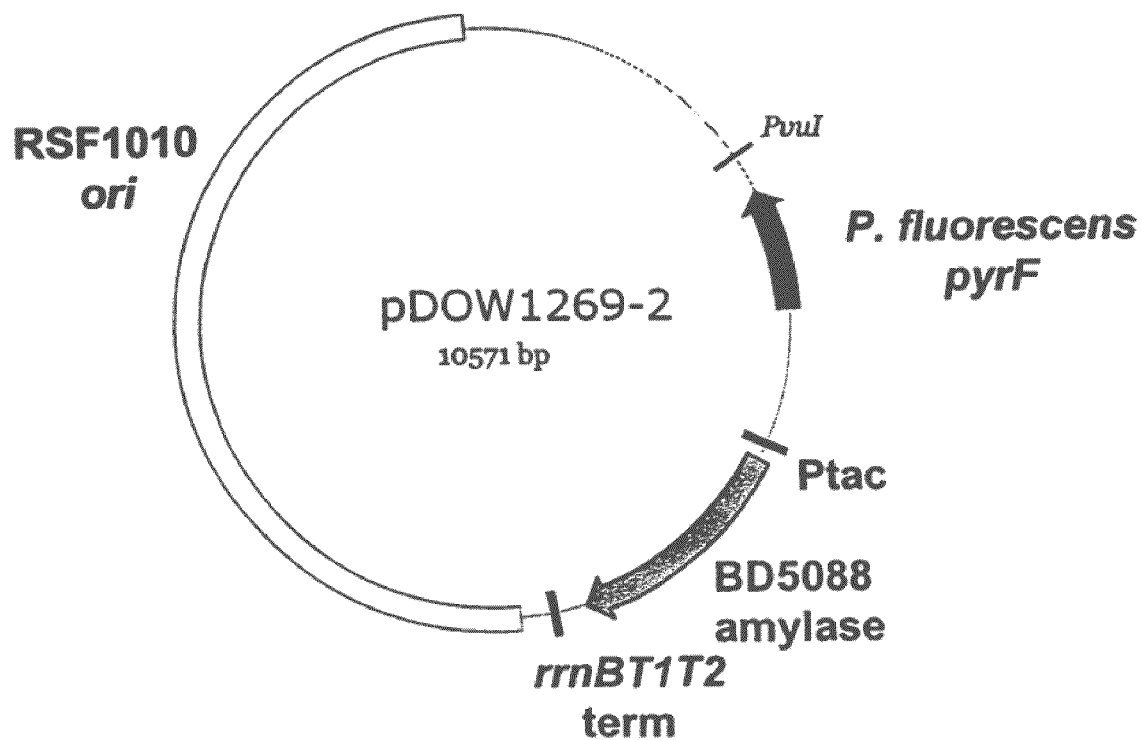
FIG. 3 represents a map of the plasmid pDOW1269-2.

The genR antibiotic marker gene was then removed from the pDOW1264-2 (FIG. 3) to create an antibiotic-marker-free plasmid with proC and lacI. Removing the genR gene was accomplished by restriction digestion of pDOW1264-2 with BamHI, purification of the 6.1 kB fragment, ligation to itself; and electroporation into the proC(−) *P. fluorescens* host PFG1016. Isolates were checked by restriction digestion using EcoRI. The resulting plasmid was named pDOW1306-6. Analytical restriction digests with EcoRI and sequencing across the BamHI junction verified the identity of the plasmid and the proper orientations of the genes therein.

Sequencing was performed by The Dow Chemical Company. The proC sequence is presented within SEQ ID NO:4.

Construction of Target Enzyme Expression Plasmid Containing a pyrF Marker in Place of an Antibiotic Resistance Marker The antibiotic-marker-free production plasmid, pDOW1269-2, containing a target enzyme-encoding gene under control of a tac promoter, was constructed by restriction digestion of pDOW1249-2 with PvuI to remove the tetR/tetA genes. Derived from pMYC5088 by insertion of the pyrF gene from MB214, pDOW1249-2 was prepared as described in Example 1. The 10.6 kB PvuI fragment was gel-purified, ligated to itself, transformed into PFG181 pCN51lacI by electroporation and spread on M9 glucose medium containing kanamycin (to retain the pCN51lacI). Plasmid DNA was isolated and analytical restriction digests with NcoI were carried out; two isolates showed a restriction digest that was consistent with the expected bands. Both isolates were sequenced across the PvuI junction, which verified the identity of the plasmids and the proper orientations of the genes therein.

Construction of a *Pseudomonas fluorescens* Strain with Genomic Deletions of pyrF and proC PFG118, a *P. fluorescens* MB101 strain with a deletion of pyrF, was described in Example 1.

Construction of pDOW1261-2, a Vector for Gene Replacement and Deletion

The vector pDOW1261-2 was designed to create clean deletions of genomic DNA, using marker exchange by the cross-in/cross-out method (Toder 1994; Davison 2002), by combining the following properties:

- a ColEI replication origin that functions only in *E. coli* and not in *P. fluorescens;*
- a selectable marker (tetR/tetA) for integration of the plasmid into the chromosome;
- a counterselectable marker (pyrF) that allows for selection for loss of the inserted plasmid (as long as the host strain is pyrF−); cells that lose the pyrF gene are resistant to 5-FOA; and
- a blunt-end cloning site, SrfI, which has an uncommon 8 bp recognition site—if the desired insert lacks the site, the efficiency of insertion can be increased by adding SrfI (Stratagene, La Jolla Calif.) to the ligation reaction to re-cleave vectors that ligate without an insert.

To construct this vector, a 5 kIB PstI to EcoRI fragment containing the tetR, tetA, and pyrF genes was cloned into pCRScriptCAM (Stratagene, La Jolla Calif.) that had been digested with PstI and EcoRI, creating pDOW1261-2.

Construction of a Vector to Delete proC from the Chromosome

To construct a deletion of proC, the copies of the flanking regions upstream and downstream of the proC gene were joined together by PCR, and then cloned into the pDOW1261-2 gene replacement vector. The proC7 primer, which bridges the proC ORF, was designed to delete the entire coding sequence from the ATG start codon to the TAG stop codon. An additional 16 bp downstream of the stop codon was also included in the deletion.

To make the PCR fusion of regions upstream and downstream from proC, the Megaprimer method of PCR amplification was used (Barik 1997). To make the megaprimer, the 0.5 kB region directly upstream of the proC open reading frame was amplified by PCR from MB214 genomic DNA, using primers proC5 and proC7. Primer proC7 overlaps the regions upstream and downstream of the proC ORF. The polymerase chain reaction was carried out with 1 uM of primers, 200 uM each of the four dNTPs, and Herculase high-fidelity polymerase (Stratagene, La Jolla Calif.) in the buffer recommended by the vendor. Herculase is a high-fidelity enzyme that consists mostly of Pfu polymerase, which leaves blunt ends. The amplification program was 95° C. for 2 min, 30 cycles of 95° C. for 30 sec, 50° C. for 30 sec, and 72° C. for 1 min per kB, followed by 10 min at 72° C. The amplified products were separated by 1% agarose gel electrophoresis in TBE and visualized using ethidium bromide. A gel slice containing the DNA was cut from the gel and purified as above The 1.3 kB region downstream from the proC gene was amplified using primers proC3 and proC6, to serve as a template for subsequent reactions. The same amplification protocol was used, except for an annealing temperature of 60° C. The reaction was checked on an agarose gel, and then purified using the StrataPrep PCR Purification Kit (Stratagene, La Jolla Calif.).

In the second step to make the deletion fusion, the megaprimer was used as one of the primers in a PCR reaction along with primer proC6, and with the proC3-proC6 PCR reaction as the template. An annealing temperature of 61° C. and extension time of 2 min was used. The 1 kB PCR product was purified and blunt-end ligated into the suicide vector pDOW1261-2 that had been digested with SrfI. SrfI was included in the ligation in order to decrease background caused by re-ligation of the vector, as according to instructions from the manufacturer (pCRScriptCam Cloning Kit—

Stratagene, La Jolla Calif.). The ligation was transformed into DH10 β (Gibco BRL Life Technologies, now Invitrogen, Carlsbad Calif.) by electroporation (2 mM gap cuvette, 25 μF, 2.25 kV, 200 Ohms) (Artiguenave et al. 1997), and isolates were screened using the DraIII restriction enzyme. The PCR amplified region of each isolate was sequenced by The Dow Chemical Company; isolate pDOW1305-6 was verified as containing the correct genomic DNA sequence.

Formation of the *P. fluorescens* pyrF-proC Double Deletion

To make a doubly deleted strain, PFG118 was transformed with pDOW1305-6 by electroporation as described above. Analytical PCR on the colonies with primers proC8 and the M13/pUC Reverse Sequencing Primer (−48) (which hybridizes to the plasmid only) (New England Biolabs, Beverly Mass.), using HotStarTaq (Qiagen, Valencia Calif.), an annealing temperature of 59° C. and an extension time of 4 min, showed that 9 out of 22 isolates had the plasmid integrated into the region upstream from proC, and 7 out of 22 had the plasmid integrated downstream (data not shown). Three of each orientation were purified to single colonies. The three isolates PFG118::1305-6.1, -6.8, -6.10 have an insertion in the region upstream, and the three isolates PFG118::1305-6.2, -6.3, -6.9 have an insertion in the region downstream.

To select for cells that have carried out a homologous recombination between the plasmid and the chromosome genes thereby leaving a deletion, PFG118::1305-6.1 and -6.2 were grown to stationary phase in 50 mL of LB with uracil and proline supplementation and then plated on LB-5-FOA with uracil and proline supplementation. Cells that lose the integrated plasmid by recombination also lose the pyrF gene, and are therefore expected to be resistant to 5-FOA which would otherwise be converted into a toxic compound. PCR analysis with proC8 and proC9 was carried out to distinguish between cells that had lost the plasmid and regenerated the original sequence, and those that had left the deletion. Two isolates with the expected 1.3 kB band were chosen from each of the two selections and named PFG1013, PFG1014, PFG1015 and PFG1016 (also known as DC164). All four isolates were unable to grow on M9 glucose unless both proline and uracil were added, and were tetracycline-sensitive. The genomic region of PFG118 (wild type proC) and PFG1016 (proC deletion) was amplified by PCR (primers proC8 and proC9, HotStarTaq polymerase, 63° C. annealing and 3 min extension) and sequenced. The region between proC5 and proC6 of strain PFG016 was identical to the parent, except for the expected 835 bp deletion.

Construction of a Dual Auxotrophic Selection Marker Expression System PFG1016/pDOW1306-6 pDOW1269-2

Plasmids were isolated from strain PFG118 pCN51lacI pDOW1269-2 by HISPEED Plasmid Midi Kit (Qiagen, Valencia Calif.). The pDOW1269-2 was partially purified from the pCN51lacI by agarose gel electrophoresis and then electroporated into PFG1016 pDOW1306-6. Transformants were selected on M9/glucose without supplementation. Because there was a possibility that some of the pCN51lacI contaminating the pDOW1269-2 preparation would also be cotransformed into the cells, three isolates from each transformation were tested for sensitivity to kanamycin, the antibiotic marker carried on pCN51lacI; all six were found sensitive. All six strains were found to express the target enzyme, in a test of target enzyme activity. PCR analysis showed that all six also contained the chromosomal proC deletion.

Restriction digestion of plasmids isolated from the transformants was consistent with the expected pattern.

Performance Testing of the Dual Auxotrophic Marker Expression System in Shake Flasks The six strains were then tested in shake flasks as described above in Example 1. Induction of target enzyme expression was initiated at 26 hours by addition of IPTG. The $OD_{575}$ for all six strains was comparable to that of the dual-antibiotic-resistance marker expression system control, DC88. Target enzyme production levels in all six were also comparable to that of the control, as assessed by SDS-PAGE. The two strains that achieved the highest $OD_{575}$, strains 1046 and 1048, were selected for further characterization.

Performance Testing of the Dual Auxotrophic Marker Expression System in 20-L Bioreactors Strains 1046 and 1048 were subsequently tested in 20-L bioreactors. Induction of target enzyme expression was initiated at 26 hours by addition of IPTG. Both strains achieved performance levels within the normal range for the DC88 control strain, for both $ODS_{575}$ and target enzyme activity. The performance averages of these two strains are shown in FIG. 1. Restriction digests of plasmids prepared from samples taken at the seed stage and at a time just before the 26-hour start of induction showed a pattern consistent with that expected. Analytical PCR of genomic DNA carried out on the same samples demonstrated the retention of the proC deletion and the pyrF deletion. Aliquots of the 25 hr samples were plated on tetracycline-, gentamycin-, or kanamycin-supplemented media; no cell growth was observed, thus confirming the absence of antibiotic resistance gene activity.

Analysis of strain 1046 (also known as DC167) in 20-L bioreactors was repeated twice with similar results. Plasmid stability at the seed stage and after 25 hours of fermentation (immediately before induction) was tested by replica plating from samples that had been diluted and plated on complete media. Both plasmids were present in more than 97% of the colonies examined, indicating the lack of cross feeding revertants able to survive without the plasmid and the stable maintenance of the expression vector in *Pseudomonas fluorescens*.

Results

Both of the pyrF expression systems performed as well as the control system in which only antibiotic resistance markers were used (FIG. 1). For the control strain, there is no negative effect of cross-feeding, since any importation of exogenous metabolites from lysed cells does not decrease or remove the selection pressures provided by the antibiotics in the medium. The expected decreases in performance expected as a result of cross-feeding on the two pyrF expression systems were surprisingly not observed.

Example 3

Chromosomal Integration of lacI, lacI$^Q$ and lacI$^{Q1}$ in *P. fluorescens*

Three *P. fluorescens* strains have been constructed, each with one of three different *Escherichia coli* lacI alleles, lacI (SEQ ID NO:9), lacI$^Q$ (SEQ ID NO:11), and lacI$^{Q1}$ (SEQ ID NO:12), integrated into the chromosome. The three strains exhibit differing amounts of LacI repressor accumulation. Each strain carries a single copy of its lacI gene at the levansucrase locus (SEQ ID NO:13) of *P. fluorescens* DC36, which is an MB101 derivative (see TD Landry et al., "Safety evaluation of an α-amylase enzyme preparation derived from the archaeal order Thermococcales as expressed in *Pseudomonas fluorescens* biovar I," *Regulatory Toxicology and Pharmacology* 37(1): 149-168 (2003)) formed by deleting the pyrF gene thereof, as described above.

No vector or other foreign DNA sequences remain in the strains. The strains are antibiotic-resistance-gene free and also contain a pyrF deletion, permitting maintenance, during growth in uracil un-supplemented media, of an expression plasmid carrying a pyrF+ gene. Protein production is completely free of antibiotic resistance genes and antibiotics.

MB214 contains the lacI-lacZYA chromosomal insert described in U.S. Pat. No. 5,169,760. MB214 also contains a duplication in the C-terminus of the LacI protein, adding about 10 kDa to the molecular weight of the LacI repressor.

Construction of Vector PDOW1266-1 for Insertion of Genes into the Levansucrase Locus Plasmid pDOW1266-1 was constructed by PCR amplification of the region upstream of and within the *P. fluorescens* gene for levansucrase (SEQ ID NO: 13), replacing the start codon with an XbaI site, using the Megaprimer method, see A Barik, "Mutagenesis and Gene Fusion by Megaprimer PCR," in B A White, *PCR Cloning Protocols* 173-182 (1997) (Humana). PCR was performed using HERCULASE polymerase (Stratagene, Madison Wis., USA) using primers LEV1 (SEQ ID NO:34) and LEV2 (SEQ ID NO:35), and *P. fluorescens* MB214 genomic DNA as a template (see below for oligonucleotide sequences). Primer LEV2 (SEQ ID NO:35) contains the sequence that inserts an XbaI site. The reaction was carried out at 95° C. for 2 min, 35 cycles of [95° C. for 30 sec, 58° C. for 30 sec, 72° C. for 1 min], followed by 10 min at 72° C. The 1 kB product was gel purified and used as one of the primers in the next reaction, along with LEV3 (SEQ ID NO:36), using MB214 genomic DNA as a template and the same conditions except that extension time was 2 min. The 2 kB product was gel purified and re-amplified with LEV2 (SEQ ID NO: 35) and LEV3 (SEQ ID NO. 36) in order to increase the quantity.

```
Oligonucleotides used
LEV1
                                       (SEQ ID NO: 34)
5'-TTCGAAGGGGTGCTTTTTCTAGAAGTAAGTCTCGTCCATGA LEV2
                                       (SEQ ID NO: 35)
5'-CGCAAGGTCAGGTACAACAC LEV3
                                       (SEQ ID NO: 36)
5'-TACCAGACCAGAGCCGTTCA LEV7
                                       (SEQ ID NO: 37)
5'-CTACCCAGAACGAAGATCAG LEV8
                                       (SEQ ID NO: 38)
5'-GACTCAACTCAATGGTGCAGG BglXbaLacF
                                       (SEQ ID NO: 39)
5'-AGATCTCTAGAGAAGGCGAAGCGGCATGCATTTACG lacIR4
                                       (SEQ ID NO: 40)
5'-ATATTCTAGAGACAACTCGCGCTAACTTACATTAATTGC Lacpro9
                                       (SEQ ID NO: 41)
5'-ATATTCTAGAATGGTGCAAAACCTTTCGCGGTATGGCATGA LacIQF
                                       (SEQ ID NO: 42)
5'-GCTCTAGAAGCGGCATGCATTTACGTTGACACC LacINXR
                                       (SEQ ID NO: 43)
5'-AGCTAGCTCTAGAAAGTTGGGTAACGCCAGGGT lacIQ1
                                       (SEQ ID NO: 44)
5'-AGTAAGCGGCCGCAGCGGCATGCATTTACGTTGACACCACCTTTCGC
GGTATGGCATG The Oligos Below were Used for Analytical
Sequencing Only
lacIF1
                                       (SEQ ID NO: 45)
5'-ACAATCTTCTCGCGCAACGC lacIF2
                                       (SEQ ID NO: 46)
5'-ATGTTATATCCCGCCGTTAA lacIR1
                                       (SEQ ID NO: 47)
5'-CCGCTATCGGCTGAATTTGA lacIR2
                                       (SEQ ID NO: 48)
5'-TGTAATTCAGCTCCGCCATC SeqLev5AS
                                       (SEQ ID NO: 49)
5'-TATCGAGATGCTGCAGCCTC SeqLev3S
                                       (SEQ ID NO: 50)
5'-ACACCTTCACCTACGCCGAC LEV10
                                       (SEQ ID NO: 51)
5'-TCTACTTCGCCTTGCTCGTT
```

The LEV2-LEV3 amplification product was cloned into the SrfI site of pDOW1261-2, a suicide vector that contains *P. fluorescens* pyrF+ gene as a selection marker to facilitate selection for cross-outs. The new plasmid was named pDOW1266-1. The amplified region was sequenced.

Cloning the lacI Genes into Insertion Vector PDOW1266-1

The *E. coli* lacI gene was amplified from pCN51lac with primers BgLZbaLacF (SEQ 10 NO:39) and lacIR4 (SEQ ID NO. 40), using HERCULASE polymerase (annealing at 62° C. and extension time of 2 min). After gel purification and digestion with XbaI, the lacI gene was cloned into the XbaI site of pDOW1266-1, to make pDOW1310. The laceQ gene was created by PCR amplification using pCN51lacI as a template with 15 primers lacpro9 (SEQ ID NO. 41) and lacIR4 (SEQ ID NO. 40), using HERCULASE polymerase (annealing at 62° C. and extension time of 2 min). After gel purification and digestion with XbaI, it was cloned into the XbaI site of pDOW1266-1, to make pDOW1311.

The lacI$^{Q1}$ gene was created by amplifying the lacI gene from *E. coli* K12 (ATCC47076) using primers lacIQ1 (SEQ ID NO. 44) and lacINXR (SEQ ID NO. 43) and cloned into pCR2.1Topo (Invitrogen, Carlsbad, Calif., USA), to make pCR2-lacIQ1. The lacI$^{Q1}$ gene was reamplified from pCR2-lacIQ1 using primers lacIQF (SEQ ID NO. 42) and lacINXR (SEQ ID NO. 43) with Herculase polymerase (61° C. annealing, 3 min extension time, 35 cycles). After gel purification and digestion with XbaI, the PCR product was cloned into the XbaI site of pDOW1266-1, to make pDOW1309.

The PCR amplified inserts in pCR2-lacIQ1, pDOW1310, pDOW1311, and pDOW1309 were sequenced (using primers lacIF1 (SEQ ID NO:45), lacIF2 (SEQ ID NO. 46), lacIR1 (SEQ ID NO. 47), lacIR2 (SEQ ID NO. 48), SeqLev5AS (SEQ ID NO. 49), SeqLev3S (SEQ ID NO. 50), and LEV10 (SEQ ID NO. 51)) to insure that no mutations had been introduced by the PCR reaction. In each case, an orientation was chosen in which the lacI was transcribed in the same direction as the levansucrase gene. Although the levansucrase promoter is potentially able to control transcription of lacI, the promoter would only be active in the presence of sucrose, which is absent in the fermentation conditions used.

Construction of *P. fluorescens* Strains with Intetrated lacI Genes at the Levansucrase Locus The vectors pDOW1309, pDOW1310, and pDOW1311 were introduced into DC36 by electroporation, first selecting for integration of the vector into the genome with tetracycline resistance. Colonies were screened to determine that the vector had integrated at the levansucrase locus by PCR with primers LEV7 (SEQ ID NO. 37) and M13R (from New England Biolabs, Gloucester Mass., USA). To select for the second cross-over which would leave the lacI gene in the genome, the isolates were grown in the presence of 5'-fluoroorotic acid and in the absence of tetracycline. Recombination between the duplicated regions in the genome either restores the parental genotype, or leaves the lacI gene. The resulting isolates were screened for sensitivity to tetracycline, growth in the absence of uracil, and by PCR with primers LEV7 (SEQ ID NO. 37) and LEV8 (SEQ ID NO. 38). The names of the new strains are shown in Table 17. To obtain sequence information for genomic regions, PCR products were sequenced directly, see E Werle, "Direct sequencing of polymerase chain reaction products," *Laboratory Methods for the Detection of Mutations and Polymorphisms in DNA* 163-174 (1997). For each strain, the sequencing confirmed the identity of the promoter, the orientation of the lacI variant relative to the flanking regions, and whether there were any point mutations relative to the parental sequence. The sequences of DC202 and DC206 were as expected. The sequence of DC204 showed a point mutation within the levansucrase open reading frame, downstream of lacI$^Q$, which did not change any coding sequence and therefore is inconsequential.

TABLE 17

*P. FLUORESCENS* STRAINS WITH LACI ALLELES INTEGRATED INTO THE GENOME

| Strain Designation | Plasmid used to make the lacI insertion | Genotype |
|---|---|---|
| DC202 | pDOW1310-1 | pyrF lev::lacI |
| DC204 | pDOW1311-4 | pyrF lev::lacI$^Q$ |
| DC206 | pDOW1309oriA | pyrF lev::lacI$^{Q1}$ |

Figure 5:
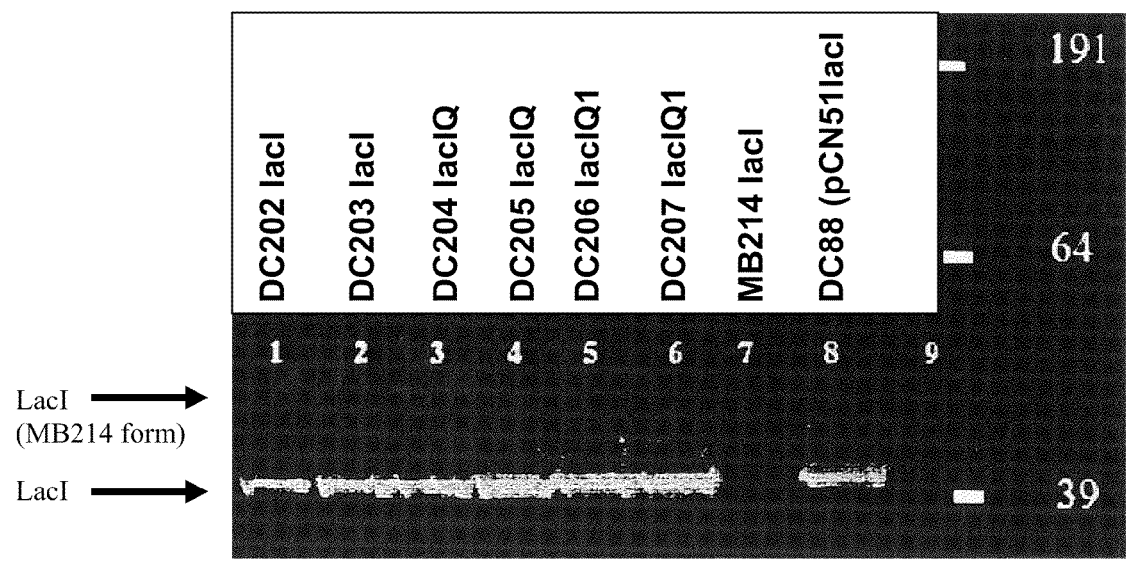
FIG. 5 represents a Western Blot analysis (InBlot) of LacI protein accumulation in the lacI integrant strains grown in a shake flask gene expression medium. Broth samples were normalized to OD600, combined with LDS NuPAGE sample buffer (Invitrogen), 50 mM DTT and heated at 95° C. for 40 min, then centrifuged briefly. Aliquots of 20 uL were loaded on a 10%, 1 mm NuPAGE Bis-Tris gel run in MOPS with antioxidant in the inner chamber. Detection of the LacI protein was accomplished with an in-gel hybridization method ("UnBlot", Pierce), using a polyclonal rabbit antibody to LacI (Stratagene cat. no. 217449-51) at 1:1000 and the secondary antibody, Stabilized Goat Anti-rabbit Horseradish Peroxidase Conjugated Antibody (Pierce) at 1:500. The horseradish peroxidase was visualized with UnBlot Stable Peroxide and UnBlot Luminol Enhancer as according to the UnBlot kit.

Analysis of Relative Concentration of LacI in the lacI Integrants, Compared to pCN51lacI UnBlot is a method analogous to Western analysis, in which proteins are detected in the gel without the need for transfer to a filter. The technique was carried out following the directions from Pierce Biotechnology (Rockford, Ill., USA), the manufacturer. Analysis using UniBlot showed that the amount of LacI in each of the new integrant strains was higher than in MB214. MB214 contains the lacI-lacZYA insert described in U.S. Pat. No. 5,169,760. The relative concentration of LacI in the lacI$^Q$ and lacI$^{Q1}$ integrants was about the same as in strains carrying pCN51lacI, the multi-copy plasmid containing lacI. See FIG. 5.

A dilution series was carried out in order to assess more precisely the relative difference in LacI concentration in MB214, DC202 (lacI integrated) and DC206 (lacI$^{Q1}$ integrated). MB101pCN51lacI, DC204 and DC206 have about 100 times more LacI than MB214, whereas DC202 has about 5 times more.

Example 4

Nitrilase Expression and Transcription

Strain DC140 was constructed by introducing into *P. fluorescens* MB214a tetracycline-resistant broad-host-range plasmid, pMYC 1803 (WO 2003/068926), into which a nitrilase gene (G DeSanthis et al., *J. Amer. Chem. Soc.* 125: 11476-77 (2003)), under the control of the Ptac promoter, had been inserted. In order to compare regulation of un-induced expression of the target gene in DC202 and DC206 with MB214, the same nitrilase gene was cloned onto a pMYC 1803 derivative where the tetracycline-resistance gene has been replaced by a pyrF selection marker. The new plasmid, pDOW2415, was then electroporated into DC202 and DC204, resulting in DC239 and DC240, respectively. DC140, DC239 and DC240 were cultured in 20 L fermentors by growth in a mineral salts medium fed with glucose or glycerol, ultimately to cell densities providing biomasses within the range of about 20 g/L to more than 70 g/L dry cell weight (See WO 2003/068926). The gratuitous inducer of the Ptac promoter, IPTG, was added to induce expression.

Figure 6:
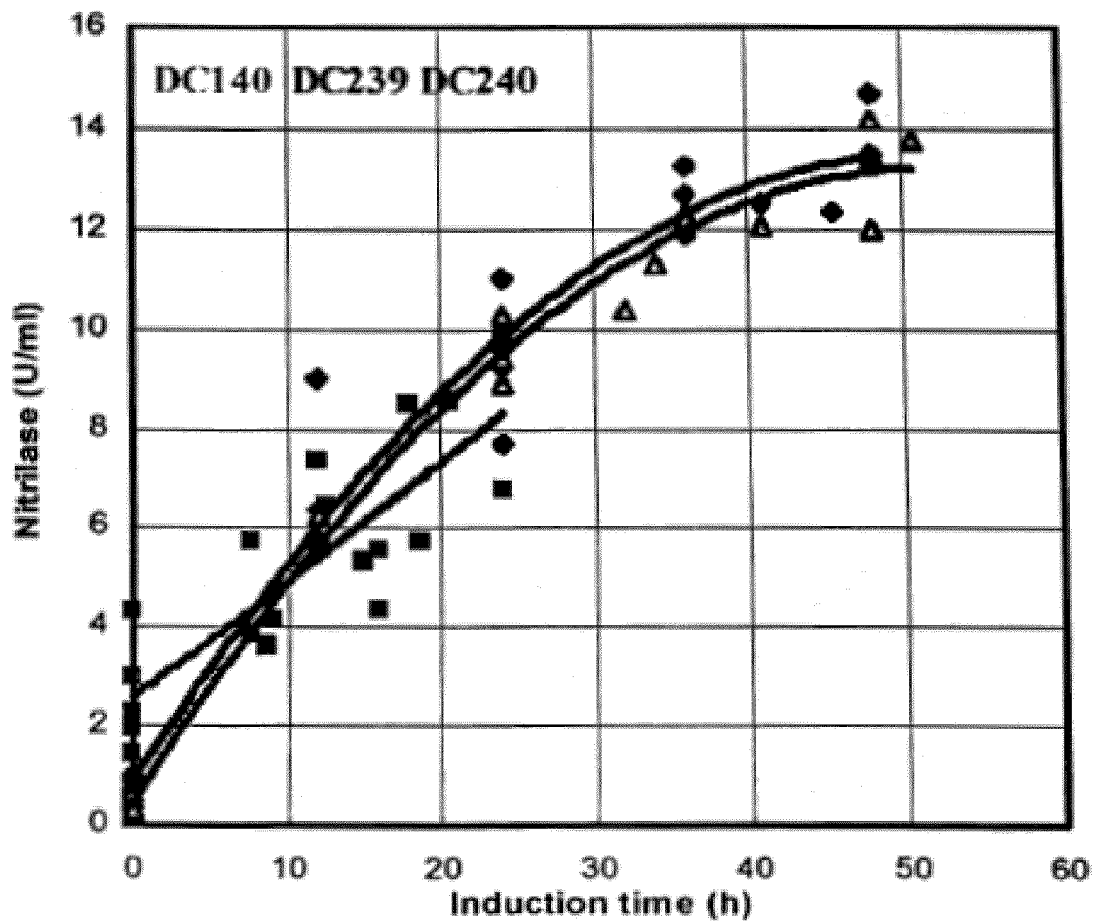
FIG. 6 represents the composite of nitrilase accumulation profiles of DC140, DC239 and DC240. Data were compiled from DC140 (n=5), DC239 (n=5) and DC240 (n=4) runs. Dc 140 is represented by ■. DC239 is represented by □. DC240 is represented by □. Fermentation runs were performed over a 48 hour period.

The ratio of pre-induction nitrilase activities of DC 140 to DC239 to DC240 was 6:2:1. RNA analysis by Northern blots of the same samples revealed the same ranking of de-repression. Based on densitometric measurements, the ratio of un-induced transcript levels of DC140:DC239:DC240 was 2A:1.4:1.0. Shortly after induction (30 min) with 0.3 mM IPTG, the levels of transcript of all the strains were the same. Post-induction nitrilase productivity rates were also comparable. This indicated that the concentration of inducer used was sufficient to fully induce the Ptac promoter in these three strains despite their different LacI protein levels. However, fermentations of the most derepressed strain, DC140, suffered significant cell lysis accompanied with loss of nitrilase activity after approximately 24 hours post-induction. Induction of the improved, more tightly regulated strains, DC239 and DC240, could be extended to more than 48 hours post induction, while maintaining high nitrilase productivity, with the ultimate result of a doubling of nitrilase yields. See FIG. 6.

Results

The examples indicate It that the use of a LacI-encoding gene other than as part of a whole or truncated Plac-lacI-lacZYA operon in Pseudomonads resulted in substantially improved repression of pre-induction recombinant protein expression, higher cell densities in commercial-scale fermentation, and higher yields of the desired product in comparison with previously taught lacI-lacZYA Pseudomonad chromosomal insertion (U.S. Pat. No. 5,169,760). The results also indicated that the lacI insertion is as effective in producing LacI repressor protein in *Pseudomonas fluorescens*, thereby eliminating the need to maintain a separate plasmid encoding a LacI repressor protein in the cell and reducing potential production inefficiencies caused by such maintenance.

In addition to being antibiotic free, derepression during the growth stage in DC239 and DC240 was up to 10 fold less than the MB214 strain. Pre-induction nitrilase activity levels of DC239 and DC240 averaged 0.4 U/ml in more than 13 separate fermentations, and cell density and nitrilase expression in DC239 and DC240 did not decay during extended induction phase, as it did in DC140. Given the higher derepression, DC239 and DC240 fermentation runs decreased the time of the growth phase by more than 30%, reducing fermentation costs.

Example 5

Figure 4:
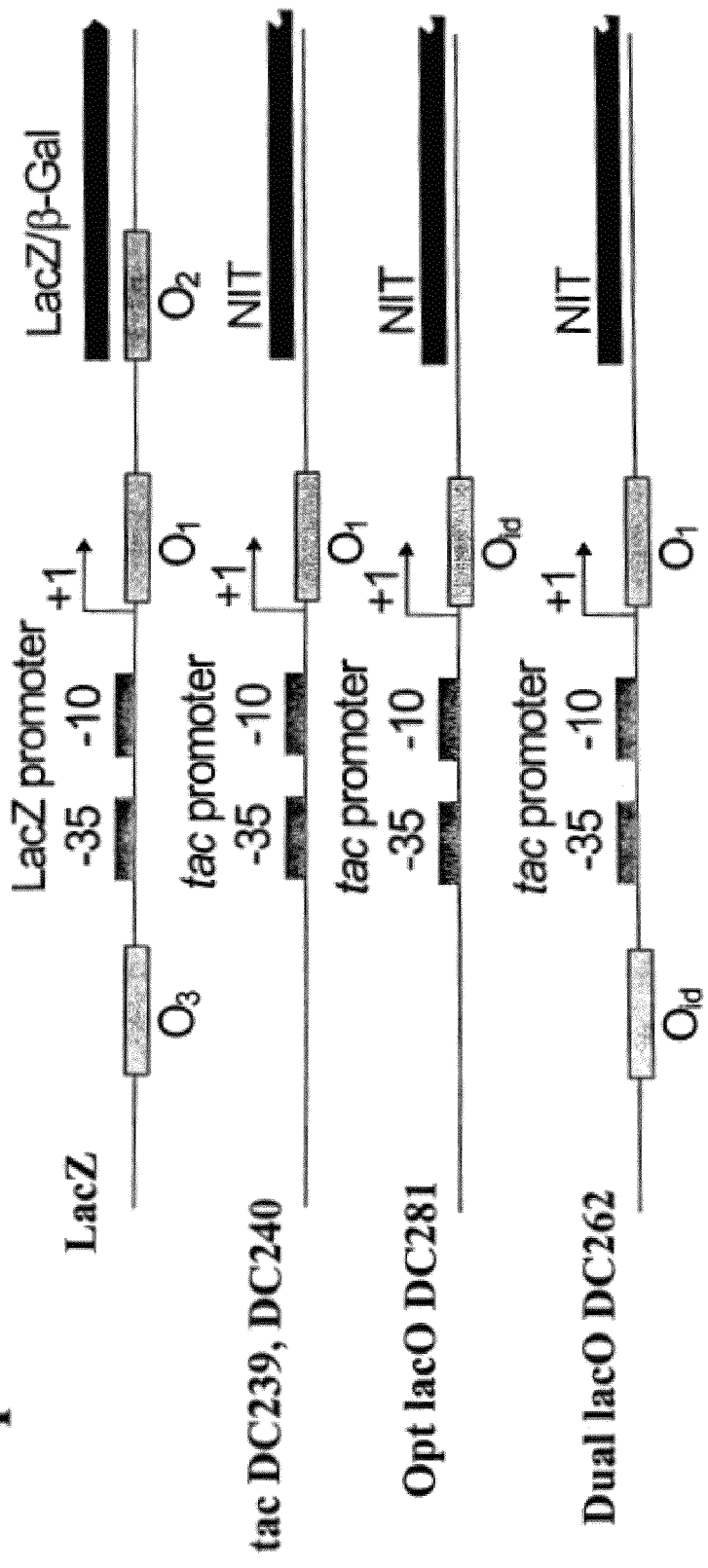
FIG. 4 represents a schematic of lac operator constructs. LacZ represents the positions of the native E. coli lacO sequences. tac DC239, DC240 represents the position of the native E. coli lac operator on a construct comprising a tac promoter and a nitrilase encoding nucleic acid. Opt lacO DC281 represents the position of the lacOid operator sequence on a construct comprising a tac promoter and a nitrilase encoding nucleic acid. Dual lacO DC262 represents the position of a lacOid operator sequence 5' (SEQ ID NO: 14), and wild type lac operator sequence 3' (SEQ ID NO: 62) of a tac promoter on a construct further comprising a nitrilase encoding nucleic acid.

Construction of tac Promoter with a Single Optimal lac Operator and with two Zac Operators The native tac promoter only has a single native lac operator, AATTGTGAGCGGATAACAATT (SEQ ID NO: 62), at the O1 position (FIG. 4). In the first construct, pDOW1418, the native operator was replaced by the more symmetrical lacOid operator sequence 5'-AATTGTGAGC GCTCA-CAATT-3' (SEQ. ID. NO. 14) (JR. Sadler, H. Sasmor and JL. Betz. PNAS. 1983 November; 80 (22): 6785-9). A 289 bp HindIII/SpeI fragment containing the tac promoter and the native lacO sequence was removed from a pMYC1803 derivative, pDOW2118, and replaced by a HindIII/SpeI fragment isolated from an SOE PCR amplification product containing the symmetrical lacOid sequence. The SOE PCR primers (RC-3 and RC-9) incorporated 4 nucleotide changes that produced the optimized/symmetrical lacO sequence (three base pair substitutions and one base pair deletion). The HindIII/SpeI promoter fragment of the resulting plasmid, pDOW2201, was cloned into the nitrilase expression plasmid based on pMYC1803, to replace the native tac promoter, resulting in pDOW1414. This expression cassette was then transferred onto the pyrF(+) plasmid pDOW1269, resulting in pDOW1418 by exchanging DraI/XhoI fragments. Plasmid pDOW1418 was then transformed into host strain DC206, resulting in strain DC281 (See FIG. 4).

```
Oligonucleotides used
RC-3
                                            (SEQ ID NO: 52)
5'-GTGAGCGCTCACAATTCCACACAGGAAAACAG RC-4
                                            (SEQ ID NO: 53)
5'-TTCGGGTGGAAGTCCAGGTAGTTGGCGGTGTA RC-9
                                            (SEQ ID NO: 54)
5'-GAATTGTGAGCGCTCACAATTCCACACATTATACGAGC RC-10
                                            (SEQ ID NO: 55)
5'-ATTCAGCGCATGTTCAACGG
```

In the second construct, pDOW1416, the lacOid operator, 5'-AATTGTGAGC GCTCACAATT-3' (SEQ ID. No. 14), was inserted 52 nucleotides up-stream (5') of the existing native lacO1 by PCR. PCR amplification of the promoter region using the Megaprimer method was performed using a pMYC1803 derivative, pMYC5088, and the following primers AKB-1 and AKB-2 as a first step. The resulting PCR product was combined with primer AKB-3 in a second round of PCR amplification using the same template. After purification and digestion with HindIII and SpeI, the promoter fragment containing the dual operators was cloned into the HindIII and SpeI sites of plasmid pMYC5088 resulting in pDOW1411. Intoduction of the second operator introduced a unique MfeI site immediately upstream of the optimal operator. The XhoI/SpeI vector fragment with promoter regions of pDOW1411 was then ligated with the compatible fragment of the pMYC1803 derivative bearing the nitrilase gene, forming pDOW1413. Subsequent ligation of the MfeI/XhoI expression cassette fragment of pDOW1413 to the compatible vector fragment of pDOW1269 resulted in pDOW1416; which when transformed into DC206, formed the strain DC262.

```
Oligonucleotides used
AKB-1
                                            (SEQ ID NO: 56)
5'-ACGGTTCTGGCAAACAATTGTGAGCGCTCACAATTTATTCTGAAATG
AGC AKB-2
                                            (SEQ ID NO: 57)
5'-GCGTGGGCGGTGTTTATCATGTTC AKB-3
                                            (SEQ ID NO: 58)
5'-TACTGCACGCACAAGCCTGAACA
```

Nitrilase Derepression

Northern blot analysis was performed pre and post induction on MB214, DC202, and DC206. MB214, DC202, and DC206 were transformed with a nitrilase expression vector containing the wild type lacO sequence in the $O_1$ position 3' of the tac promoter, creating MB214 wt$O_1$, DC202 wt$O_1$ (DC239), and DC206 wt$O_1$ (DC240), as described above. DC206 was transformed with a nitrilase expression vector containing a lacOid sequence in place of the wild type laco sequence at the $O_1$ position 3' of the tac promoter as described above, creating DC206Oid (DC281). DC206 was also transformed with a nitrilase expression vector containing a wild type lacO sequence at the $O_1$ position 3' of the tac promoter and a lacOid sequence at the $O_3$ position 5' of the tac promoter, creating the dual lacO containing DC206 wt$O_1$ $O_3$id (DC263).

Northern blot analysis indicated a greater repression by the strain containing the Dual lacO sequence (DC206 wt$O_1$ $O_3$id (DC263)) cassette prior to induction. The greater repression of pre-induction expression is especially useful when producing toxic proteins, since basal levels of pre-induction toxic proteins result in the delayed entry of the cell into the growth phase, and, potentially, lower overall yields of the product.

We claim:

1. A process for the production of a recombinant polypeptide, the process comprising:
   a) providing an auxotrophic *Pseudomonas fluorescens* host cell, wherein said host cell comprises a lacI gene inserted into the chromosome;
   b) introducing into said host cell a nucleic acid construct comprising:
      i) a first nucleotide sequence encoding said recombinant polypeptide, wherein said first nucleotide sequence is operably linked to a promoter capable of directing expression of the first nucleotide sequence in said *Pseudomonas fluorescens* host cell; and
      ii) a second nucleotide sequence encoding an auxotrophic selection marker wherein said second nucleotide sequence is operably linked to a promoter, wherein the auxotrophic selection marker is a polypeptide that restores prototrophy to the auxotrophic host cell; and
   c) growing the auxotrophic *Pseudomonas fluorescens* host cell comprising the first and the second nucleotide sequences on a medium that lacks a metabolite for which the host cell is auxotrophic, wherein the auxotrophic selection marker encoded by the second nucleotide sequence and the recombinant polypeptide encoded by the first nucleotide sequence are expressed, and wherein the auxotrophic *Pseudomonas fluorescens* host cell is: auxotrophic for uracil, wherein the polypeptide that restores prototrophy is orotidine-5'-phosphate decarboxylase; auxotrophic for proline, wherein the polypeptide that restores prototrophy is $\Delta^1$-pyrroline-5-carboxylate reductase; or both; and: wherein when the auxotrophic *Pseudomonas fluorescens* host cell is auxotrophic for uracil, the metabolite is uracil; wherein when the auxotrophic *Pseudomonas fluorescens* host cell is auxotrophic for proline, the metabolite is proline; and wherein when the auxotrophic *Pseudomonas fluorescens* host cell is auxotrophic for uracil and proline, the metabolites are uracil and proline;

wherein the auxotrophic *Pseudomonas fluorescens* host cell expressing the first and the second nucleotide sequences is grown to a density of at least about 20 grams per liter to about 150 grams per liter.

2. The process of claim 1, wherein the host cell is auxotrophic for the uracil and the proline.

3. The process of claim 1, wherein when the enzyme is orotidine-5'-phosphate decarboxylase, the polypeptide is encoded by the nucleic acid sequence as set forth in SEQ ID NO:1 or SEQ ID NO:3.

4. The process of claim 1, wherein when the polypeptide is $\Delta^1$-pyrroline-5-carboxylate reductase, the enzyme is encoded by the nucleic acid sequence as set forth in SEQ ID NO:6 or SEQ ID NO:8.

5. The process of claim 1, wherein when the auxotrophic *Pseudomonas fluorescens* host cell is auxotrophic for uracil the cell comprises a pyrF gene knockout.

6. The process of claim 5, wherein the pyrF gene comprises the nucleic acid sequence as set forth in SEQ ID NO:1 or SEQ ID NO:3.

7. The process of claim 1, wherein when the auxotrophic *Pseudomonas fluorescens* host cell is auxotrophic for proline the cell comprises a proC gene knockout.

8. The process of claim 7, wherein the proC gene comprises the nucleic acid sequence as set forth in SEQ ID NO:6 or SEQ ID NO:8.

9. The process of claim 1, wherein when the auxotrophic *P. fluorescens* host cell is auxotrophic for uracil and proline the cell comprises a pyrF and a proC gene knockout.

10. The process of claim 9, wherein the pyrF gene comprises the nucleic acid sequence as set forth in SEQ ID NO:1 or SEQ ID NO:3, and wherein the proC gene comprises the nucleic acid sequence as set forth in SEQ ID NO:6 or SEQ ID NO:8.

11. The process of claim 1, wherein said host cell lacks a nucleic acid sequence encoding an antibiotic selection marker and wherein said host cell is grown in the absence of an antibiotic.

12. The process of claim 1, wherein the lacI gene insert is other than as part of a PlacI-lacI-lacZYA operon.

13. The process of claim 1, wherein the lacI gene is selected from the group consisting of lacI, lacIQ, and lacIQ1.

14. The process of claim 1, wherein the nucleic acid construct further comprises at least one lac operator sequence.

15. The process of claim 14, wherein the at least one lac operator sequence comprises a first lac operator sequence located 5' of said promoter, and a second lac operator sequence located 3' of said promoter.

16. The process of claim 14, wherein the at least one lac operator sequence is a lacOid sequence.

17. The process of claim 14, wherein the lacOid sequence is selected from the group consisting of SEQ ID NO:14 and SEQ ID NO:59.

18. The process of claim 1, wherein the lacI gene is inserted in a levansucrase locus.

19. The process of claim 1, wherein said cell density is at least about: 25 grams per liter; 30 grams per liter; 35 grams per liter; 40 grams per liter; 45 grams per liter; 50 grams per liter; 60 grams per liter; 70 grams per liter; 80 grams per liter; 90 grams per liter; 100 grams per liter; 110 grams per liter; 120 grams per liter; 130 grams per liter; 140 grams per liter; or is about 150 grams per liter.

20. The process of claim 1, wherein said cell density is about 20 grams per liter to 70 grams per liter measured as dry cell weight.

* * * * *

SEQUENCE LISTING

```
<160> NUMBER OF SEQ ID NOS: 62

<210> SEQ ID NO 1
<211> LENGTH: 2650
<212> TYPE: DNA
<213> ORGANISM: Pseudomonas fluorescens
```

```
<400> SEQUENCE: 1
gatcagttgc ggagccttgg ggtcatcccc cagtttctga cgcaggcgcg acaccagcaa        60
gtcgatgctg cggtcgaaag cctcgatgga acgcccacgg gccgcgtcca gcagctgttc       120
gcggctcagc acacgccgcg ggcgttcgat aaacacccac aacaaacgaa actcggcgtt       180
ggacagcggc accaccaggc cgtcatcggc caccagctgg cgcagtacgc tgttcaggcg       240
ccaagtgtcg aaacggatat tgggccgctg ttcggtgcgg tcatcacgca cccggcgcag       300
gatggtctgg atacgcgcga ccagttcccg gggttcgaac ggcttggaca tatagtcgtc       360
tgcccccagt tccaggccga tgatgcggtc ggtgggttcg cagcgggcgg tgagcatcag       420
gatcggaatg tccgattcgg cgcgcagcca gcggcacaat gtcagcccgt cttcgcccgg       480
cagcatcagg tcgagcacca ccacatcgaa ggtctccgct tgcatggcct ggcgcatggc       540
gatgccgtcg gtgacgcctg aggcgagaat attgaagcgt gccaggtagt cgatcagcag       600
ttcgcggatc ggcacgtcgt cgtcgacaat cagcgcgcgg tgttccagc gcttgtcttc        660 ggcgatcacc gcgtctttg gcgcttcgtt tacagggtcg caaggggtat gcatagcgag        720
gtcatctgcc tggttgtggc tgtcagcata ggcgcccagt tccagggctg gaagtgctgg       780
gcgggcggtc atgtgcgcga ggctagccgg gcggcgtatt gggggcgtgt cgtgaatgta       840
tcgggcttga acaattgcc ttgaatcgcc ggtattgggc gcttgatcgg tatttaccga        900
tcatcggatc ccgcaacggc gctgcttgcg ctacaatccg cgccgatttc gacttgcctg       960
agagcccatt ccaatgtccg tctgccagac tcctatcatc gtcgccctgg attaccccac      1020
ccgtgacgcc gcactgaagc tggctgacca gttggacccc aagctttgcc gggtcaaggt      1080
cggcaaggaa ttgttcacca gttgcgcggc ggaaatcgtc ggcaccctgc gggacaaagg      1140
cttcgaagtg ttcctcgacc tcaaattcca tgacatcccc aacaccacgg cgatggccgt      1200
caaagccgcg gccgagatgg gcgtgtggat ggtcaatgtg cactgctccg gtggcctgcg      1260
catgatgagc gcctgccgcg aagtgctgga acagcgcagc ggccccaaac cgttgttgat      1320
cggcgtgacc gtgctcacca gcatggagcg cgaagacctg gcgggcattg gcctggatat      1380
cgagccgcag gtgcaagtgt tgcgcctggc agccctggcg cagaaagccg gcctcgacgg      1440
cctggtgtgc tcagccctgg aagcccaggc cctgaaaaac gcacatccgt cgctgcaact      1500
ggtgacaccg ggtatccgtc ctaccggcag cgcccaggat gaccagcgcc gtatcctgac      1560
cccgcgccag gccctggatg cgggctctga ctacctggtg atcggccggc cgatcagcca      1620
ggcggcggat cctgcaaaag cgttggcagc ggtcgtcgcc gagatcgcct gatttttaga      1680
gtgagcaaaa aatgtgggag ctggcttgcc tgcgatagta tcaactcggt atcacttaga      1740
aaccgagttg cttgcatcgc aggcaagcca gctcccacat ttgttttgt ggtgtgtcag       1800 ctgactttga gcaccaactt cccgaagttc tcgccgttga acagcttcat cagcgttttcc     1860 gggaatgtct ccagcccttc gacaatatct tccttgctct tgagcttgcc ctgggccatc      1920
cagccggcca tttcctgacc cgccgccgcg aagttcgccg cgtggtccat caccacaaag      1980
ccttccatac gcgcacggtt gaccagcaat gacaggtagt cgccgggcc tttgaccgct       2040 tccttgttgt tgtactggct gattgcaccg caaatcacca cgcgggcttt gagcgccagg      2100
cggctgagca ccgcgtcgag aatatcgccg ccgacgttat cgaaatacac gtccacgcct      2160
ttggggcact cgcgcttgag ggcggcgggc acgtcttcgc ttttgtagtc gatggcggcg      2220
tcgaagccca gctcatcgac caggaacttg cacttctcgg cgccaccggc gatccccact      2280
acgcgacagc ctttgagctt agcgatctgc ccggcgatgc tgcccacggc accggcggcg      2340
```

-continued

```
ccggagatca ccacggtgtc accggctttc ggtgcgccgg tctccagcag agcaaagtag    2400
gccgtcatgc cggtcatgcc cagggcggac aggtagcggg gcaggggcgc cagcttgggg    2460
tccaccttat agaaaccacg gggctcgcca aggaagtaat cctgcacgcc cagtgcaccg    2520
ttcacgtagt cccccaccgc gaagttcgga tggttcgagg caagcacctt gcctacgccc    2580
agggcgcgca tcacttcgcc gatgcctacc ggtgggatgt aggacttgcc ttcattcatc    2640
cagccacgca                                                           2650
```

<210> SEQ ID NO 2
<211> LENGTH: 232
<212> TYPE: PRT
<213> ORGANISM: Pseudomonas fluorescens

<400> SEQUENCE: 2

```
Met Ser Val Cys Gln Thr Pro Ile Ile Val Ala Leu Asp Tyr Pro Thr
1               5                   10                  15

Arg Asp Ala Ala Leu Lys Leu Ala Asp Gln Leu Asp Pro Lys Leu Cys
            20                  25                  30

Arg Val Lys Val Gly Lys Glu Leu Phe Thr Ser Cys Ala Ala Glu Ile
        35                  40                  45

Val Gly Thr Leu Arg Asp Lys Gly Phe Glu Val Phe Leu Asp Leu Lys
    50                  55                  60

Phe His Asp Ile Pro Asn Thr Thr Ala Met Ala Val Lys Ala Ala Ala
65                  70                  75                  80

Glu Met Gly Val Trp Met Val Asn Val His Cys Ser Gly Gly Leu Arg
                85                  90                  95

Met Met Ser Ala Cys Arg Glu Val Leu Glu Gln Arg Ser Gly Pro Lys
            100                 105                 110

Pro Leu Leu Ile Gly Val Thr Val Leu Thr Ser Met Glu Arg Glu Asp
        115                 120                 125

Leu Ala Gly Ile Gly Leu Asp Ile Glu Pro Gln Val Gln Val Leu Arg
    130                 135                 140

Leu Ala Ala Leu Ala Gln Lys Ala Gly Leu Asp Gly Leu Val Cys Ser
145                 150                 155                 160

Ala Leu Glu Ala Gln Ala Leu Lys Asn Ala His Pro Ser Leu Gln Leu
                165                 170                 175

Val Thr Pro Gly Ile Arg Pro Thr Gly Ser Ala Gln Asp Asp Gln Arg
            180                 185                 190

Arg Ile Leu Thr Pro Arg Gln Ala Leu Asp Ala Gly Ser Asp Tyr Leu
        195                 200                 205

Val Ile Gly Arg Pro Ile Ser Gln Ala Ala Asp Pro Ala Lys Ala Leu
    210                 215                 220

Ala Ala Val Val Ala Glu Ile Ala
225                 230
```

<210> SEQ ID NO 3
<211> LENGTH: 696
<212> TYPE: DNA
<213> ORGANISM: Pseudomonas fluorescens

<400> SEQUENCE: 3

```
atgtccgtct gccagactcc tatcatcgtc gccctggatt accccacccg tgacgccgca    60
ctgaagctgg ctgaccagtt ggaccccaag ctttgccggg tcaaggtcgg caaggaattg   120
ttcaccagtt gcgcggcgga aatcgtcggc accctgcggg acaaaggctt cgaagtgttc   180
```

-continued

```
ctcgacctca aattccatga catccccaac accacggcga tggccgtcaa agccgcggcc    240
gagatgggcg tgtggatggt caatgtgcac tgctccggtg gcctgcgcat gatgagcgcc    300
tgccgcgaag tgctggaaca gcgcagcggc cccaaaccgt tgttgatcgg cgtgaccgtg    360
ctcaccagca tggagcgcga agacctggcg ggcattggcc tggatatcga gccgcaggtg    420
caagtgttgc gcctggcagc cctggcgcag aaagccggcc tcgacggcct ggtgtgctca    480
gccctggaag cccaggccct gaaaaacgca catccgtcgc tgcaactggt gacaccgggt    540
atccgtccta ccggcagcgc ccaggatgac cagcgccgta tcctgacccc cgccaggcc    600 ctggatgcgg gctctgacta cctggtgatc ggccggccga tcagccaggc ggcggatcct    660
gcaaaagcgt tggcagcggt cgtcgccgag atcgcc                              696
```

<210> SEQ ID NO 4
<211> LENGTH: 834
<212> TYPE: DNA
<213> ORGANISM: Pseudomonas fluorescens
<400> SEQUENCE: 4

```
atgaagcaat atctcgaact actgaacgac gtcgtgacca atggattgac caagggcgat     60
cgcaccggca ccggcaccaa agccgtattt gcccgtcagt atcggcataa cttggccgac    120
ggcttcccgc tgctgaccac caagaagctt catttcaaaa gtatcgccaa cgagttgatc    180
tggatgttga gcggcaacac caacatcaag tggctcaacg aaaatggcgt gaaaatctgg    240
gacgagtggg ccaccgaaga cggcgacctg ggccggtgt acggcgagca atggaccgcc     300
tggccgacca aggacggcgg caagatcaac cagatcgact acatggtcca cccctcaaa    360 accaacccca cagccgccg catcctgttt catggctgga acgtcgagta cctgccggac    420
gaaaccaaga gcccgcagga aacgcgcgc aacggcaagc aagccttgcc gccgtgccat    480
ctgttgtacc aggcgttcgt gcatgacggg catctgtcga tgcagttgta tatccgcagc    540
tccgacgtct tcctcggcct gccgtacaac accgccgcgt tggccttgct gactcacatg    600
ctggctcagc aatgcgacct gatccctcac gagatcatcg tcaccaccgg cgacacccat    660
gcttacagca accacatgga acagatccgc acccagctgg cgcgtacgcc gaaaaagctg    720
ccggaactgg tgatcaagcg taaacctgcg tcgatctacg attacaagtt tgaagacttt    780
gaaatcgttg ctacgacgc cgaccccgagc atcaaggctg acgtggctat ctga           834
```

<210> SEQ ID NO 5
<211> LENGTH: 277
<212> TYPE: PRT
<213> ORGANISM: Pseudomonas fluorescens
<400> SEQUENCE: 5

```
Met Lys Gln Tyr Leu Glu Leu Leu Asn Asp Val Val Thr Asn Gly Leu
1               5                   10                  15

Thr Lys Gly Asp Arg Thr Gly Thr Gly Thr Lys Ala Val Phe Ala Arg
            20                  25                  30

Gln Tyr Arg His Asn Leu Ala Asp Gly Phe Pro Leu Leu Thr Thr Lys
        35                  40                  45

Lys Leu His Phe Lys Ser Ile Ala Asn Glu Leu Ile Trp Met Leu Ser
    50                  55                  60

Gly Asn Thr Asn Ile Lys Trp Leu Asn Glu Asn Gly Val Lys Ile Trp
65                  70                  75                  80

Asp Glu Trp Ala Thr Glu Asp Gly Asp Leu Gly Pro Val Tyr Gly Glu
                85                  90                  95
```

```
Gln Trp Thr Ala Trp Pro Thr Lys Asp Gly Lys Ile Asn Gln Ile
            100                 105                 110

Asp Tyr Met Val His Thr Leu Lys Thr Asn Pro Asn Ser Arg Arg Ile
        115                 120                 125

Leu Phe His Gly Trp Asn Val Glu Tyr Leu Pro Asp Glu Thr Lys Ser
    130                 135                 140

Pro Gln Glu Asn Ala Arg Asn Gly Lys Gln Ala Leu Pro Pro Cys His
145                 150                 155                 160

Leu Leu Tyr Gln Ala Phe Val His Asp Gly His Leu Ser Met Gln Leu
                165                 170                 175

Tyr Ile Arg Ser Ser Asp Val Phe Leu Gly Leu Pro Tyr Asn Thr Ala
            180                 185                 190

Ala Leu Ala Leu Leu Thr His Met Leu Ala Gln Gln Cys Asp Leu Ile
        195                 200                 205

Pro His Glu Ile Ile Val Thr Thr Gly Asp Thr His Ala Tyr Ser Asn
    210                 215                 220

His Met Glu Gln Ile Arg Thr Gln Leu Ala Arg Thr Pro Lys Lys Leu
225                 230                 235                 240

Pro Glu Leu Val Ile Lys Arg Lys Pro Ala Ser Ile Tyr Asp Tyr Lys
                245                 250                 255

Phe Glu Asp Phe Glu Ile Val Gly Tyr Asp Ala Asp Pro Ser Ile Lys
            260                 265                 270

Ala Asp Val Ala Ile
            275
```

<210> SEQ ID NO 6
<211> LENGTH: 1853
<212> TYPE: DNA
<213> ORGANISM: Pseudomonas fluorescens

<400> SEQUENCE: 6

```
gcccttgagt tggcacttca tcggccccat tcaatcgaac aagactcgtg ccatcgccga      60
gcacttcgct tgggtgcact ccgtggaccg cctgaaaatc gcacaacgcc tgtccgaaca     120
acgcccggcc gacctgccgc cgctcaatat ctgcatccag gtcaatgtca gtggcgaagc     180
cagcaagtcc ggctgcacgc ccgctgacct gccggcccctg ccacagcga tcagcgccct    240
gccgcgcttg aagctgcggg gcttgatggc gattcccgag ccgacgcaag accgggcgga     300
gcaggatgcg gcgttcgcca cggtgcgcga cttgcaagcc agcttgaacc tggcgctgga     360
cacactttcc atgggcatga ccacgacct tgagtcggcc attgcccaag cgccacctg      420
ggtgcggatc ggtaccgccc tgtttggcgc ccgcgactac ggccagccgt gaaatggctg     480
acatccctcg aaataaggac ctgtcatgag caacacgcgt attgccttta tcggcgccgg     540
taacatggcg gccagcctga tcggtggcct gcgggccaag ggcctggacg ccgagcagat     600
ccgcgccagc gaccccggtg ccgaaacccg cgagcgcgtc agagccgaac acggtatcca     660
gaccttcgcc gataacgccg aggccatcca cggcgtcgat gtgatcgtgc tggcggtcaa     720
gccccaggcc atgaaggccg tgtgcgagag cctgagcccg agcctgcaac ccatcaact     780
ggtggtgtcg attgccgctg gcatcacctg cgccagcatg accaactggc tcggtgccca     840
gcccattgtg cgctgcatgc caacacccc ggcgctgctg cgccagggcg tcagcggttt      900
gtatgccact ggcgaagtca ccgcgcagca acgtgaccag gcccaggaac tgctgtctgc     960
ggtgggcatc gccgtgtggc tggagcagga acagcaactg gatgcggtca ccgccgtctc    1020
cggcagcggc ccggcttact tcttcctgtt gatcgaggcc atgacggccg caggcgtcaa    1080
```

-continued

```
gctgggcctg ccccacgacg tggccgagca actggcggaa caaaccgccc tgggcgccgc    1140
caagatggcg gtcggcagcg aggtggatgc cgccgaactg cgccgtcgcg tcacctcgcc    1200
aggtggtacc acacaagcgg ctattgagtc gttccaggcc gggggctttg aagccctggt    1260
ggaaacagca ctgggtgccg ccgcacatcg ttcagccgag atggctgagc aactgggcaa    1320
atagtcgtcc cttaccaagg taatcaaaca tgctcggaat caatgacgct gccattttca    1380
tcatccagac cctgggcagc ctgtacctgc tgatcgtact gatgcgcttt atcctgcaac    1440
tggtgcgtgc gaacttctac aacccgctgt gccagttcgt ggtgaaggcc acccaaccgc    1500
tgctcaagcc gctgcgccgg gtgatcccga gcctgttcgg cctggacatg tcgtcgctgg    1560
tgctggcgct gttgctgcag attttgctgt tcgtggtgat cctgatgctc aatggatacc    1620
aggccttcac cgtgctgctg ttgccatggg gcctgatcgg gattttctcg ctgttcctga    1680
agatcatttt ctggtcgatg atcatcagcg tgatcctgtc ctgggtcgca ccgggtagcc    1740
gtagcccggg tgccgaattg gtggctcaga tcaccgagcc ggtgctggca cccttccgtc    1800
gcctgattcc gaacctgggt ggcctggata tctcgccgat cttcgcgttt atc           1853
```

<210> SEQ ID NO 7
<211> LENGTH: 272
<212> TYPE: PRT
<213> ORGANISM: Pseudomonas fluorescens

<400> SEQUENCE: 7

```
Met Ser Asn Thr Arg Ile Ala Phe Ile Gly Ala Gly Asn Met Ala Ala
1               5                   10                  15

Ser Leu Ile Gly Gly Leu Arg Ala Lys Gly Leu Asp Ala Glu Gln Ile
            20                  25                  30

Arg Ala Ser Asp Pro Gly Ala Glu Thr Arg Glu Arg Val Arg Ala Glu
        35                  40                  45

His Gly Ile Gln Thr Phe Ala Asp Asn Ala Glu Ala Ile His Gly Val
    50                  55                  60

Asp Val Ile Val Leu Ala Val Lys Pro Gln Ala Met Lys Ala Val Cys
65                  70                  75                  80

Glu Ser Leu Ser Pro Ser Leu Gln Pro His Gln Leu Val Val Ser Ile
                85                  90                  95

Ala Ala Gly Ile Thr Cys Ala Ser Met Thr Asn Trp Leu Gly Ala Gln
            100                 105                 110

Pro Ile Val Arg Cys Met Pro Asn Thr Pro Ala Leu Leu Arg Gln Gly
        115                 120                 125

Val Ser Gly Leu Tyr Ala Thr Gly Glu Val Thr Ala Gln Gln Arg Asp
    130                 135                 140

Gln Ala Gln Glu Leu Leu Ser Ala Val Gly Ile Ala Val Trp Leu Glu
145                 150                 155                 160

Gln Glu Gln Gln Leu Asp Ala Val Thr Ala Val Ser Gly Ser Gly Pro
                165                 170                 175

Ala Tyr Phe Phe Leu Leu Ile Glu Ala Met Thr Ala Ala Gly Val Lys
            180                 185                 190

Leu Gly Leu Pro His Asp Val Ala Glu Gln Leu Ala Glu Gln Thr Ala
        195                 200                 205

Leu Gly Ala Ala Lys Met Ala Val Gly Ser Glu Val Asp Ala Ala Glu
    210                 215                 220

Leu Arg Arg Arg Val Thr Ser Pro Gly Gly Thr Thr Gln Ala Ala Ile
225                 230                 235                 240

Glu Ser Phe Gln Ala Gly Gly Phe Glu Ala Leu Val Glu Thr Ala Leu
```

```
                245                 250                 255
Gly Ala Ala Ala His Arg Ser Ala Glu Met Ala Glu Gln Leu Gly Lys
            260                 265                 270
```

<210> SEQ ID NO 8
<211> LENGTH: 816
<212> TYPE: DNA
<213> ORGANISM: Pseudomonas fluorescens

<400> SEQUENCE: 8

```
atgagcaaca cgcgtattgc ctttatcggc gccggtaaca tggcggccag cctgatcggt      60
ggcctgcggg ccaagggcct ggacgccgag cagatccgcg ccagcgaccc cggtgccgaa     120
acccgcgagc gcgtcagagc cgaacacggt atccagacct cgccgataaa cgccgaggcc     180
atccacggcg tcgatgtgat cgtgctggcg gtcaagcccc aggccatgaa ggccgtgtgc     240
gagagcctga gcccgagcct gcaacccat caactggtgg tgtcgattgc cgctggcatc     300
acctgcgcca gcatgaccaa ctggctcggt gcccagccca ttgtgcgctg catgcccaac     360
accccggcgc tgctgcgcca gggcgtcagc ggtttgtatg ccactggcga agtcaccgcg     420
cagcaacgtg accaggccca ggaactgctg tctgcggtgg catcgccgt gtggctggag     480
caggaacagc aactggatgc ggtcaccgcc gtctccggca gcggcccggc ttacttcttc     540
ctgttgatcg aggccatgac ggccgcaggc gtcaagctgg cctgccccca cgacgtggcc     600
gagcaactgg cggaacaaac cgccctgggc gccgccaaga tggcggtcgg cagcgaggtg     660
gatgccgccg aactgcgccg tcgcgtcacc tcgccaggtg gtaccacaca gcggctatt      720
gagtcgttcc aggccggggg ctttgaagcc ctggtggaaa cagcactggg tgccgccgca     780
catcgttcag ccgagatggc tgagcaactg ggcaaa                               816
```

<210> SEQ ID NO 9
<211> LENGTH: 1330
<212> TYPE: DNA
<213> ORGANISM: Escherichia coli

<400> SEQUENCE: 9

```
gacaccatcg aatggcgcaa aacctttcgc ggtatggcat gatagcgccc ggaagagagt      60
caattcaggg tggtgaatgt gaaaccagta acgttatacg atgtcgcaga gtatgccggt     120
gtctcttatc agaccgtttc ccgcgtggtg aaccaggcca gccacgtttc tgcgaaaacg     180
cgggaaaaag tggaagcggc gatggcggag ctgaattaca ttcccaaccg cgtggcacaa     240
caactggcgg gcaaacagtc gttgctgatt ggcgttgcca cctccagtct ggccctgcac     300
gcgccgtcgc aaattgtcgc ggcgattaaa tctcgcgccg atcaactggg tgccagcgtg     360
gtggtgtcga tggtagaacg aagcggcgtc gaagcctgta aagcggcggt gcacaatctt     420
ctcgcgcaac gcgtcagtgg gctgatcatt aactatccgc tggatgacca ggatgccatt     480
gctgtggaag ctgcctgcac taatgttccg gcgttatttc ttgatgtctc tgaccagaca     540
cccatcaaca gtattatttt ctcccatgaa gacggtacgc gactgggcgt ggagcatctg     600
gtcgcattgg gtcaccagca atcgcgctgt tagcgggcc cattaagttc tgtctcggcg     660
cgtctgcgtc tggctggctg gcataaatat ctcactcgca atcaaattca gccgatagcg     720
gaacgggaag gcgactggag tgccatgtcc ggttttcaac aaaccatgca aatgctgaat     780
gagggcatcg ttcccactgc gatgctggtt gccaacgatc agatggcgct gggcgcaatg     840
cgcgccatta ccgagtccgg gctgcgcgtt ggtgcggata tctcggtagt gggatacgac     900
gataccgaag acagctcatg ttatatcccg ccgtcaacca ccatcaaaca ggattttcgc     960
```

```
ctgctggggc aaaccagcgt ggaccgcttg ctgcaactct ctcagggcca ggcggtgaag    1020
ggcaatcagc tgttgcccgt ctcactggtg aaaagaaaaa ccaccctggc gcccaatacg    1080
caaaccgcct ctccccgcgc gttggccgat tcattaatgc agctggcacg acaggtttcc    1140
cgactggaaa gcgggcagtg agcgcaacgc aattaatgtg agttagctca ctcattaggc    1200
accccaggct ttacacttta tgcttccggc tcgtatgttg tgtggaattg tgagcggata    1260
acaatttcac acaggaaaca gctatgacca tgattacgga ttcactggcc gtcgttttac    1320
aacgtcgtga                                                           1330
```

<210> SEQ ID NO 10
<211> LENGTH: 359
<212> TYPE: PRT
<213> ORGANISM: Escherichia coli

<400> SEQUENCE: 10

```
Met Lys Pro Val Thr Leu Tyr Asp Val Ala Glu Tyr Ala Gly Val Ser
 1               5                  10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Phe
145                 150                 155                 160

Ser His Glu Asp Gly Thr Arg Leu Gly Val Glu His Leu Val Ala Leu
                165                 170                 175

Gly His Gln Gln Ile Ala Leu Leu Ala Gly Pro Leu Ser Ser Val Ser
            180                 185                 190

Ala Arg Leu Arg Leu Ala Gly Trp His Lys Tyr Leu Thr Arg Asn Gln
        195                 200                 205

Ile Gln Pro Ile Ala Glu Arg Glu Gly Asp Trp Ser Ala Met Ser Gly
    210                 215                 220

Phe Gln Gln Thr Met Gln Met Leu Asn Glu Gly Ile Val Pro Thr Ala
225                 230                 235                 240

Met Leu Val Ala Asn Asp Gln Met Ala Leu Gly Ala Met Arg Ala Ile
                245                 250                 255

Thr Glu Ser Gly Leu Arg Val Gly Ala Asp Ile Ser Val Val Gly Tyr
            260                 265                 270

Asp Asp Thr Glu Asp Ser Ser Cys Tyr Ile Pro Pro Ser Thr Thr Ile
        275                 280                 285

Lys Gln Asp Phe Arg Leu Leu Gly Gln Thr Ser Val Asp Arg Leu Leu
    290                 295                 300
```

Gln Leu Ser Gln Gly Gln Ala Val Lys Gly Asn Gln Leu Leu Pro Val
305                 310                 315                 320

Ser Leu Val Lys Arg Lys Thr Thr Leu Ala Pro Asn Thr Gln Thr Ala
            325                 330                 335

Ser Pro Arg Ala Leu Ala Asp Ser Leu Met Gln Leu Ala Arg Gln Val
        340                 345                 350

Ser Arg Leu Glu Ser Gly Gln
        355

<210> SEQ ID NO 11
<211> LENGTH: 1320
<212> TYPE: DNA
<213> ORGANISM: Escherichia coli

<400> SEQUENCE: 11

| | | | | | |
|---|---|---|---|---|---|
| gacaccatcg | aatggtgcaa | aacctttcgc | ggtatggcat | gatagcgccc | ggaagagagt | 60 |
| caattcaggg | tggtgaatgt | gaaaccagta | acgttatacg | atgtcgcaga | gtatgccggt | 120 |
| gtctcttatc | agaccgtttc | ccgcgtggtg | aaccaggcca | gccacgtttc | tgcgaaaacg | 180 |
| cgggaaaaag | tggaagcggc | gatggcggag | ctgaattaca | ttcccaaccg | cgtggcacaa | 240 |
| caactggcgg | gcaaacagtc | gttgctgatt | ggcgttgcca | cctccagtct | ggccctgcac | 300 |
| gcgccgtcgc | aaattgtcgc | ggcgattaaa | tctcgcgccg | atcaactggg | tgccagcgtg | 360 |
| gtggtgtcga | tggtagaacg | aagcggcgtc | gaagcctgta | aagcggcggt | gcacaatctt | 420 |
| ctcgcgcaac | gcgtcagtgg | gctgatcatt | aactatccgc | tggatgacca | ggatgccatt | 480 |
| gctgtggaag | ctgcctgcac | taatgttccg | gcgttatttc | ttgatgtctc | tgaccagaca | 540 |
| cccatcaaca | gtattatttt | ctcccatgaa | gacggtacgc | gactgggcgt | ggagcatctg | 600 |
| gtcgcattgg | gtcaccagca | aatcgcgctg | ttagcgggcc | cattaagttc | tgtctcggcg | 660 |
| cgtctgcgtc | tggctggctg | gcataaatat | ctcactcgca | atcaaattca | gccgatagcg | 720 |
| gaacgggaag | gcgactggag | tgccatgtcc | ggttttcaac | aaaccatgca | aatgctgaat | 780 |
| gagggcatcg | ttcccactgc | gatgctggtt | gccaacgatc | agatggcgct | gggcgcaatg | 840 |
| cgcgccatta | ccgagtccgg | gctgcgcgtt | ggtgcggata | tctcggtagt | gggatacgac | 900 |
| gataccgaag | acagctcatg | ttatatcccg | ccgtcaacca | ccatcaaaca | ggattttcgc | 960 |
| ctgctggggc | aaaccagcgt | ggaccgcttg | ctgcaactct | ctcagggcca | ggcggtgaag | 1020 |
| ggcaatcagc | tgttgcccgt | ctcactggtg | aaaagaaaaa | ccaccctggc | gcccaatacg | 1080 |
| caaaccgcct | ctccccgcgc | gttggccgat | tcattaatgc | agctggcacg | acaggtttcc | 1140 |
| cgactggaaa | gcgggcagtg | agcgcaacgc | aattaatgtg | agttagctca | ctcattaggc | 1200 |
| accccaggct | ttacacttta | tgcttccggc | tcgtatgttg | tgtggaattg | tgagcggata | 1260 |
| acaatttcac | acaggaaaca | gctatgacca | tgattacgga | ttcactggcc | gtcgttttac | 1320 |

<210> SEQ ID NO 12
<211> LENGTH: 1324
<212> TYPE: DNA
<213> ORGANISM: Escherichia coli

<400> SEQUENCE: 12

| | | | | | |
|---|---|---|---|---|---|
| agcggcatgc | atttacgttg | acaccacctt | tcgcggtatg | gcatgatagc | gcccggaaga | 60 |
| gagtcaattc | agggtggtga | atgtgaaacc | agtaacgtta | tacgatgtcg | cagagtatgc | 120 |
| cggtgtctct | tatcagaccg | tttcccgcgt | ggtgaaccag | gccagccacg | tttctgcgaa | 180 |
| aacgcgggaa | aaagtggaag | cggcgatggc | ggagctgaat | tacattccca | accgcgtggc | 240 |

| | |
|---|---|
| acaacaactg gcgggcaaac agtcgttgct gattggcgtt gccacctcca gtctggccct | 300 |
| gcacgcgccg tcgcaaattg tcgcggcgat taaatctcgc gccgatcaac tgggtgccag | 360 |
| cgtggtggtg tcgatggtag aacgaagcgg cgtcgaagcc tgtaaagcgg cggtgcacaa | 420 |
| tcttctcgcg caacgcgtca gtgggctgat cattaactat ccgctggatg accaggatgc | 480 |
| cattgctgtg gaagctgcct gcactaatgt tccggcgtta tttcttgatg tctctgacca | 540 |
| gacacccatc aacagtatta tttttctccca tgaagacggt acgcgactgg gcgtggagca | 600 |
| tctggtcgca ttgggtcacc agcaaatcgc gctgttagcg ggcccattaa gttctgtctc | 660 |
| ggcgcgtctg cgtctggctg gctggcataa atatctcact cgcaatcaaa ttcagccgat | 720 |
| agcggaacgg gaaggcgact ggagtgccat gtccggtttt caacaaacca tgcaaatgct | 780 |
| gaatgagggc atcgttccca ctgcgatgct ggttgccaac gatcagatgg cgctgggcgc | 840 |
| aatgcgcgcc attaccgagt ccgggctgcg cgttggtgcg gatatctcgg tagtgggata | 900 |
| cgacgatacc gaagacagct catgttatat cccgccgtca accaccatca aacaggattt | 960 |
| tcgcctgctg gggcaaacca gcgtggaccg cttgctgcaa ctctctcagg gccaggcggt | 1020 |
| gaagggcaat cagctgttgc ccgtctcact ggtgaaaaga aaaaccaccc tggcgcccaa | 1080 |
| tacgcaaacc gcctctcccc gcgcgttggc cgattcatta atgcagctgg cacgacaggt | 1140 |
| ttcccgactg gaaagcgggc agtgagcgca acgcaattaa tgtgagttag ctcactcatt | 1200 |
| aggcaccccca ggctttacac tttatgcttc cggctcgtat gttgtgtgga attgtgagcg | 1260 |
| gataacaatt tcacacagga aacagctatg accatgatta cggattcact ggccgtcgtt | 1320 |
| ttac | 1324 |

<210> SEQ ID NO 13
<211> LENGTH: 3001
<212> TYPE: DNA
<213> ORGANISM: Pseudomonas fluorescens

<400> SEQUENCE: 13

| | |
|---|---|
| ctacccagaa cgaagatcag cgcctcaatg gcctcaaggt tctactggtc gatgattcag | 60 |
| ccgaagtcgt tgaggtgctg aacatgctgc tggaaatgga aggcgcccaa gtgagcgcct | 120 |
| tcagcgaccc tttgagcgcg cttgaaacag cccgggatgc ccattacgac gtgattattt | 180 |
| cggacatcgg catgccgaaa atgaatggcc atgagctgat gcagaagctg cgtaaagtag | 240 |
| gccaccttcg acaggctccc gccatcgcct taacgggcta tggcgctggc aatgaccaga | 300 |
| aaaaggcgac tgaatcgggc tttaatgcgc atgtcagcaa accgttggc catgattcgc | 360 |
| tcatcacctt gatcgaaaaa ctgtgccgct cccgccccta ggcgtggggc aggcgttcaa | 420 |
| gggtagatga actgagaaaa gcgcacggac gcgcccgttt ctggtcgcga cacctgggta | 480 |
| tccacgctgc caccgtgtc gctgcgcaag gtcaggtaca acacggcctg ccggcgctg | 540 |
| tcactcagca tccagacgct cacaccctcc ccggccgccc tggccttgag cggctgaggc | 600 |
| tgcagcatct cgatattgaa accgcgcagc agctcaccgc tcaactcgac ctccaggggt | 660 |
| tcctgggcct taccttgcac atgaatcacc agcccatcgg aggcgccatt gcgcaaaaag | 720 |
| cgttggtact ccacgcgcaa ctgcccatcg gcactgcgca cctcgcggct gctcagcggc | 780 |
| ccgctggaaa acagccctgc caagctcaag ccgatcagca ccagcagcgc gtaccaaccc | 840 |
| acccgctcaa agcgccagac cttgcgctgc aaggccatgt tttcctgcac cggataattg | 900 |
| cggctgtgta agtcgtcagg gtctgggttg ttcatagcgg ggcccggact caacccttgc | 960 |
| tgtgctcggg agaagacggc cccttggtga caccccgtgg gccggcaatc gcccatatcg | 1020 |

```
cagcgcccag aaacggcagc accacgacta ccgcactcca gcctgccttg ctggccgagg    1080
cgttatcgct gcgccagatg ctgttgatga tccacgcatc gagcagtacg aggatcactg    1140
ccaggcctat ccagaagtaa gtggtttgca tgatgcacct ccaggttatg taacttttgg    1200
tgcgcgggtg cgggcagggt tcattatttt taggttctct gcctggcgct tggtttgccg    1260
ccatcatgcg ggcaacttcg ccgatctact taatgatcga acctcttcaa acaagacaag    1320
ctgaaacgtc tcagctccta taaaaagcca aatcatgcac aaatgcattt tttgccttga    1380
ccacgggaat cgagtcttct aaagtcaaat cactgtatat gaatacagta atttgattcc    1440
cttcatggac gagacttact atgaaaagca ccccttcgaa atttggcaaa acaccccatc    1500
aacccagcct gtggacccgc gccgatgcgc ttaaagtgca tgcggacgac cccaccacca    1560
cccagccgct ggtcagcgcg aacttcccgg tattgagtga cgaggtgttt atctgggaca    1620
ccatgccgct gcgtgatatc gacggcaaca tcacctccgt cgatggctgg tcggtgatct    1680
tcaccctcac cgcggatcgc cacccgaacg acccgcaata cctcgatcag aatggcaact    1740
acgacgtcat ccgcgactgg aacgatcgcc atggccgggc aaagatgtac tactggttct    1800
cccgcaccgg caaagactgg aagctcggcg gccgagtgat ggctgaaggg gtttcgccca    1860
ccgtgcgcga atgggccggc acgccgatcc tgttgaacga gcaaggcgaa gtagacctgt    1920
actacaccgc cgtcacgccc ggcgcgacca tcgtcaaggt gcgtggccgc gtggtgacca    1980
ccgagcatgg cgtcagcctg gtgggctttg agaaggtcaa gccgctgttc gaggcggacg    2040
gcaagatgta ccagaccgaa gcgcaaaatg cgttctgggg cttttcgcgat ccatggccgt    2100 tccgcgaccc gaaagacggc aagctgtaca tgctgttcga aggtaacgtg gccggcgaac    2160
gcggctcgca caaggtcggt aaagccgaaa tcggcgacgt gccgccaggt tatgaagacg    2220
tcggtaactc gcgcttccag actgcctgcg tcggtatcgc cgtggcccgc gacgaagacg    2280
gcgacgactg ggaaatgctg ccaccgctgc tgaccgcggt gggcgtcaac gaccagaccg    2340
aacgcccgca cttcgtgttc caggacggca agtactacct gttcaccatc agccacacct    2400
tcacctacgc cgacgcgtg accggcccgg acggcgtgta cggcttcgtc gccgattcgc    2460
tgttcggtcc gtatgtgccg ttgaacggct ctggtctggt actgggcaac ccgtcctccc    2520
aaccgttcca gacctactcg cactgcgtca tgcccaacgg cctggtgacc tccttcatcg    2580
acagcgtacc gaccgacgac accggcacgc agatccgtat cggcggcacc gaagcaccga    2640
cggtgggcat caagatcaaa gggcagcaaa cgtttgtggt cgctgagtat gactacggtt    2700
acatcccgcc gatgctcgac gttacgctca gtaaccgga ggctatgagg tagcggcttt    2760
gagctcgatg acaaacccgc ggtgaatatt cgctgcacct gtggcgaggg agcttgctcc    2820
cggttgggcc ggacagccgc catcgcaggc aagccagctc ccacattttg gttcctgggg    2880
cgtcagggag gtatgtgtcg gctgaggggc cgtcacggga gcaagctccc tcgccacagg    2940
ttcaacagcc cattgggtgg atattcagga aatagaaatg cctgcaccat tgagttgagt    3000
c                                                                   3001
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic lacOid oligonucleotide

<400> SEQUENCE: 14
aattgtgagc gctcacaatt                                                20

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      MB214pyrR1 oligonucleotide

<400> SEQUENCE: 15
cgatcgggta cctgtcgaag ggctggagac at                                      32

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      pyrFPstF oligonucleotide

<400> SEQUENCE: 16
aactgcagga tcagttgcgg agccttgg                                           28

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      pyrFoverlap oligonucleotide

<400> SEQUENCE: 17
tgctcactct aaaaatctgg aatgggctct caggc                                   35

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      pyrFXbaR2 oligonucleotide

<400> SEQUENCE: 18
gctctagatg cgtggctgga tgaatgaa                                           28

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      pyranalF oligonucleotide

<400> SEQUENCE: 19
ggcgtcgaac aggtagcctt                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      pyranalR oligonucleotide

<400> SEQUENCE: 20
ctcgcctcct gccacatcaa                                                    20
```

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      M13F(-40) oligonucleotide

<400> SEQUENCE: 21
cagggttttc ccagtcacga                                              20

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      proC1 oligonucleotide

<400> SEQUENCE: 22
atatgagctc cgaccttgag tcggccattg                                   30

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      proC2 oligonucleotide

<400> SEQUENCE: 23
atatgagctc ggatccagta cgatcagcag gtacag                            36

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      proC3 oligonucleotide

<400> SEQUENCE: 24
agcaacacgc gtattgcctt                                              20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      proC5 oligonucleotide

<400> SEQUENCE: 25
gcccttgagt tggcacttca tcg                                          23

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      proC6 oligonucleotide

<400> SEQUENCE: 26
gataaacgcg aagatcggcg agata                                        25

<210> SEQ ID NO 27
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      proC7 oligonucleotide

<400> SEQUENCE: 27
ccgagcatgt ttgattagac aggtccttat ttcga                              35

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      proC8 oligonucleotide

<400> SEQUENCE: 28
tgcaacgtga cgcaagcagc atcca                                         25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      proC9 oligonucleotide

<400> SEQUENCE: 29
ggaacgatca gcacaagcca tgcta                                         25

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      genF2 oligonucleotide

<400> SEQUENCE: 30
atatgagctc tgccgtgatc gaaatccaga                                    30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      genR2 oligonucleotide

<400> SEQUENCE: 31
atatggatcc cggcgttgtg acaatttacc                                    30

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      XbaNotDraU2 linker oligonucleotide

<400> SEQUENCE: 32
tctagagcgg ccgcgtt                                                  17

<210> SEQ ID NO 33
<211> LENGTH: 17
<212> TYPE: DNA
<213> ORGANISM: Artificial Sequence
```

<220> FEATURE:
<223> OTHER INFORMATION: Description of Artificial Sequence: Synthetic
XbaNotDraL linker oligonucleotide

<400> SEQUENCE: 33
gcggccgctc tagaaac                                                    17

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
LEV1 oligonucleotide

<400> SEQUENCE: 34
ttcgaagggg tgcttttct agaagtaagt ctcgtccatg a                          41

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
LEV2 oligonucleotide

<400> SEQUENCE: 35
cgcaaggtca ggtacaacac                                                 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
LEV3 oligonucleotide

<400> SEQUENCE: 36
taccagacca gagccgttca                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
LEV7 oligonucleotide

<400> SEQUENCE: 37
ctacccagaa cgaagatcag                                                 20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
LEV8 oligonucleotide

<400> SEQUENCE: 38
gactcaactc aatggtgcag g                                               21

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic BglXbaLacF oligonucleotide

<400> SEQUENCE: 39
agatctctag agaaggcgaa gcggcatgca tttacg          36

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      lacIR4 oligonucleotide

<400> SEQUENCE: 40
atattctaga gacaactcgc gctaacttac attaattgc          39

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      Lacpro9 oligonucleotide

<400> SEQUENCE: 41
atattctaga atggtgcaaa acctttcgcg gtatggcatg a          41

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      LacIQF oligonucleotide

<400> SEQUENCE: 42
gctctagaag cggcatgcat ttacgttgac acc          33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      LacINXR oligonucleotide

<400> SEQUENCE: 43
agctagctct agaaagttgg gtaacgccag ggt          33

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      lacIQ1 oligonucleotide

<400> SEQUENCE: 44
agtaagcggc cgcagcggca tgcatttacg ttgacaccac ctttcgcggt atggcatg          58

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      lacIF1 oligonucleotide

```
<400> SEQUENCE: 45
acaatcttct cgcgcaacgc                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      lacIF2 oligonucleotide

<400> SEQUENCE: 46
atgttatatc ccgccgttaa                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      lacIR1 oligonucleotide

<400> SEQUENCE: 47
ccgctatcgg ctgaatttga                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      lacIR2 oligonucleotide

<400> SEQUENCE: 48
tgtaattcag ctccgccatc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      SeqLev5AS oligonucleotide

<400> SEQUENCE: 49
tatcgagatg ctgcagcctc                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      SeqLev3S oligonucleotide

<400> SEQUENCE: 50
acaccttcac ctacgccgac                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      LEV10 oligonucleotide

<400> SEQUENCE: 51
```
tctacttcgc cttgctcgtt                                              20

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      RC-3 oligonucleotide

<400> SEQUENCE: 52
gtgagcgctc acaattccac acaggaaaac ag                                32

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      RC-4 oligonucleotide

<400> SEQUENCE: 53
ttcgggtgga agtccaggta gttggcggtg ta                                32

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      RC-9 oligonucleotide

<400> SEQUENCE: 54
gaattgtgag cgctcacaat tccacacatt atacgagc                          38

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      RC-10 oligonucleotide

<400> SEQUENCE: 55
attcagcgca tgttcaacgg                                              20

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      AKB-1 oligonucleotide

<400> SEQUENCE: 56
acggttctgg caaacaattg tgagcgctca caatttattc tgaaatgagc             50

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      AKB-2 oligonucleotide

<400> SEQUENCE: 57
gcgtgggcgg tgtttatcat gttc                                         24

```
<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      AKB-3 oligonucleotide

<400> SEQUENCE: 58
tactgcacgc acaagcctga aca                                              23

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      lacOid sequence oligonucleotide

<400> SEQUENCE: 59
tgtgtggaat tgtgagcgct cacaattcca caca                                  34

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      MB214pyrF1 oligonucleotide

<400> SEQUENCE: 60
gcggccgctt tggcgcttcg tttacagg                                         28

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Trp Trp Pro
1

<210> SEQ ID NO 62
<211> LENGTH: 21
<212> TYPE: DNA
<213> ORGANISM: Escherichia coli

<400> SEQUENCE: 62
aattgtgagc ggataacaat t                                                21
```